United States Patent
Beskok et al.

(10) Patent No.: US 12,379,374 B2
(45) Date of Patent: Aug. 5, 2025

(54) SENSOR AND METHOD FOR DETECTING TARGET MOLECULES

(71) Applicant: Southern Methodist University, Dallas, TX (US)

(72) Inventors: Ali Beskok, Plano, TX (US); Anil Koklu, Dallas, TX (US); Jungchih Chiao, Dallas, TX (US)

(73) Assignee: Southern Methodist University, Dallas, TX (US)

( * ) Notice: Subject to any disclaimer, the term of this patent is extended or adjusted under 35 U.S.C. 154(b) by 0 days.

(21) Appl. No.: 18/585,915

(22) Filed: Feb. 23, 2024

(65) Prior Publication Data

US 2024/0219377 A1    Jul. 4, 2024

Related U.S. Application Data

(62) Division of application No. 17/171,829, filed on Feb. 9, 2021, now Pat. No. 11,965,878.
(Continued)

(51) Int. Cl.
  *B01L 3/00*       (2006.01)
  *B01F 33/302*    (2022.01)
  (Continued)

(52) U.S. Cl.
  CPC .......... *G01N 33/5302* (2013.01); *B01L 3/502* (2013.01); *C11D 3/3845* (2013.01);
  (Continued)

(58) Field of Classification Search
  CPC ............. G01N 33/5302; G01N 27/028; G01N 27/44726; G01N 33/48721;
  (Continued)

(56) References Cited

U.S. PATENT DOCUMENTS

| 4,554,101 A | 11/1985 | Hopp |
| 6,541,011 B2 | 4/2003 | Punnonen et al. |

(Continued)

OTHER PUBLICATIONS

Liao, et al., "Microfluidic chip coupled with optical biosensors for simultaneous detection of multiple analytes: A review.," Biosens. Bioelectron., vol. 126, pp. 697-706, 2019.

(Continued)

*Primary Examiner* — Jennifer Wecker
*Assistant Examiner* — Oyeleye Alexander Alabi
(74) *Attorney, Agent, or Firm* — Edwin S. Flores; Daniel J. Chalker; Chalker Flores, LLP

(57) ABSTRACT

An apparatus and method for detecting one or more target molecules includes a hydrophobic substrate, and a sensor. The sensor includes two or more electrodes disposed on the hydrophobic substrate and separated from one another by a gap, a plurality of nanostructures formed on or within an upper surface of each electrode, a plurality of binding molecules attached to the plurality of nanostructures, wherein the plurality of binding molecules are configured to bind with the one or more target molecules, and wherein the upper surface of each electrode and the plurality of nanostructures are hydrophilic, and may further detect two or more analytes with two or more sensors that detect two or more different modalities, such as, electrical, optical fluorescence, optical resonance, magnetic detection, or acoustic waves.

9 Claims, 21 Drawing Sheets

Related U.S. Application Data

(60) Provisional application No. 63/131,155, filed on Dec. 28, 2020, provisional application No. 62/972,386, filed on Feb. 10, 2020.

(51) Int. Cl.

| | |
|---|---|
| B01F 33/3033 | (2022.01) |
| B01L 7/00 | (2006.01) |
| B01L 9/00 | (2006.01) |
| B65G 47/80 | (2006.01) |
| B82Y 20/00 | (2011.01) |
| B82Y 30/00 | (2011.01) |
| B82Y 40/00 | (2011.01) |
| C11D 3/384 | (2006.01) |
| C12M 1/34 | (2006.01) |
| C12M 3/06 | (2006.01) |
| C12N 1/14 | (2006.01) |
| C12N 1/20 | (2006.01) |
| C12Q 1/02 | (2006.01) |
| C12Q 1/6848 | (2018.01) |
| C12Q 1/686 | (2018.01) |
| G01N 15/10 | (2024.01) |
| G01N 15/14 | (2024.01) |
| G01N 15/1433 | (2024.01) |
| G01N 21/29 | (2006.01) |
| G01N 21/65 | (2006.01) |
| G01N 27/02 | (2006.01) |
| G01N 27/447 | (2006.01) |
| G01N 33/487 | (2006.01) |
| G01N 33/53 | (2006.01) |
| G01N 33/543 | (2006.01) |
| G01N 33/574 | (2006.01) |
| G01N 33/58 | (2006.01) |
| B61L 3/24 | (2006.01) |
| C08J 9/236 | (2006.01) |

(52) U.S. Cl.
CPC ..... *G01N 27/028* (2013.01); *G01N 27/44726* (2013.01); *G01N 33/48721* (2013.01); *G01N 33/5438* (2013.01); *B01J 2219/00813* (2013.01); *B01L 2300/0645* (2013.01); *B01L 2300/088* (2013.01); *B01L 2300/161* (2013.01); *B61L 3/243* (2013.01); *C08J 9/236* (2013.01)

(58) Field of Classification Search
CPC .. G01N 33/5438; G01N 33/492; B01L 3/502; B01L 2300/0645; B01L 2300/088; B01L 2300/161; B01L 3/502707; B01L 2400/0415; B01L 2400/0451; B01L 3/50273; C11D 3/3845; B01J 2219/00813; B61L 3/243; C08J 9/236
See application file for complete search history.

(56) References Cited

U.S. PATENT DOCUMENTS

| | | | | |
|---|---|---|---|---|
| 2006/0043284 A1* | 3/2006 | Baba | ........ | B01L 3/502746 250/284 |
| 2012/0118751 A1* | 5/2012 | Cai | ........ | G01N 33/54346 977/773 |
| 2013/0146459 A1* | 6/2013 | Bazant | ........ | B01L 3/502784 204/601 |
| 2014/0121192 A1 | 5/2014 | Buynak | | |
| 2015/0247816 A1* | 9/2015 | Bhansali | ........ | G01N 27/3275 204/403.01 |
| 2016/0003761 A1 | 1/2016 | Clark et al. | | |
| 2016/0116427 A1* | 4/2016 | Laurenson | ........ | B05D 5/00 427/2.13 |
| 2017/0350856 A1 | 12/2017 | Kobayashi | | |

OTHER PUBLICATIONS

Lin, et al., "Molecular Characterization of Epithelial to Mesenchymal Transition in Human Prostatic Epithelial Cells.," J. Nanotechnol. Eng. Med., vol. 1, p. 2, 2010.

Ma, et al. "ELISA Technique.," Nat Sci, vol. 4, No. 2, pp. 36-37, 2006.

McWilliam, et al. "Inkjet printing for the production of protein microarrays", Protein Microarrays. Humana Press, 2011.

Merck "Overview of Enterovirus Infections," Merck Co, Feb. 2018.

Mrozik, et al., "N-cadherin in cancer metastasis, its emerging role in haematological malignancies and potential as a therapeutic target in cancer," BMC Cancer, vol. 18, No. 1, p. 939, 2018.

Ng, et al., "DC-biased AC-electroosmotic and AC-electrothermal flow mixing in microchannels.," Lab Chip, vol. 9, No. 6, pp. 802-809, 2009.

Nguyen, et al., "Micro pH Sensors Based on Iridium Oxide Nanotubes," IEEE Trans. Nanotechnol., vol. 13, No. 5, pp. 945-953, Sep. 2014.

Nguyen, et al., "Miniature neurotransmitter sensors featured with iridium oxide nanorods," in IEEE Sensors, 2014, vol. 2014, pp. 1869-1872.

Nile, et al., "COVID-19: Pathogenesis, cytokine storm and therapeutic potential of interferons," Cytokine Growth Factor Rev., vol. S1359-6101, No. 20, 2020.

Okba, et al., "Severe Acute Respiratory Syndrome Coronavirus 2-Specific Antibody Responses in Coronavirus Disease 2019 Patients.," Emerg. Infect. Dis., vol. 26, p. 7, 2020.

Park, et al., "Particle trapping in high-conductivity media with electrothermally enhanced negative dielectrophoresis.," Anal. Chem., vol. 81, No. 6, pp. 2303-2310, 2009.

Pfeiffer, et al. "Microfluidic platforms employing integrated fluorescent or luminescent chemical sensors: a review of methods, scope and applications," Methods Appl. Fluoresc., vol. 3, No. 3, pp. 034003, 2015.

Prodromidis, M. I., "Impedimetric immunosensors—A review.," Electrochim. Acta, vol. 55, No. 14, pp. 4227-4233, 2010.

Qin, et al., "Significantly improved analytical sensitivity of lateral flow immunoassays by using thermal contrast.," Angew. Chemie Int. Ed., vol. 51, No. 18, pp. 4358-4361, 2012.

Rao, M.-N., "Platform To Study Cell Migration." Dissertation, 2009.

Rao, et al., "The migration of cancer cells in gradually varying chemical gradients and mechanical constraints.," Micromachines, vol. 5, No. 1, pp. 13-26, 2014.

Rashid, et al., "Diagnostic performance of COVID-19 serology assays.," Malays. J. Pathol., vol. 42, No. 1, pp. 13-21, 2020.

Rivas, et al., "Improving sensitivity of gold nanoparticle-based lateral flow assays by using wax-printed pillars as delay barriers of microfluidics," Lab Chip, vol. 14, No. 22, pp. 4406-4414, 2014.

Rodriguez-Lorenzo, et al., "Multiplex optical sensing with surface-enhanced Raman scattering: a critical review.," Anal. Chim. Acta, vol. 745, pp. 10-23, 2012.

Roth, et al., "Inkjet printing for high-throughput cell patterning.," Biomaterials, vol. 25, No. 17, pp. 3707-3715, 2004.

Sajid, et al., "Designs, formats and applications of lateral flow assay: A literature review," J. Saudi Chem. Soc., vol. 19, No. 6, pp. 689-705, 2015.

Sa-Ngasang, et al., "Specific IgM and IgG responses in primary and secondary dengue virus infections determined by enzyme-linked immunosorbent assay.," Epidemiol. Infect., vol. 134, No. 4, pp. 820-825, 2006.

Sargent, et al. "Monitoring antibody-antigen reactions at conducting polymer-based immunosensors using impedance spectroscopy.," Electrochim. Acta, vol. 44, No. 26, pp. 4667-4675, 1999.

Schultz, et al., "Diagnosis and treatment of viral myocarditis," Mayo Clin. Proc., vol. 84, No. 11, pp. 1001-1009, Nov. 2009.

(56) References Cited

OTHER PUBLICATIONS

Shin, et al., "Aptamer-based microfluidic electrochemical biosensor for monitoring cell-secreted trace cardiac biomarkers.," Anal. Chem., vol. 88, No. 20, pp. 10019-10027, 2016.
Siracusano, et al., "Humoral immunity in COVID-19 patients: a window on the state of the art.," Front. Immunol., vol. 11, p. 1049, 2020.
Smith, et al., "Quantum Dot Nanocrystals for In Vivo Molecular and Cellular Imaging.," Photochem. Photobiol., vol. 80, No. 3, pp. 377-385, 2004.
Smits, et al., "Lateral-flow assay for rapid serodiagnosis of human leptospirosis.," Clin. Diagn. Lab. Immunol., vol. 8, No. 1, pp. 166-169, 2001.
Spreeuwenberg, et al., "Reassessing the Global Mortality Burden of the 1918 Influenza Pandemic," Am. J. Epidemiol., vol. 187, No. 12, pp. 2561-2567, Dec. 2018.
Streets, et al. "Chip in a lab: Microfluidics for next generation life science research.," Biomicrofluidics, vol. 7, No. 1, pp. 011302, 2013.
Tahamtan, et al. "Real-time RT-PCR in COVID-19 detection: issues affecting the results.," Expert Rev Mol Diagn., vol. 20, No. 5, pp. 453-454, 2020.
Tan, et al., "A PDMS microfluidic impedance immunosensor for *E. coli* O157: H7 and *Staphylococcus aureus* detection via antibody-immobilized nanoporous membrane.," Sensors Actuators B Chem., vol. 159, No. 1, pp. 328-335, 2011.
Tang, et al., "The laboratory diagnosis of COVID-19 infection: current issues and challenges.," J. Clin. Microbiol., 2020.
Tata, et al., "Study of lung-metastasized prostate cancer cell line chemotaxis to epidermal growth factor with a BIOMEMS device.," Adv. Nat. Sci. Nanosci. Nanotechnol., vol. 3, No. 3, pp. 035007, 2012.
Tsien, R. Y., The green fluorescent protein. Annu Rev Biochem, 1998, 67:409-44.
Vashist, S. K., "In vitro diagnostic assays for COVID-19 recent advances and emerging trends," Diagnostics, vol. 10, No. 4, p. 202, 2020.
Wang, et al., "Quantum-Dot-based electrochemical immunoassay for high-throughput screening of the prostate-specific antigen.," Small, vol. 4, No. 1, pp. 82-86, 2008.
WHO, "Up to 650 000 people die of respiratory diseases linked to seasonal flu each year," World Health Organization (WHO) (Press release), Dec. 14, 2017.
WHO, "Key facts about Malaria," World Health Organization, Jan. 14, 2020.
Wu, et al., "Micropumping of biofluids by alternating current electrothermal effects.," Appl. Phys. Lett., vol. 90, No. 23, pp. 234103, 2007.
Yoo, et al., "Optical biosensors for the detection of pathogenic microorganisms.," Trends Biotechnol., vol. 34, No. 1, pp. 7-25, 2016.
Zhang, et al., "Clinical and pharmaceutical applications of affinity ligands in capillary electrophoresis: A review," J. Pharm. Biomed. Anal., vol. 177, pp. 112882, 2020.
Zhao, et al., "Vimentin affects the mobility and invasiveness of prostate cancer cells," Cell Biochem. Funct. Cell. Biochem. its Modul. by Act. agents or Dis., vol. 26, No. 5, pp. 571-577, 2008.
Zhao, et al., "Microfluidic generation of multifunctional quantum dot barcode particles.," J. Am. Chem. Soc., vol. 133, No. 23, pp. 8790-8793, 2011.
Zhong, et al., "Detection of serum IgM and IgG for COVID-19 diagnosis.," Sci. China Life Sci., vol. 63, pp. 777-780, 2020.
Zhou, et al. "The Dynamic changes of Serum IgM and IgG against SARS-COV-2 in patients with COVID 19" J. Med Virol. 2021: 93:924-933.
Zumla, et al. "Middle East respiratory syndrome," Lancet., vol. 386, No. 9997, pp. 995-1007, Sep. 2015.
Abbasi, J., "The promise and peril of antibody testing for COVID-19," JAMA, vol. 323, No. 19, pp. 1881-1883, 2020.

Abe, et al., "Inkjet-printed paper-fluidic immuno-chemical sensing device," Anal Bioanal Chem, vol. 398, No. 2, pp. 885-893, 2010.
Assiri, et al., "Epidemiological, demographic, and clinical characteristics of 47 cases of Middle East respiratory syndrome coronavirus disease from Saudi Arabia: a descriptive study," Lancet, vol. 13, p. 9.
Baez-Santos, et al., "The SARS-coronavirus papain-like protease: Structure, function and inhibition by designed antiviral compounds," Antiviral Res., vol. 115, pp. 21-38, 2015.
Barat, et al., "Simultaneous high speed optical and impedance analysis of single particles with a microfluidic cytometer," Lab on a Chip, vol. 12, No. 1, pp. 118-126, 2012.
Bazant, et al., "Electrolyte dependence of AC electro-osmosis," Micro Total Anal. Syst., vol. 1, pp. 285-287, 2007.
Bendavid, et al., COVID-19 Antibody Seroprevalence in Santa Clara County, California. MedRxiv, 2020.
Bera, et al., "Synthesis of nanostructured materials using template-assisted electrodeposition," Jom, vol. 56, No. 1, pp. 49-53, 2004.
Brankston et al., "Transmission of influenza A in human beings," Lancet Infect Dis, vol. 7, No. 4, pp. 257-265, Apr. 2007.
Bridle, et al., "Application of microfluidics in waterborne pathogen monitoring: A review." Water Research, vol. 55, pp. 256-271, 2014.
Burch D. and M. Z. Bazant, "Design principle for improved three-dimensional ac electro-osmotic pumps," Phys. Rev. E, vol. 77, pp. 055303, 2008.
Cassaniti, et al., "Performance of VivaDiag COVID-19 IgM/IgG Rapid Test is inadequate for diagnosis of COVID-19 in acute patients referring to emergency room department," J. Med. Virol., vol. 19, 2020.
CDC, "Key Facts About Influenza (Flu)," Centers for Disease Control and Prevention (CDC), 2014.
Chan, et al. "Quantum dot bioconjugates for ultrasensitive nonisotopic detection," Science, vol. 281, No. 5385, pp. 2016-2018, 1998.
Chan, et al., "Luminescent quantum dots for multiplexed biological detection and imaging," Curr. Opin. Biotechnol., vol. 13, No. 1, pp. 40-46, 2002.
Chamow, et al. "Immunoadhesins: principles and applications. Trends in biotechnology," vol. 14, No. 2, pp. 52-60, 1996.
Chen, et al., "Microfluidic impedance flow cytometry enabling high-throughput single-cell electrical property characterization," Int. J. Mol. Sci., vol. 16, No. 5, pp. 9804-9830, 2015.
Ching, et al., "COVID-19 Special Column: Principles Behind the Technology for Detecting SARS-COV-2, the Cause of COVID-19.," Hawai"i J. Heal. Soc. Welf., vol. 79, p. 136, 2020.
Choi, et al., "On-site quantification of human urinary albumin by a fluorescence immunoassay," Clin. Chem., vol. 50, No. 6, pp. 1052-1055, 2004.
CIDRAP, ""Pandemic H1N1 2009 Influenza". CIDRAP. Center for Infectious Disease Research Policy, University of Minnesota.," 2011.
Didar, et al., "Patterning multiplex protein microarrays in a single microfluidic channel.," Anal. Chem., vol. 84, No. 2, pp. 1012-1018, 2012.
Du, et al., "Microfluidic pumping optimization in microgrooved channels with ac electrothermal actuations.," Appl. Phys. Lett., vol. 96, No. 3, pp. 034102, 2010.
Feyssa, et al., "Patterned immobilization of antibodies within roll-to-roll hot embossed polymeric microfluidic channels," PLoS One, vol. 8, p. 7, 2013.
Fradkov, et al., "Far-red fluorescent tag for protein labelling," Biochem. J., vol. 368, No. 1, pp. 17-21, 2002.
Frankowski, et al., "Simultaneous optical and impedance analysis of single cells: A comparison of two microfluidic sensors with sheath flow focusing," Eng. Life Sci., vol. 15, No. 3, pp. 286-296, 2015.
Gattas-Asfura, et al., "Immobilization of quantum dots in the photo-cross-linked poly (ethylene glycol)-based hydrogel.," J. Phys. Chem. B, vol. 107, No. 38, pp. 10464-10469, 2003.
Gerdes, et al. "Green fluorescent protein: applications in cell biology," FEBS Lett., vol. 389, No. 1, pp. 44-47, 1996.
Gong, et al., "A review of fluorescent signal-based lateral flow immunochromatographic strips.," J. Mater. Chem. B, vol. 5, No. 26, pp. 5079-5091, 2017.

(56) References Cited

OTHER PUBLICATIONS

Guo, et al., "Profiling early humoral response to diagnose novel coronavirus disease (COVID-19)," Clin. Infect. Dis., vol. 2020.

Guo, et al., "An inkjet printing paper-based immunodevice for fluorescence determination of immunoglobulin G.," Anal. Methods, vol. 11, No. 27, pp. 3452-3459, 2019.

Halldorsson, et al., "Advantages and challenges of microfluidic cell culture in polydimethylsiloxane devices.," Biosens. Bioelectron., vol. 63, pp. 218-231, 2015.

Han, et al., "Microfluidic chips for immunoassays.," Annu. Rev. Anal. Chem., vol. 6, pp. 119-141, 2013.

Hauser, et al., "High-yield passive plasma filtration from human finger prick blood.," Anal. Chem., vol. 90, No. 22, pp. 13393-13399, 2018.

Hu, et al. "Applications and trends in electrochemiluminescence.," Chem. Soc. Rev., vol. 39, No. 8, pp. 3275-3304, 2010.

Janeway, et al., The distribution and functions of immunoglobulin isotypes. In Immunobiology: The Immune System in Health and Disease. 5th edition. 2001.

Joh, et al., "Inkjet-printed point-of-care immunoassay on a nanoscale polymer brush enables subpicomolar detection of analytes in blood," Proc. Natl. Acad. Sci., vol. 114, No. 34, pp. 7054-E7062, 2017.

Joung, et al., "An automatic enzyme immunoassay based on a chemiluminescent lateral flow immunosensor," Biosens. Bioelectron., vol. 53, pp. 330-335, 2014.

Kabiraj, et al., "Principle and techniques of immunohistochemistry—a review.," Int J Biol Med Res, vol. 6, No. 3, pp. 5204-5210, 2015.

Kaler, et al. "Droplet microfluidics for chip-based diagnostics.," Sensors, vol. 14, No. 12, pp. 23283-23306, 2014.

Katz, et al. "Probing biomolecular interactions at conductive and semiconductive surfaces by impedance spectroscopy: routes to impedimetric immunosensors, DNA-sensors, and enzyme biosensors," Electroanal. An Int. J. Devoted to Fundam. Pract. Asp. Electroanal., vol. 15, No. 11, pp. 913-947, 2003.

Kobayashi, et al., "Engineering a novel multifunctional green fluorescent protein tag for a wide variety of protein research," PLoS One, vol. 3, p. 12, 2008.

Koczula, et al. "Lateral flow assays," Essays Biochem., vol. 60, No. 1, pp. 111-120, 2016.

Koivunen, et al. "Principles of immunochemical techniques used in clinical laboratories," Lab. Med., vol. 37, No. 8, pp. 490-497, 2006.

Koklu, et al., "Self-Similar Interfacial Impedance of Electrodes in High Conductivity Media: II. Disk Electrodes," Anal. Chem., vol. 91, No. 3, pp. 2455-2463, 2019.

Koklu, et al., Rapid and Sensitive Detection of Nanomolecules by AC Electrothermal Flow Facilitated Impedance Immunosensor. Analytical Chemistry, 2020.

Kontou, et al., "Antibody tests in detecting SARS-COV-2 infection: a meta-analysis. Diagnostics," vol. 10, No. 5, p. 319, 2020.

Leva-Bueno, et al., A review on impedimetric immunosensors for pathogen and biomarker detection. Medical Microbiology and Immunology. 2020.

Li, et al. "Multiplexed lateral flow biosensors: Technological advances for radically improving point-of-care diagnoses.," Biosens. Bioelectron., vol. 83, pp. 177-192, 2016.

Lian, et al., "AC electrothermal manipulation of conductive fluids and particles for lab-chip applications.," IET Nanobiotechnology, vol. 1, No. 3, pp. 36-43, 2007.

Liang, et al., "Severe acute respiratory syndrome-retrospect and lessons of 2004 outbreak in China," Biomed Env. Sci., vol. 19, No. 6, pp. 445-451, 2006.

\* cited by examiner

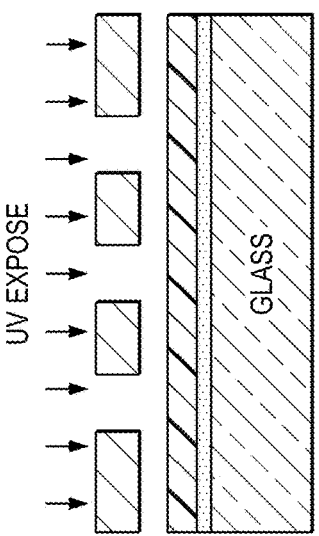
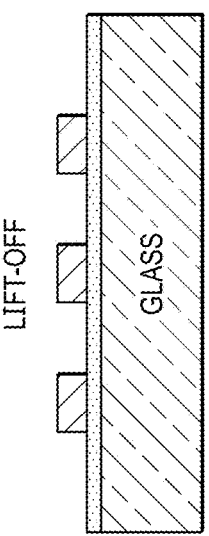
FIG. 1A  FIG. 1B  FIG. 1C
FIG. 1D  FIG. 1E  FIG. 1F

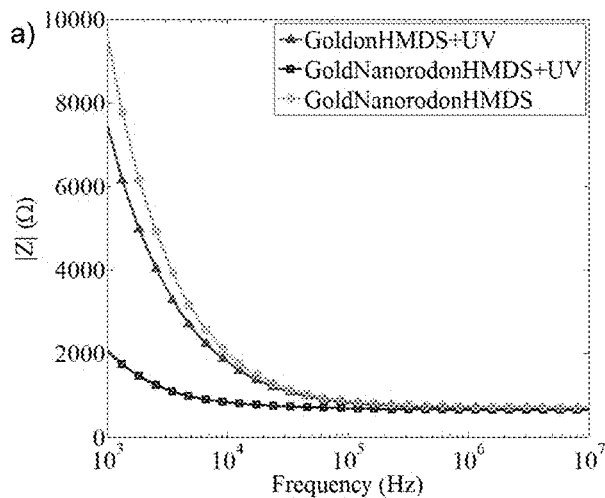
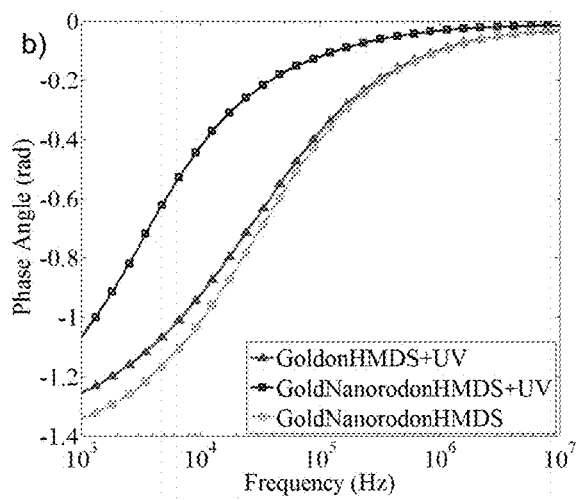
FIG. 6A  FIG. 6B
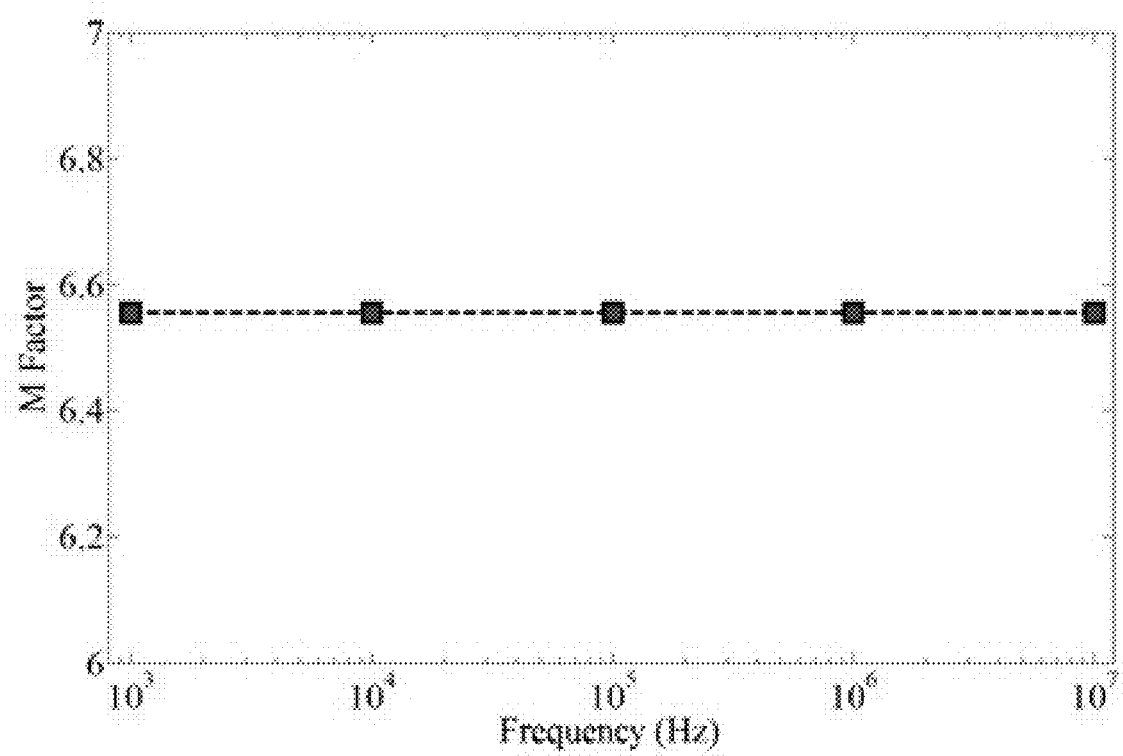
FIG. 7

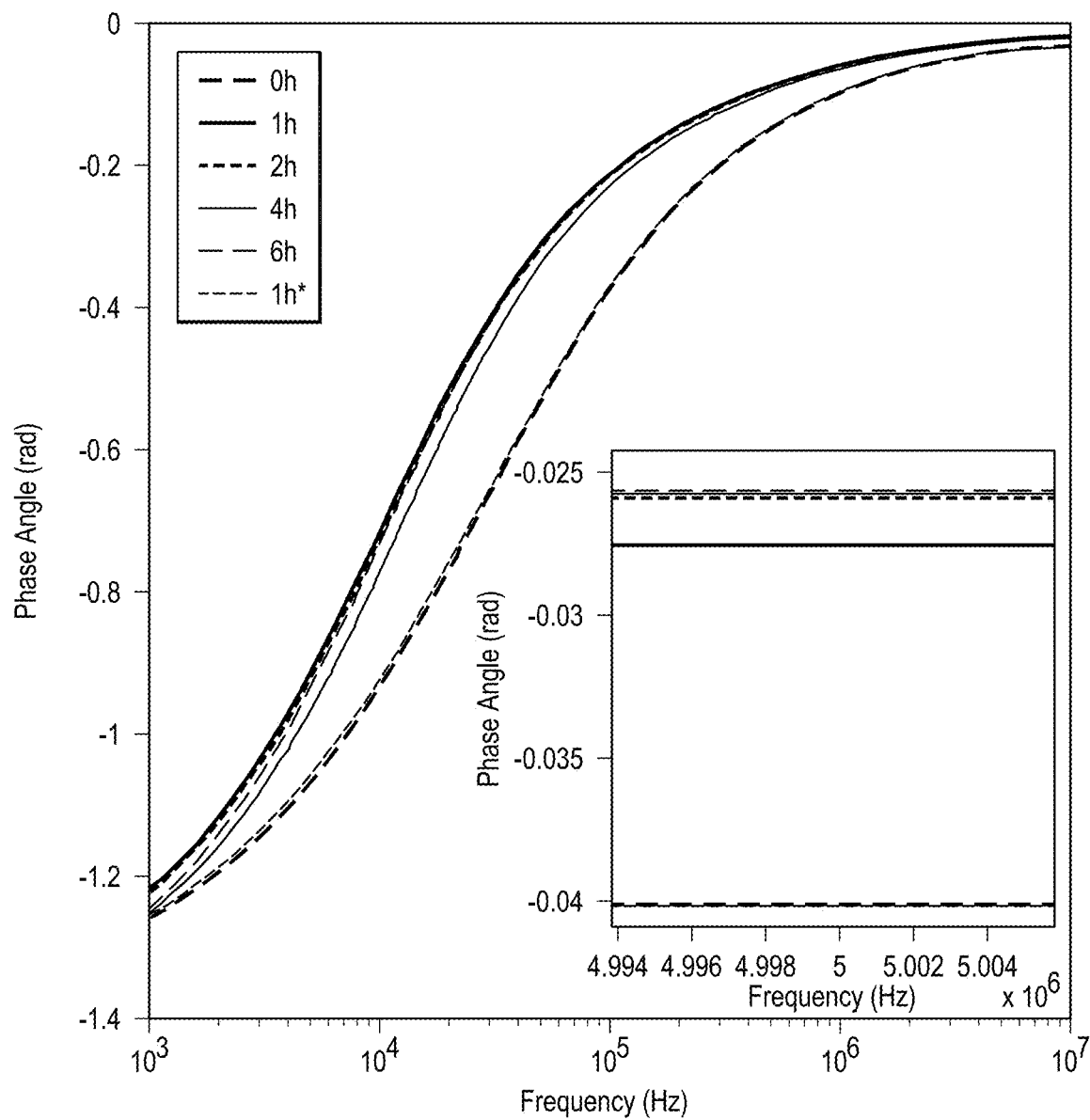

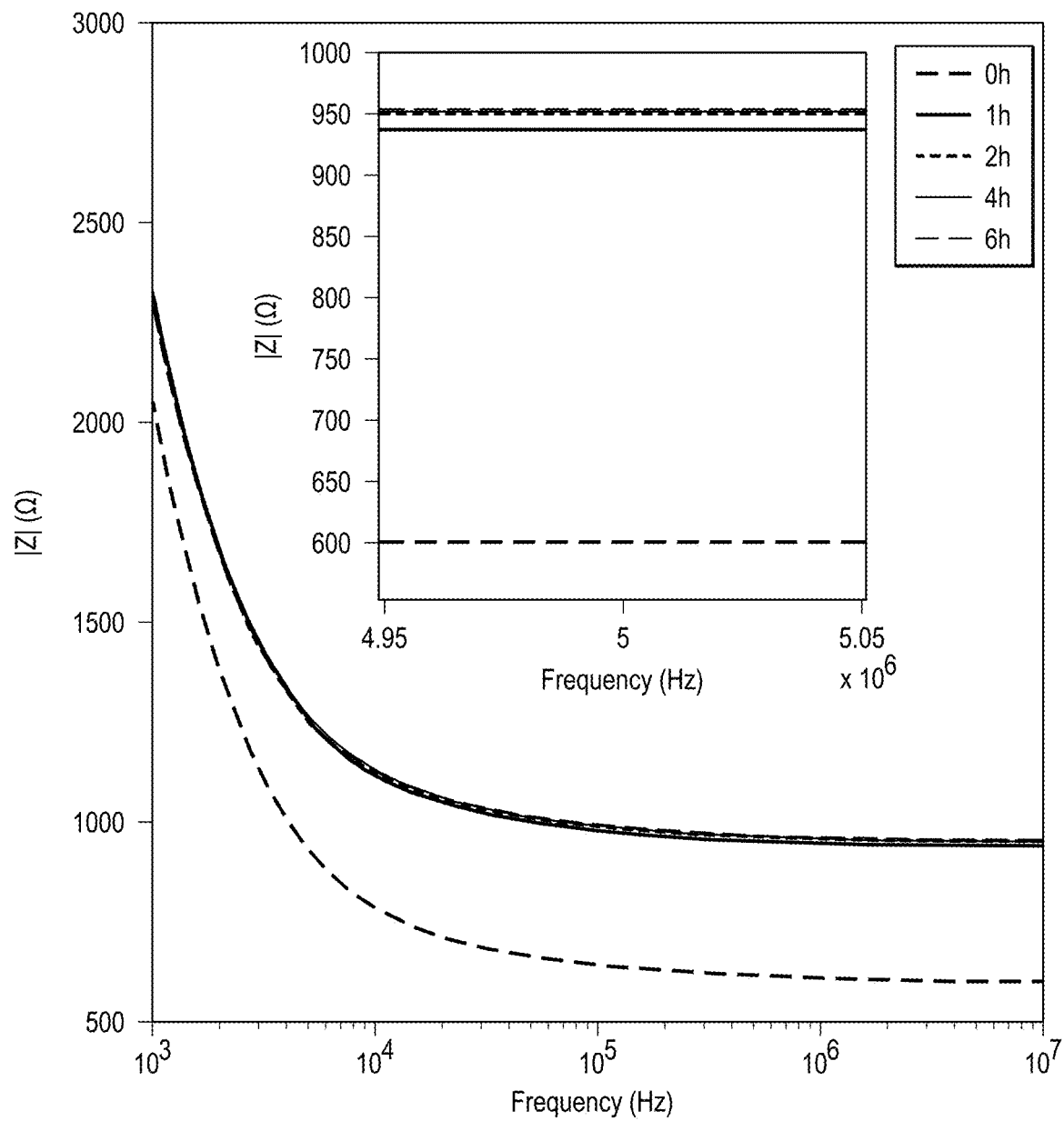

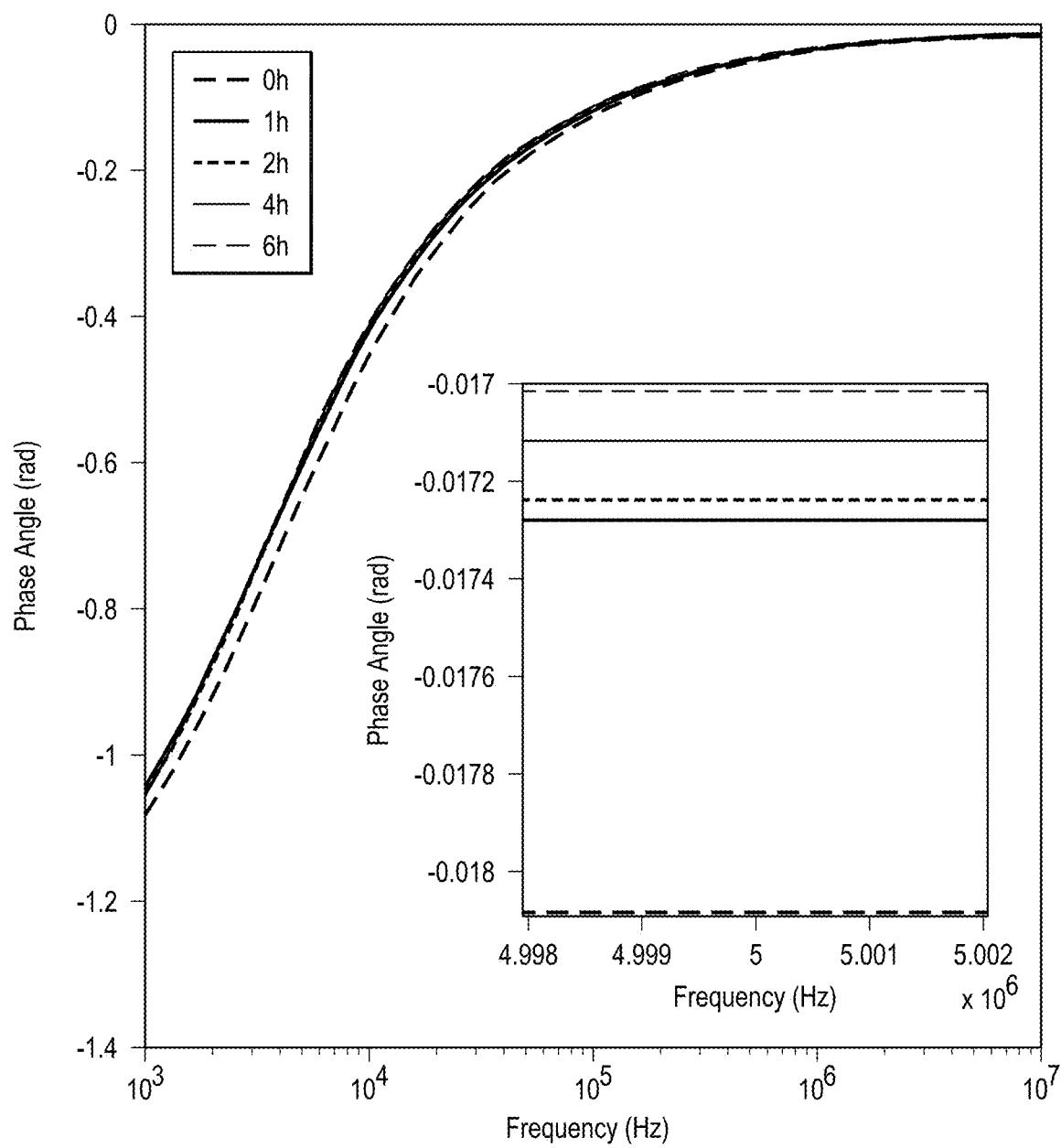

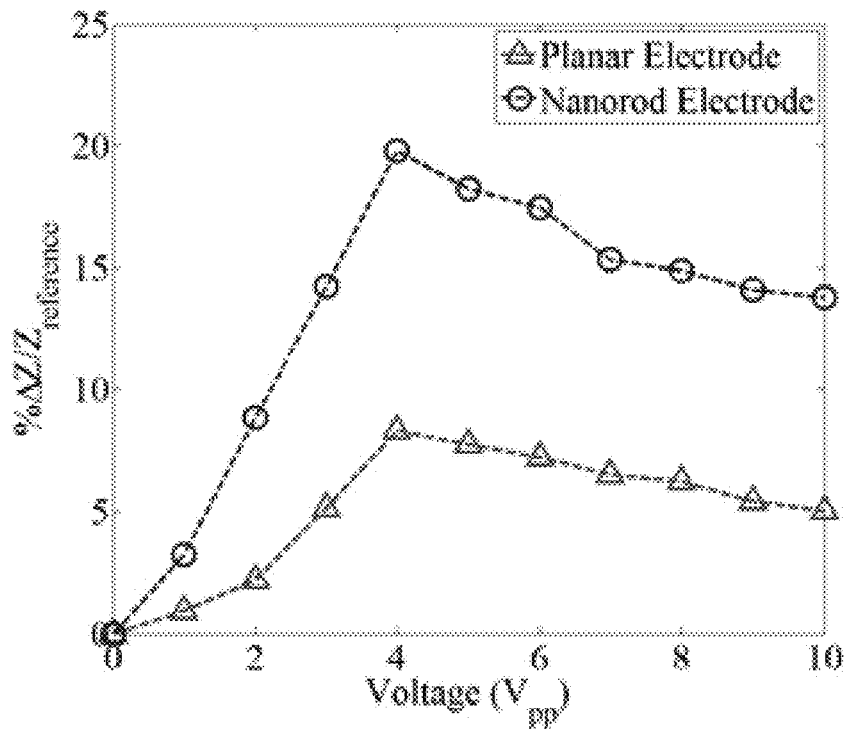
FIG. 10
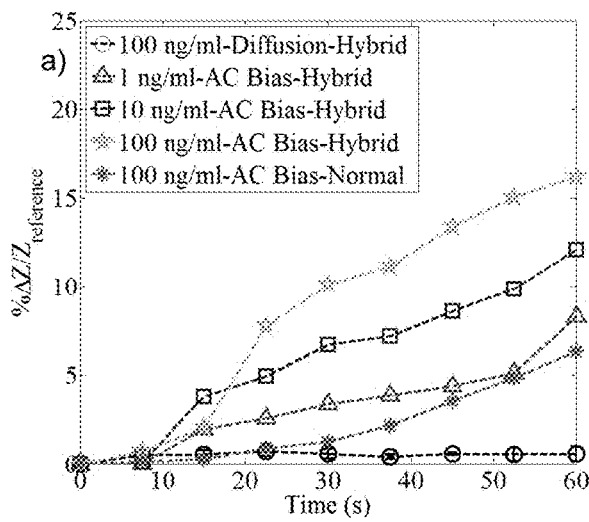
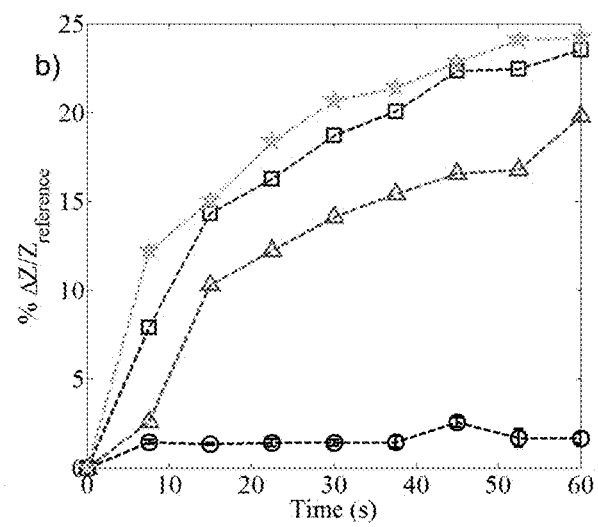
FIG. 11A  FIG. 11B

FIG. 12A
FIG. 12B
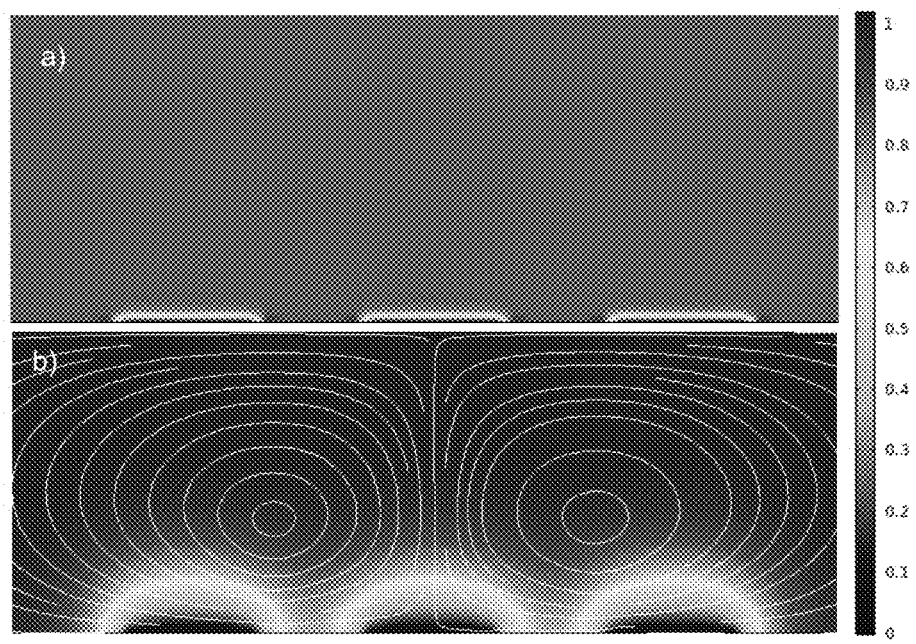
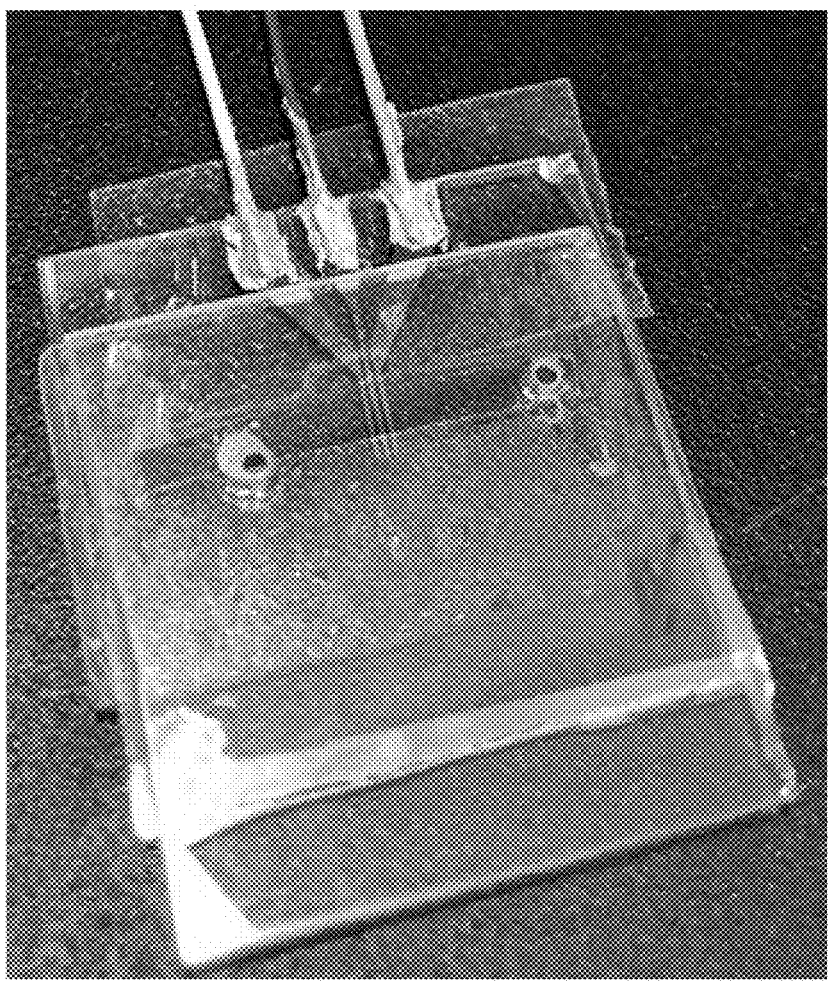
FIG. 13

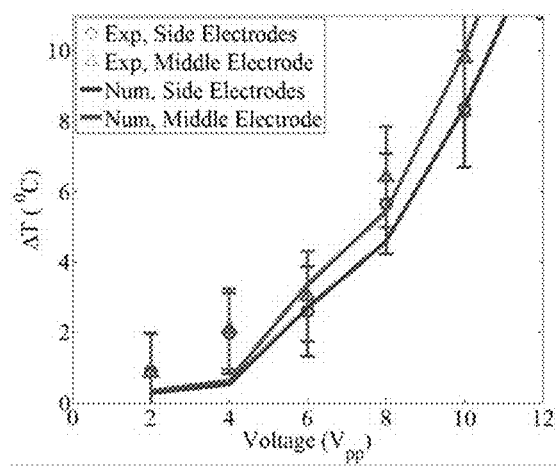
FIG. 21
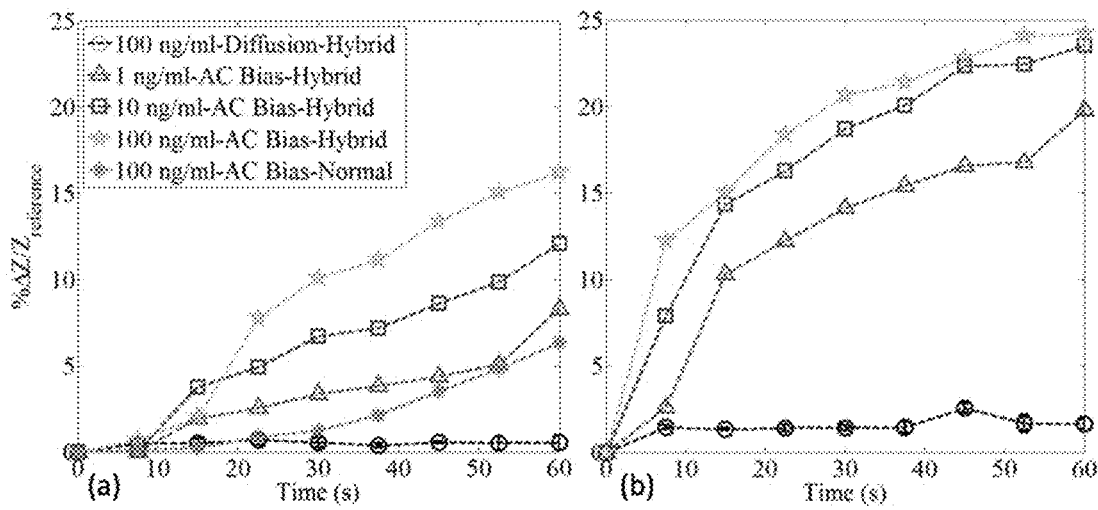
FIG. 22A FIG. 22B
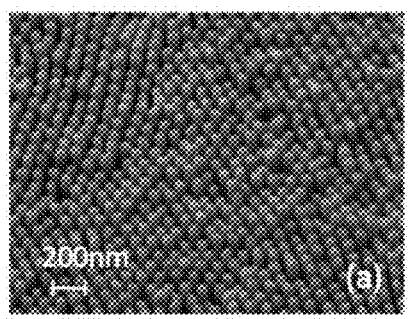 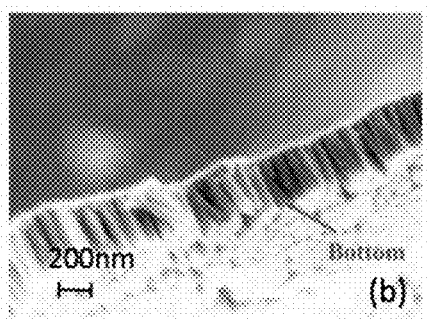
FIG. 23A FIG. 23B

SENSOR AND METHOD FOR DETECTING TARGET MOLECULES

CROSS-REFERENCE TO RELATED APPLICATIONS

This application is a divisional of U.S. patent application Ser. No. 17/171,829, filed Feb. 9, 2021, which claims priority to U.S. Provisional Application Ser. No. 62/972,386, filed Feb. 10, 2020, and U.S. Provisional Application Ser. No. 63/131,155 filed Dec. 28, 2020, the entire contents of which are incorporated herein by reference.

STATEMENT OF FEDERALLY FUNDED RESEARCH

Not applicable.

TECHNICAL FIELD OF THE INVENTION

The present invention relates in general to the field of sensors, and more particularly, to a sensor that detects one or more target molecules.

BACKGROUND OF THE INVENTION

Without limiting the scope of the invention, its background is described in connection with nanomolecule sensors.

In recent years, immunoassays have become powerful and versatile biomedical tools for the diagnosis of certain food toxins, environmental pollutants, or clinical diseases. Because of the specific binding between binding molecules and target molecules, immunoassays have been widely used to selectively bind biomolecules that are indicative of the presence of bacteria, viruses, or proteins. Conventional immunoassays such as the enzyme-linked immuno-sorbent assay (ELISA) is typically limited by their portability and high cost operation because they need to be elaborated fluorescent/enzyme tagging and sophisticated optical instruments. Impedance based immunosensors provide a low cost, portable, and sensitive detection for point of care applications. Their detection mechanism relies on binding molecules/target molecules reactions, which take place through diffusion-dominated transporting kinetics. Therefore, this mechanism is quite slow and reactions may not even occur, resulting in long reaction time (several hours), and low sensitivity. As a result, there is a need to develop highly sensitive detection platform for rapid screening and field-use applications ranging from proteomics to pathogen identification.

Microfluidic platforms are employed for point-of-care (POC) diagnosis purposes and also known as micro-total analysis systems (μ-TAS). μ-TAS has low cost, low power consumption, short analysis time, and use minute amounts of sample volumes. Most of the μ-TAS use physiological samples including urine, bile, cerebrospinal fluid, blood, salvia and biological buffers such as Lysogeny broth, Mueller Hinton broth, phosphate buffer saline, and Dulbecco's modified Eagle's medium where the conductivities of solutions vary from 0.4 to 1.8 S/m.

In the past few years, AC electro-kinetics/dynamics (ACEK-ACED) has been widely used to manipulate analytes to the detection region. All three major ACEK-ACED phenomena, dielectrophoresis (DEP), AC electroosmosis (ACEO) and AC electrothermal (ACET), can be used to induce directional biomolecular movement. DEP force is directly applied over particles, and is proportional to the size of target particles. Brownian motion effects increasingly interfere with dielectrophoretic action of nanometer sized particles, which results in weak attraction/repulsion forces. Moreover, DEP exists short-ranged typically within a few tens of microns away from the electrodes. ACEO phenomena typically occur at low ionic strength, and ACEO flow velocity has been observed to decrease significantly with increasing fluid's electrical conductivity and eventually drops to zero at above 0.1 S/m, making it unsuitable for most bioassays. Previous studies on AC electrokinetics revealed that for a biologically relevant high conductivity media such as phosphate buffer saline (PBS, $\sigma \sim 1.4$ S/m), ACET flow becomes predominant phenomenon inducing directional and long range convective vortices which can potentially drag the molecules to the middle of the electrodes' gap, then conveys them tangentially to the electrode surface for the interdigitated electrode pattern.

The interdigitated electrode array is a well-known geometric configuration for ACEK-ACED based microfluidic platforms, as it yields large electric field gradients even at small applied potentials. Moreover, the interdigitated electrode array present promising advantages in terms of low ohmic drop, fast establishment of steady-state, and increased signal to noise ratio. However, interdigitated planar surface electrodes fabricated by conventional photolithography methods have limited effective surface areas due to nano-sized surface roughness. 3D nanostructured electrodes can be introduced to enhance sensor sensitivity because it increases amount of the active binding cites and consequently, the absorbed volume of target molecules. Another fundamental limitation of usage of planar surface electrodes is the onset of electrode polarization (EP) that potentially overwhelms the impedance spectra at the low frequency range (<10 MHZ) depending on electrode size. Free ions in the solution accumulate towards the electrode/electrolyte interface, leading to a huge interfacial impedance and causing a high-applied voltage drop and decrease in the overall sensitivity and accuracy of the measurement. One of the most effective ways to minimize the EP is to maximize the electrode's effective surface area by generating nanostructures on the electrode surface. In the past few years, much effort has been devoted to generate well-ordered arrays of low-dimensional nanomaterials such as nanorods with high density and aspect ratio. The template assisted electrochemical deposition approach seems to be the most appropriate method for the fabrication of highly ordered, vertically aligned nanorod arrays in a fast and cost-effective fashion.

Hydrophilicity of the sensor surface is a prerequisite to creating high affinity binding molecule binding. In most of the cases, the surface of the whole hydrophilic substrate, where the sensors are held, is conjugated with binding molecules and it results in low binding cites on the sensor region because the binding molecules assay spreads out the surface due to the adhesive forces.

An example of an ACET fluidic circulatory pumping chip is described in Lang, Qi & Wu, Yanshuang & Ren, Yukun & Tao, Ye & Lei, Lei & Jiang, Hongyuan, (2015), AC Electrothermal Circulatory Pumping Chip for Cell Culture, ACS applied materials & interfaces, 7. 10.1021/acsami.5b08863, which is hereby incorporated by reference in its entirety.

SUMMARY OF THE INVENTION

Conventional immunosensor typically relies on passive diffusion dominated transport of analytes for binding reaction and hence, it is limited by low sensitivity and long detection times. As described herein, a simple and efficient impedance sensing method that can be utilized to overcome both sensitivity and diffusion limitation of immunosensors by incorporating the structural advantage of the enhanced surface area interdigitated electrodes (e.g., nanorods or other nanostructures, etc.) and the microstirring effect of AC electrothermal flow (ACET) with impedance spectroscopy. ACET flow induced by a biased AC electric field can rapidly convect the analyte onto enhanced surface area electrodes within a few seconds and enrich the amount of binding molecules because of excessive effective surface area. Numerical simulations were performed to investigate the effect of ACET flow on the biosensor performance. The results indicated that AC bias to the side electrodes can induce fast convective flow, which facilitates the transport of the target molecules to the binding region located at the middle as a floating electrode. Then, the change of impedance caused by the binding molecules-target molecules binding level at the sample/electrode interface were experimentally measured and quantified in real time using the impedance spectroscopy technique. It was observed that the impedance sensing method exhibited extremely fast response compared with those under no bias conditions. The measured impedance change can reach plateau in a minute, and the detection limit is able to achieve nanogram per milliliter (ng/ml). Compared to the conventional incubation method, the electrokinetics-enhanced method can be much faster in its reaction time, and the detection limit is reduced by 1 ng/ml. This sensor technology is demonstrated to be highly promising and reliable for rapid, sensitive and real time monitoring biomolecules in biologically relevant media such as blood, urine, salvia and etc. In another aspect, the apparatus is defined as further comprising 3, 4, 5, 6, 7, 8, 9, 10, 11, 12, 13, 14, 15, 16, 17, 18, 19, 20, or more fluid channels that extend from a central reservoir, wherein each channel comprises one or more sensors. In another aspect, the apparatus is defined as further comprising two or more sensors that detect two or more different modalities, wherein the modalities are selected from at least one of: electrical (impedance, capacitance, resistance) at different operating frequencies; optical fluorescence (amplitude) at different wavelengths; optical resonance (amplitude, phase) at different wavelengths; magnetic detection (magnitude and induced impedance); and/or acoustic waves (impedance, magnitude, phase) at different operating frequencies. In another aspect, the two or more modalities can be detected simultaneously without by selecting electromagnetic interferences frequencies/wavelengths at different spectrums, optically detect dyes or chromophores, electrically detecting contact with the sensors, opening or closing of ionic pores, current flow, impedance, resistivity, acoustic waves, resonance, a magnetic field or changes to the magnetic field.

In one embodiment, an apparatus for detecting one or more target molecules includes a hydrophobic substrate and a sensor. The sensor includes two or more electrodes disposed on the hydrophobic substrate and separated from one another by a gap, a plurality of nanostructures formed on or within an upper surface of each electrode, a plurality of binding molecules attached to the plurality of nanostructures, wherein the plurality of binding molecules are configured to bind with the one or more target molecules, and wherein the upper surface of each electrode and the plurality of nanostructures are hydrophilic. In one aspect, the hydrophobic substrate includes a glass, $SiO_2$, semiconductor or plastic material treated with a silylation reagent, each electrode is made of or coated with one or more metals or conductive organic polymers, and each nanostructure is made of or coated with the one or more metals or conductive organic polymers treated with ultraviolet light. In another aspect, the silylation reagent includes tridecafluorooctyltriethoxysilane, heptadecafluorodecyl trimethoxysilane, actadecyltrichlorosilane, n-octadecanethiol, self-assemble of alkanoic acid through a solution-immersion process, or hexamethyldisilazane (HMDS). In another aspect, the two or more electrodes comprise three interdigitated electrodes. In another aspect, a multiplexor is coupled to the two or more electrodes that selectively switches the two or more electrodes between inducing an alternating current electrothermal (ACET) flow and detecting the one or more target molecules. In another aspect, an alternating current power source and impedance analyzer are coupled to the multiplexor. In another aspect, a fluidic chamber is formed by one or more walls and a hydrophobic cover encloses at least a portion of the two or more electrodes, one or more fluidic ports are disposed within the hydrophobic cover and connected to the fluidic chamber, and wherein the two or more electrodes or a set of electrical conductors are connected to the two or more electrodes extend outside the fluidic chamber. In another aspect, the fluidic chamber is a microchannel loop. In another aspect, the sensor includes two or more sensors, wherein each sensor is selectively addressable. In another aspect, the two or more sensors include at least a first set of sensors and a second set of sensors. In another aspect, the plurality of binding molecules of the first set of sensors includes a plurality of first binding molecules configured to bind with one or more first target molecules, and the plurality of binding molecules of the second set of sensors include a plurality of second binding molecules configured to bind with one or more second target molecules. In another aspect, the first set of sensors detect the one or more target molecules while the second set of sensors simultaneously induce an alternating current electrothermal (ACET) flow, and the second set of sensors detect the one or more target molecules while the first set of sensors simultaneously induce the alternating current electrothermal (ACET) flow. In another aspect, an impedance measurement interface is connected to the sensor. In another aspect, a portable electronic device or a desktop device is coupled to the impedance measurement interface. In another aspect, the impedance measurement interface is integrated into the portable electronic device or the desktop device. In another aspect, the apparatus is packaged into a cartridge configured to interface with an electronic device. In another aspect, the target molecules are detected within a few seconds with a 1 ng/ml sensitivity. In another aspect, the apparatus is defined as further comprising 3, 4, 5, 6, 7, 8, 9, 10, 11, 12, 13, 14, 15, 16, 17, 18, 19, 20, or more fluid channels that extend from a central reservoir, wherein each channel comprises one or more sensors. In another aspect, the apparatus is defined as further comprising two or more sensors that detect two or more different modalities, wherein the modalities are selected from at least one of: electrical (impedance, capacitance, resistance) at different operating frequencies; optical fluorescence (amplitude) at different wavelengths; optical resonance (amplitude, phase) at different wavelengths; magnetic detection (magnitude and induced impedance); and/or acoustic waves (impedance, magnitude, phase) at different operating frequencies. In another aspect, the two or more modalities can be detected simultaneously without interferences by selecting electromagnetic frequencies/wavelengths at different spectrums, optically detect dyes or chromophores, electrically detecting contact with the sensors, opening or closing of ionic pores, current flow, impedance, resistivity, acoustic waves, resonance, a magnetic field or changes to the magnetic field.

In another embodiment, a method for fabricating an apparatus for detecting one or more target molecules includes providing a hydrophobic substrate, and fabricating a sensor by: forming two or more electrodes on the hydrophobic substrate, wherein the two or more electrodes are separated by a gap, forming a plurality of nanostructures on or within an upper surface of each electrode, attaching a plurality of binding molecules to the plurality of nanostructures, wherein the plurality of binding molecules are configured to bind with the one or more target molecules, and making the upper surface of each electrode and the plurality of nanostructures hydrophilic. In one aspect, providing the hydrophobic substrate includes providing a substrate comprising a glass, $SiO_2$, semiconductor or plastic material, and treating the substrate with a silylation reagent. In another aspect, the silylation reagent comprises tridecafluorooctyltriethoxysilane, heptadecafluorodecyl trimethoxysilane, actadecyltrichlorosilane, n-octadecanethiol, self-assemble of alkanoic acid through a solution-immersion process, or hexamethyldisilazane (HMDS). In another aspect, each electrode is made of or coated with one or more metals or conductive organic polymers, and each nanostructure is made of or coated with the one or more metals or conductive organic polymers treated with ultraviolet light. In another aspect, the two or more electrodes are three interdigitated electrodes. In another aspect, the method further includes coupling a multiplexor to the two or more electrodes that selectively switches the two or more electrodes between inducing an alternating current electrothermal (ACET) flow and detecting the one or more target molecules. In another aspect, the method further includes coupling an alternating current power source and impedance analyzer to the multiplexor. In another aspect, the method further includes forming a fluidic chamber with one or more walls and a hydrophobic cover enclosing at least a portion of the two or more electrodes, creating one or more fluidic ports within the hydrophobic cover and connected to the fluidic chamber, and wherein the two or more electrodes or a set of electrical conductors connected to the two or more electrodes extend outside the fluidic chamber. In another aspect, the fluidic chamber is a microchannel loop. In another aspect, the sensor includes two or more sensors, wherein each sensor is selectively addressable. In another aspect, the two or more sensors are at least a first set of sensors and a second set of sensors. In another aspect, the plurality of binding molecules of the first set of sensors include a plurality of first binding molecules configured to bind with one or more first target molecules, and the plurality of binding molecules of the second set of sensors include a plurality of second binding molecules configured to bind with one or more second target molecules. In another aspect, the first set of sensors detect the one or more target molecules while the second set of sensors simultaneously induce an alternating current electrothermal (ACET) flow, and the second set of sensors detect the one or more target molecules while the first set of sensors simultaneously induce the alternating current electrothermal (ACET) flow. In another aspect, the method further includes connecting an impedance measurement interface to the sensor. In another aspect, the method further includes coupling a portable electronic device or a desktop device to the impedance measurement interface. In another aspect, the impedance measurement interface is integrated into the portable electronic device or the desktop device. In another aspect, the method further includes packaging the apparatus into a cartridge configured to interface with an electronic device. In another aspect, the target molecules are detected within a few seconds with a 1 ng/ml sensitivity. In another aspect, a method for detecting one or more target molecules includes providing an apparatus that includes a fluidic chamber formed by a hydrophobic substrate, one or more walls and a hydrophobic cover, one or more fluidic ports disposed within the hydrophobic cover and connected to the fluidic chamber, and a sensor disposed within the fluidic chamber. The sensor includes two or more electrodes disposed on the hydrophobic substrate and separated from one another by a gap, a plurality of nanostructures formed on or within an upper surface of each electrode, a plurality of binding molecules attached to the plurality of nanostructures, wherein the plurality of binding molecules are configured to bind with the one or more target molecules, and wherein the upper surface of each electrode and the plurality of nanostructures are hydrophilic. The method also includes introducing a fluid into the fluidic chamber via the one or more fluidic ports, inducing an alternating current electrothermal (ACET) flow using the two or more electrodes and an alternating current power source coupled to the two or more electrodes, and detecting whether the one or more target molecules are present in the fluid by determining whether there is a change in an impedance of the two or more electrodes. In one aspect, the change in the impedance of the sensor is caused by the one or more target molecules bonding with the plurality of binding molecules. In another aspect, the two or more electrodes or a set of electrical conductors are connected to the two or more electrodes extend outside the fluidic chamber. In another aspect, the hydrophobic substrate includes a glass, $SiO_2$, semiconductor or plastic material treated with a silylation reagent, each electrode is made of or coated with one or more metals or conductive organic polymers, and each nanostructure is made of or coated with the one or more metals or conductive organic polymers treated with ultraviolet light. In another aspect, the silylation reagent comprises tridecafluorooctyltriethoxysilane, heptadecafluorodecyl trimethoxysilane, actadecyltrichlorosilane, n-octadecanethiol, self-assemble of alkanoic acid through a solution-immersion process, or hexamethyldisilazane (HMDS). In another aspect, the two or more electrodes include three interdigitated electrodes. In another aspect, the method further includes multiplexor coupled to the two or more electrodes that selectively switches the two or more electrodes between inducing an alternating current electrothermal (ACET) flow and detecting the one or more target molecules. In another aspect, the method further includes an impedance analyzer coupled to the multiplexor. In another aspect, the fluidic chamber includes a microchannel loop. In another aspect, the sensor includes two or more sensors, wherein each sensor is selectively addressable. In another aspect, the two or more sensors includes at least a first set of sensors and a second set of sensors. In another aspect, the plurality of binding molecules of the first set of sensors includes a plurality of first binding molecules configured to bind with one or more first target molecules, and the plurality of binding molecules of the second set of sensors include a plurality of second binding molecules configured to bind with one or more second target molecules. In another aspect, the first set of sensors detect the one or more target molecules while the second set of sensors simultaneously induce an alternating current electrothermal (ACET) flow, and the second set of sensors detect the one or more target molecules while the first set of sensors simultaneously induce the alternating current electrothermal (ACET) flow. In another aspect, the method further comprises an impedance measurement interface connected to the sensor. In another aspect, the method further includes coupling a portable electronic device or a desktop device to the impedance measurement interface. In another aspect, the impedance measurement interface is integrated into the portable electronic device or the desktop device. In another aspect, the apparatus is packaged into a cartridge configured to interface with an electronic device. In another aspect, the target molecules are detected within a few seconds with a 1 ng/ml sensitivity. In another aspect, the apparatus is defined as further comprising 3, 4, 5, 6, 7, 8, 9, 10, 11, 12, 13, 14, 15, 16, 17, 18, 19, 20, or more fluid channels that extend from a central reservoir, wherein each channel comprises one or more sensors. In another aspect, the apparatus is defined as further comprising two or more sensors that detect two or more different modalities, wherein the modalities are selected from at least one of: electrical (impedance, capacitance, resistance) at different operating frequencies; optical fluorescence (amplitude) at different wavelengths; optical resonance (amplitude, phase) at different wavelengths; magnetic detection (magnitude and induced impedance); and/or acoustic waves (impedance, magnitude, phase) at different operating frequencies. In another aspect, the two or more modalities can be detected simultaneously without interferences by selecting electromagnetic frequencies/wavelengths at different spectrums, optically detect dyes or chromophores, electrically detecting contact with the sensors, opening or closing of ionic pores, current flow, impedance, resistivity, acoustic waves, resonance, a magnetic field or changes to the magnetic field.

BRIEF DESCRIPTION OF THE DRAWINGS

For a more complete understanding of the features and advantages of the present invention, reference is now made to the detailed description of the invention along with the accompanying figures and in which:

FIGS. 1A-1K illustrate a process flow of fabricating interdigitated electrodes coated with nanorods in accordance with one embodiment of the present invention;

FIGS. 6A-6B are graphs showing impedance magnitude (FIG. 6A) and phase angle (FIG. 6B) in accordance with one embodiment of the present invention;

FIG. 7 is a plot of M factor was plotted for 1.4 S/m conductivity PBS solution from 1 kHz to 1 MHz in accordance with one embodiment of the present invention;

FIGS. 9A-9B are graphs showing impedance magnitude (FIG. 9A) and phase angle (FIG. 9B) for gold planar electrode fabricated HMDS for different antibody incubation time ranging from 0 to 6 hours in accordance with one embodiment of the present invention;

FIGS. 9C and 9D are graphs showing the impedance magnitude (FIG. 9C) and phase angle (FIG. 9D) for different antibody incubation time ranging from 0 to 6 hours in accordance with one embodiment of the present invention;

FIG. 10 is a graph showing the percentile normalized impedance change with different applied voltages for 1 nM concentration of target molecules mixed PBS solution for 60 second in accordance with one embodiment of the present invention;

FIGS. 11A-11B are graphs showing the percentile normalized impedance changes with time for different concentrations of target molecules measured by planar (FIG. 11A) and nanorod electrodes (FIG. 11B) in accordance with one embodiment of the present invention:

FIG. 12A-12B are plots showing simulation results of the binding process with an initial target concentration $c_0$=1 nM and target molecule concentration field for 0V (FIG. 10A) and 4V (FIG. 10B) applied AC bias amplitudes in accordance with one embodiment of the present invention;

FIG. 13 is an image of a device in accordance with one embodiment of the present invention;

(FIG. 19A) The schematic top view of the MAIRC system for measuring COVID-19 based human IgG, IgM and IgA antibodies on a chip. (FIG. 19B) Side view of one channel. Blood plasma is filled from the center and flows into the hydrophobic channel. Alternative current electrothermal flows guide the biomolecules onto the functionalized electrode and fluorescent-tag area to enhance binding. Electrode surfaces are coated with nanorods. Secondary antibodies enter from respective reservoirs at a delayed time to distinguish specifically IgG, IgM, and IgA immunoglobulins. (FIG. 19C) Signal and data flow chart for machine learning analysis and validation.

FIG. 21 is a graph that shows Local temperature changes by the ACET flow operation.

FIG. 22A shows the normalized impedance changes with time for different concentrations of target Bovine IgG. FIG. 22B shows nanorods-structured electrodes using three different concentrations of solution. (a) Test device. (b) Planar and (c) nanorod electrodes. In plots: Diffusion: without ACET flows. AC Bias: with ACET flows. Normal: flows in hydrophilic glass substrate. Hybrid: microchannels coated with hydrophobic HMDS and electrodes are hydrophilic. Concentration: IgG (ng) in FBS buffer (ml).

FIGS. 23A and 23B show: (FIG. 23A) Gold and (FIG. 23B) IrOx Nanorods on the electrode surfaces.

DETAILED DESCRIPTION OF THE INVENTION

Figure 1G:
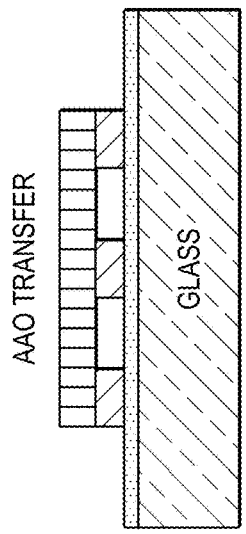
Figure 1H:
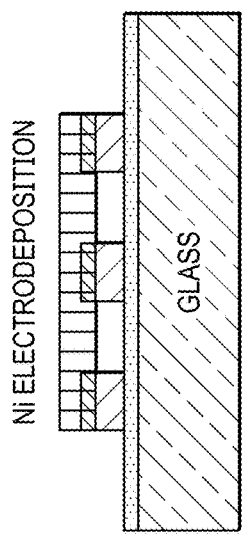
Figure 1I:
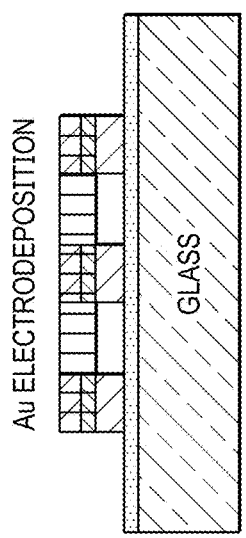
Figure 1J:
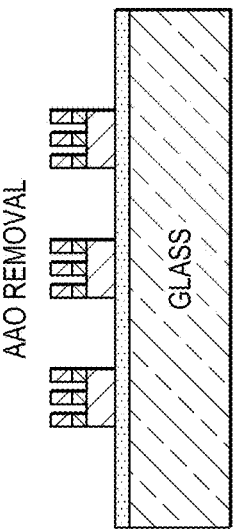

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

An effective impedance-based immunosensing strategy can significantly enhance the sensing speed and sensitivity by combining the structural advantages of enhanced surface are or nanostructured electrodes fabricated on a hydrophobic substrate while inducing ACET flow to accelerate transport of analyte toward the sensing region, where binding molecules were immobilized. The target molecule level was simultaneously quantified by measuring the interfacial impedance change rate because of specific binding of target molecules with binding molecules. Numerical simulations were used to verify that the ACET flow can assist the transport of the target molecules toward the sensor surface so that the overall binding process can be accelerated. Because of the electrokinetic enhancement, the sensitivity could be enhanced by at least one order of magnitude (compared to the ELISA kit) to reach a nanogram per milliliter (ng ml$^{-1}$) level, and the detection time could be reduced from several hours to a few seconds.

Example 1. Lab-On-a-Chip (LoC) Device for Rapid and Sensitive Detection of Nanomolecules As will be described in more detail below, various embodiments of the present invention provide a lab-on-a-chip (LoC) device that provides rapid and sensitive detection of nanomolecules. Some features of the LoC device may include, but are not limited to:

Fast detection with high sensitivity: Detection time of a few seconds with 1 ng/ml sensitivity.

Impedance based detection of multiple species on the same chip with no-cross-contamination.

Flexible with the used antibody, based on desired applications.

Microfluidic transport suitable for both low and high conductivity (physiological) buffers & fluids.

Hybrid surfaces reduce nonspecific binding on the walls and enable low friction to pump the fluid.

Nanostructured surfaces increase the binding surface area and allows wider frequency range for impedance measurements.

Uses cyclically pumped loop system with no external pumping components.

Impedance measurements and pumping is done at the same frequency to make electric circuitry simpler.

Can be developed as a hand held device or the LoC can be incorporated with a smart phone app through an impedance measurement interface, or it can be used in desktop equipment in doctors' offices, clinics, laboratories, etc.

Suitable for rapid health screening in remote areas, developing and underdeveloped countries.

General characteristics of various embodiments will now be described.

Hybrid Surfaces

Hybrid surfaces contains hydrophilic & hydrophobic characteristics. Lots of low surface energy materials can be selected to modify a hydrophilic surface, such as tridecafluorooctyltriethoxysilane, heptadecafluorodecyl trimethoxysilane, actadecyltrichlorosilane, n-octadecanethiol, self-assemble of alkanoic acid through a solution-immersion process, and hexamethyldisilazane (HMDS) as the silylation reagent. One unique aspect of aforementioned chemicals compared with many other passivation layers is that they can be used for many different wafer including glass, SiO$_2$, semiconductors or plastic materials to form a self-assembled monolayer and transform the hydrophilic surface to hydrophobic. They can also exhibit a surface roughness comparable to that observed for two dimensional materials supported by wafer. Besides that, they show highly biocompatible characteristics which makes them good candidates for biosensor applications. Other important aspects of having hybrid surfaces:

Low Friction on Walls

Hydrophobic surfaces develop hydrodynamic slippage at solid surfaces, as quantified by the slip length. Slip lengths on the order of a few tens of nanometers are typically reported for clean hydrophobic surfaces. Under realistic conditions, one may obtain a tenfold amplification of the bulk velocity just by increasing the slippage at the wall by a few nanometers. It provides three important aspects: (i) easy to pump; (ii) low power; and (iii) high speed.

Low Binding of the Binding Molecules on the Walls

The controlled immobilization of binding molecules on solid surfaces plays an important role in enhancing the sensitivity of sensors. The hydrophilicity of a surface causes a high number of binding molecules to bind or attach to that surface. When the sensor substrate and electrode surfaces are hydrophilic, they are conjugated with binding molecules, which results in low binding cites on the electrode surfaces because the binding molecules spread out over all the surfaces due to the adhesive forces. Therefore, localization of the binding molecules on the electrode surface is key parameter to fabricate a high performance immunosensor, which can be attained by using hybrid surfaces in which the electrode surface presents hydrophilic characteristics and the rest of the substrate remains hydrophobic. Lots of low surface energy materials were selected to modify a hydrophilic surface, such as tridecafluorooctyltriethoxysilane, heptadecafluorodecyl trimethoxysilane, actadecyltrichlorosilane, n-octadecanethiol, self-assemble of alkanoic acid through a solution-immersion process, and hexamethyldisilazane (HMDS) as the silylation reagent. Other materials, known or unknown, can be used to modify hydrophilic surfaces to become hydrophobic. A facile, inexpensive, and general approach is explored for the fabrication of transparent hydrophobic surface using HMDS. One unique aspect of HMDS compared with many other passivation layers is that it can react with surface of $SiO_2$ or glass to form a self-assembled monolayer and transform the hydrophilic surface to hydrophobic. HMDS can also exhibit a surface roughness comparable to that observed for two-dimensional materials supported by glass substrate. Furthermore, it shows highly biocompatible characteristics, which makes it a good candidate for biosensor applications. The binding molecules assay can be specifically pipetted on sensors, and it cannot move to the hydrophobic surfaces due to the surface forces. This feature provides two important features: (i) uses small amounts of binding molecules since they can be concentrated on the capture site (sensors); (ii) eliminates contamination of binding molecules from different biological molecules at the capture sites; and (iii) allows different binding molecules to be used in small areas.

Nanostructured Electrodes:

One of the most effective ways to minimize the EP and maximize the concentration of binding molecule molecules on a sensor region is to increase the electrode's effective surface area by generating complex nanostructures on the electrode surface. In the past few years, much effort has been devoted to generate well-ordered arrays of low-dimensional nanomaterials such as nanorods with high density and aspect ratio. The template assisted electrochemical deposition approach seems to be the most appropriate method for the fabrication of highly ordered, vertically aligned nanorod arrays in a fast and cost-effective fashion. Note that other enhanced surface area techniques can be used to increase surface area and reduce electrode polarization effects.

Nanostructured Electrodes Increase Surface Area for Binding Molecules

Planar surface electrodes fabricated by conventional photolithography methods have limited effective surface areas due to nano-sized surface roughness. 3D nanostructured electrodes can be introduced to enhance sensor sensitivity because it increases the active binding cites (sensor area) and consequently, the absorbed volume of target molecules.

Nanostructured electrodes allows wider frequency range for impedance measurements avoiding electrode polarization effects.

Another fundamental limitation of using planar surface electrodes is the onset of electrode polarization (EP) that potentially overwhelms the impedance spectra at the low frequency range (<1 MHz). Free ions in the solution accumulate towards the electrode/electrolyte interface, leading to a huge interfacial impedance and causing a high-applied voltage drop.

ACET/ACEO Based Micropumps

An effective method for increasing the sensitivity and at the same time decreasing the response time can be achieved by generating directional microflows inside the solution to transport the target molecules toward functionalized sites. Several methods, such as hydrodynamic, acoustic, and electrokinetics/dynamics mixing, have been employed to increase the reaction rate of binding molecules/target molecules binding. Studies on AC electrokinetics revealed that for a biologically relevant high conductivity media such as phosphate buffer saline (PBS, σ~1.4 S/m), ACET flow becomes predominant electrokinetic phenomenon inducing directional and long range convective vortices which can potentially drag the molecules to the sensor region. On the other hand, ACEO flow typically occur at low ionic strength (tap, river or lake water, etc.), and ACEO flow velocity has been observed to decrease significantly with increasing the fluid's electrical conductivity.

Micropumps are primarily used to transport minute amounts of fluid for a wide range of microfluidic applications including drug delivery, bio-fluid analysis, and microelectronics cooling. Micropumps are developed based on mechanical and non-mechanical driving methods to control the flow of different fluids in various devices and sensors for specific applications. The dependence of solid moving parts poses fabrication challenges and may have limited reliability of mechanical pumps. Non-mechanical pumps have several advantages over mechanical pumps such as high reliability (no moving parts), easy implementation into microfluidic devices, and continuous pumping of fluids. One such non-mechanical pumping method can utilize ACET/ACEO flow to transport fluids through microchannels. Coplanar asymmetric microelectrode pairs are used for ACET/ACEO micropumping, which are capable of operating at low voltages and are suitable for biofluidic applications.

ACET/ACEO Enhanced Microfluidic Impedance Sensing

Impedance based immune-biosensors provide a low cost, portable rapid and high sensitive detection for point of care applications. The used method integrates low voltage (<1 V) ACET/ACEO enhanced impedance measurement to achieve a single-step operation without any wash steps for clinical samples. With interdigitated microelectrodes as the sensor, the interfacial impedance of electrodes/sample solution is monitored at a fixed frequency AC signal. Specific binding at electrode surface is detectable through a change in the interfacial impedance. Impedance sensing is usually done at low voltages. Here the capacitance change is measured at a higher AC voltage, which will also induce ACET/ACEO effects simultaneously during measurement in the fluid around the electrodes. Therefore, the whole detection process is a one-step operation which does not require high skilled labors. Since the AC signal will accelerate the transport of analyte towards the electrodes for binding, the response time is usually less than one minute. So this method is much simpler and faster than commonly used ELISA procedure requiring multiple-wash/hour-long incubation. ACET/ACEO impedance sensing exhibits significant improvement in response time and detection sensitivity. Note that other sensor types can be used, such as surface plasma resonance (SPR).

Loop Systems

As will be described below, loop systems allow simultaneous measurement and pumping. This means that in a loop design, all the electrodes can be used to drive the flow and sense the impedance by using a multiplexer to switch between the driving the flow mode vs. impedance sensing mode for a split second. In fact, target molecule binding can be measured on one or more electrodes while other electrodes covered with other binding molecules keep on pumping. For example, the impedance measurement stage can be sequentially swept on each electrode to obtain the binding happening on the chip once every three to five seconds (if needed be). So, the test results can be monitored on the screen while a physiological solution is simultaneously circulated in the loop system. One of the embodiments described below uses 5 MHz AC files both to measure impedance and drive the flow. In simpler devices, the electrodes can be fixed to either drive the flow or sense the impedance.

For example, the microfluidic system can be designed to develop a robust electronic actuation system to perform a multiplexed protein assay. To carry out the multiplexed functionality, along a single microfluidic channel, an array of different types of binding molecules is patterned, where each element is targeting a specific target molecule. Below each element of the array, there is a pair of addressable asymmetric interdigitated electrodes. By selectively applying voltage at the terminals of each interdigitated electrode pair. ACET/ACEO flow can assist the transport of the target molecules toward the sensor surface so that the overall binding process can be accelerated.

Smart Phone or Desktop Interface with Proper Impedance Measurement Interface

A portable impedance analyzer can be connected to a smart phone to operate the microfluidic system, or single frequency detection can be made by a smart phone application. Likewise, the device can be used in desktop equipment in doctors' offices, clinics, laboratories, etc. After a physiological fluid is circulated in the loop system, the test result can be monitored on the screen. Note that a portable impedance analyzer is not required if the device includes an electronic circuit for ACET flow and impedance measurements.

One embodiment of the present invention will now be described.

Sensor Fabrication and Surface Modification.

A fabrication process of a sensor in accordance with one embodiment of the present invention is illustrated in FIGS. 1A-1K. Briefly, the microfluidic device was fabricated using a standard photolithography technique. Glass slides were cut into 2.5×2.5 cm$^2$ pieces using diamond cutter. The slides were cleaned in an ultrasonic bath (FB11201, Fisher Scientific) at 37 kHz and 25° C. sequentially in 1 M KOH, acetone, and isopropyl alcohol for 10 min, followed by rinsing with DI water. The slides were dried with Nitrogen and then, they were put in a conventional oven at 150° C. to fully evaporate water. Next, the surface of glass substrate was covered with HMDS to hydrophobize the glass surface (FIG. 1A). The glass slides were vertically dipped into a beaker which was filled with HMDS and acetone solution with 1:1 ratio for various durations. The beaker was left under a fume hood and then the substrates were withdrawn at a rate of 15 cm/min at room temperature)(20° C.

Figure 2:
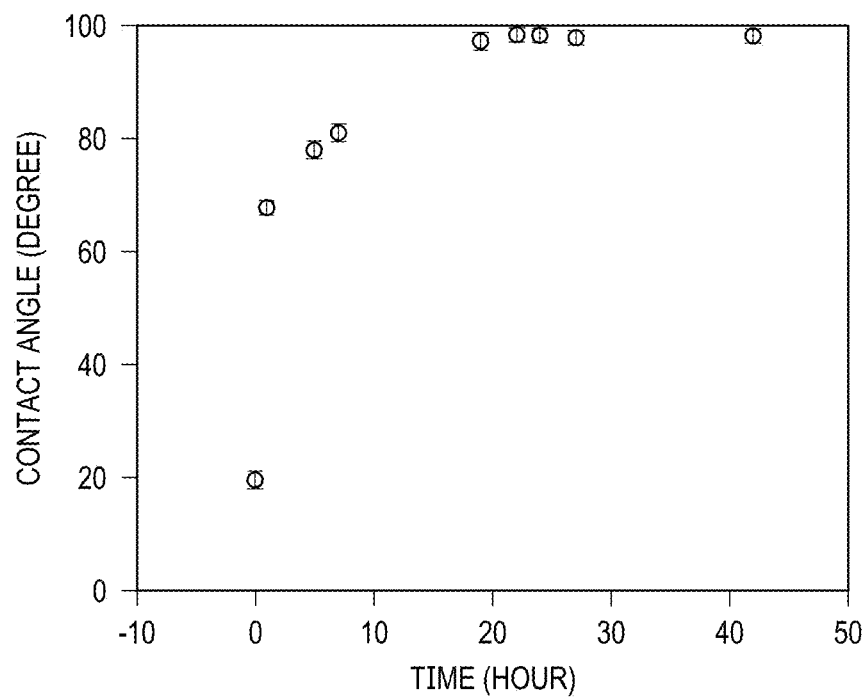
FIG. 2 is a plot showing the contact angle of water droplets on HMDS coated glass substrate in accordance with one embodiment of the present invention.

The variation of surface wettability depends on the dipping duration. Static water contact angles were measured with a high-resolution CCD camera (QImaging, Retiga 4000R) with Navita 12 objective lenses. Digital images were acquired using QCapture pro software (QImaging). The contact angle was measured from a sessile drop formed from a 10 µl water droplet via a syringe. Determination of contact angle was performed using the ImageJ software package with DropSnake plugin. Contact angle measurements were performed on at least five different locations on the sample surface and then averaged for statistics. The highest value of static contact angle was obtained when the treatment time was 42 h but the values are so similar to each other after 20 h surface treatment. FIG. 2 is a plot showing the contact angle of water droplets on HMDS coated glass substrate in accordance with one embodiment of the present invention. HMDS exposing time is varied from 0 minute to 42 hours. It was confirmed that the HMDS treatment has successfully introduced hydrophobic groups onto glass surface.

The positive photoresist (S1813) was spin coated on the HMDS covered glass substrates (FIG. 1B) using a two-step process with the following rotation speeds: 1000 rpm for 10 s and 4000 rpm for 30 s, with 300 rpm/s acceleration/deceleration. The substrate was soft baked at 115° C. for 1 min on a hot plate. In the next step (FIG. 1C), the substrate was exposed to UV light for 10 s at 110 mJ/cm2 using a mask aligner (Karl Suss, MJB3). As shown in FIG. 1D, the substrate was immersed into the developer for 17 s (MF-26A). After the substrate was gently washed with DI water and dried with Nitrogen, it was sputter-coated (EMS300TD, Emitech) first with chromium (120 mA-60 s) and later with gold (80 mA-120 s) (FIG. 1E). The substrate was immersed into a developer solution (PG remover) for lift-off process (FIG. 1F). Note that chromium and gold are representative examples of suitable materials that can be used. Other electrically conductive materials can be used, such as one or more metals (e.g., titanium, platinum, etc.) or conductive organic polymers.

Figure 3A:
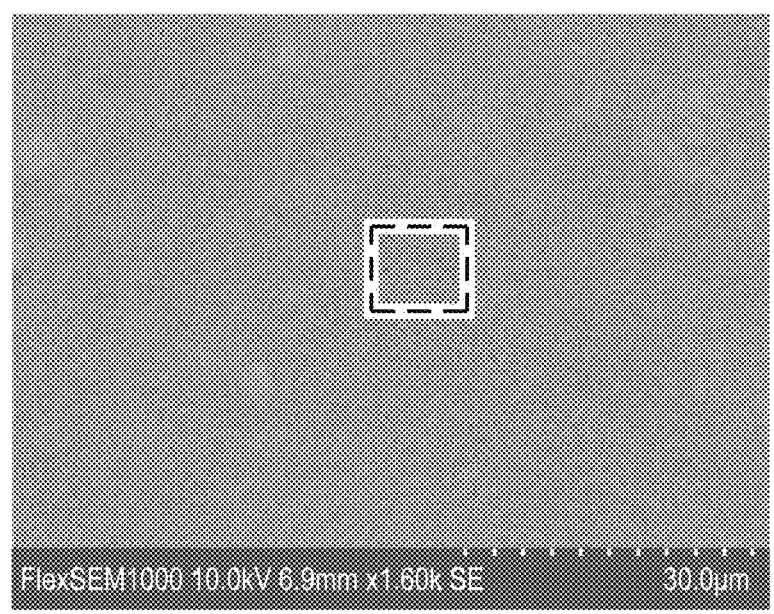
FIGS. 3A and 3B show the top view of the array of nanorods for different magnification in accordance with one embodiment of the present invention.
Figure 3B:
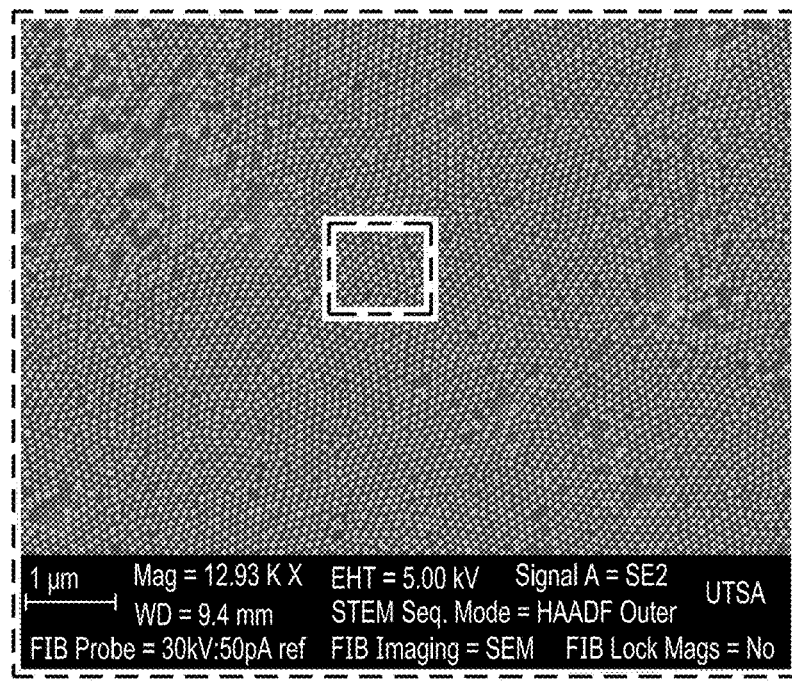
Figure 3C:
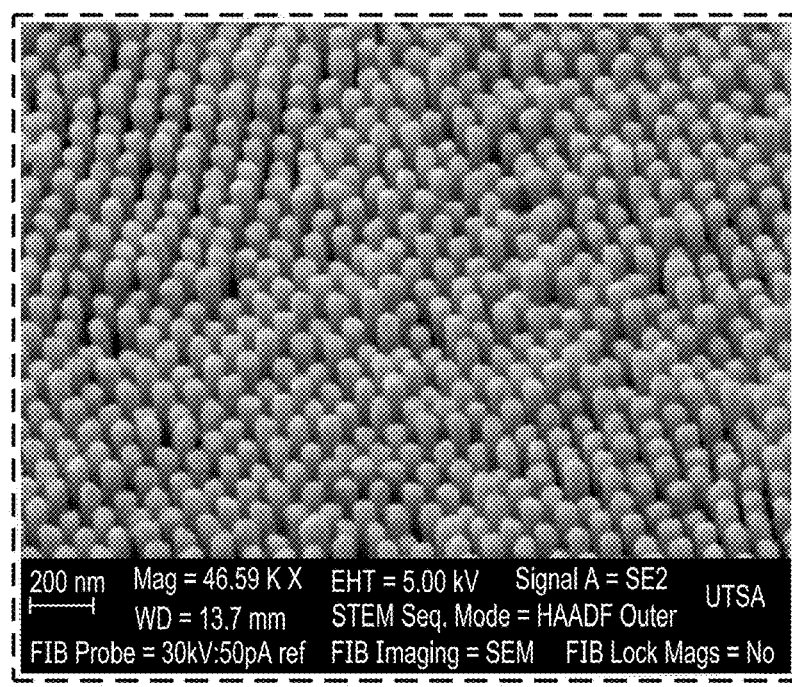
FIG. 3C shows a tilted view of the nanorods in accordance with one embodiment of the present invention.

The nanopatterning of the electrode surfaces was carried out using a template-assisted electrodeposition method. Here, a nanoporous anodic aluminum oxide (AAO) previously transferred to the gold surface (FIG. 1G) was used as a template during the electrodeposition of nickel and gold. Segmented composition nickel (50+12 nm)/gold (300+12 nm) nanorods were grown within the pores of the AAO template by electrodeposition using a CHI 660 electrochemical working station in a three-electrode configuration. The initial nickel segment was electrodeposited (FIG. 1H) using a nickel sulfamate solution (Technic Inc.) at a constant potential of −0.935 mV for 15 seconds. The sample was rinsed with deionized (DI) water and dried with Nitrogen gas. The gold segment of the nanorods was electrodeposited (FIG. 1I) using an Orotemp 24 RTU Rack (Technic Inc.) solution at a constant potential of −0.9 mV for 50 seconds. After electrochemical deposition, AAO template was removed (FIG. 1L) in a chromic-phosphoric acid solution at room temperature for 60 min. FIGS. 3A and 3B show the top view of the array of nanorods for different magnification, and FIG. 3C shows a tilted view of the nanorods. The deposition of an initial nickel segment is an essential step to improve the adhesion and coverage of the gold electrode with sensors, especially for detection in an aquatic medium. Note that the initial nickel segment is not required if improved adhesion and coverage of the gold electrode is not desired. Note that nickel and gold are representative examples of suitable materials that can be used. Other electrically conductive materials can be used, such as one or more metals or conductive organic polymers.

Figure 1K:
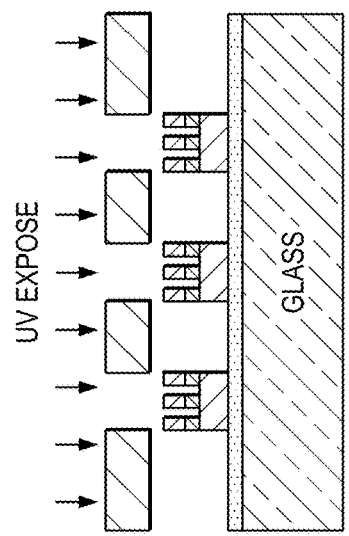
Figure 1L:
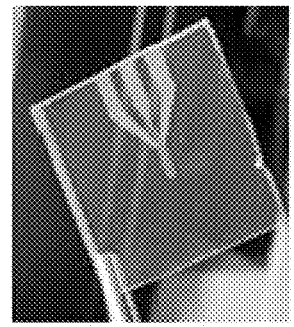
FIG. 1L is an image of interdigitated electrodes fabricated in accordance with the process shown in FIGS. 1A-1K.

Ultra Violet (UV) treatment is a good method for increasing the surface hydrophilicity without influencing the electrode microstructure characteristics. As shown in FIG. 1K, the HMDS part of the substrate was covered with a photomask to preserve its hydrophobic behavior, but the electrodes were exposed to UV for 10 minutes at the power of 110 mJ/cm$^2$. By doing this, binding molecules can be selectively coated on the electrode surface, which reduces the amount of target molecules potentially binding to the other surfaces. An image of the sensor fabricated with this process is shown in FIG. 1L. Note that the foregoing examples depicts three electrodes, but the process can be used for two electrode or more than three electrodes.

Electrodes with larger size were considered to be more amenable to inducing AC electrothermal convection and were successfully used to detect small molecules. Therefore, the device consists of three interdigitated electrodes with 200 µm width and 200 µm spacing. Natural convection effects are observed to grow larger as channel height increased. This is in accordance with scaling of Grashof number that is dependent on the cube of characteristic dimension, which is chamber height for this type of flow. The effect of natural convection is found negligible with chambers of 400 µm height and lesser. A rectangular portion of the tape was cut using a craft cutter to create a microchannel with 400 µm×10 mm×25 mm (height (H)×width (W)×length (L)) dimensions. The wires used for electrical connections were bonded using conductive silver epoxy (MG Chemicals). Another HMDS coated glass slide was used as a cover on the top of the microfluidic channel to increase the flow velocity in the presence of slippage at the wall and reduce the possibility of target molecules binding. A diamond drill bit drills the fluidic ports, and copper tapes are used for electrical connections.

Buffer Solution Preparation and Electrode Surface Functionalization.

PBS was prepared by 1:10 volume dilution of physiological strength stock solution ($\sigma$~1.4 S/m) with deionized water to obtain 1 mM phosphate buffer (pH 7.0) containing 0.05 v/v % Tween 20 (Fisher Scientific). The sensitivity of the microfluidic sensor was determined by measuring binding of goat anti-bovine IgG (H+L) (Jackson ImmunoResearch Laboratories Inc.) (Binding molecules) to bovine IgG whole molecules (Jackson ImmunoResearch Laboratories Inc.) (Target molecules). Bovine IgG whole molecules were immobilized on the electrodes prior to test. The microfluidic chip was incubated in an incubator for different time scale ranging from 1 h to 6 h. Different concentrations of the anti-bovine IgG antibody were loaded at concentrations ranging from 1 to 100 ng/ml in PBS.

Impedance Spectroscopy.

Figure 4:
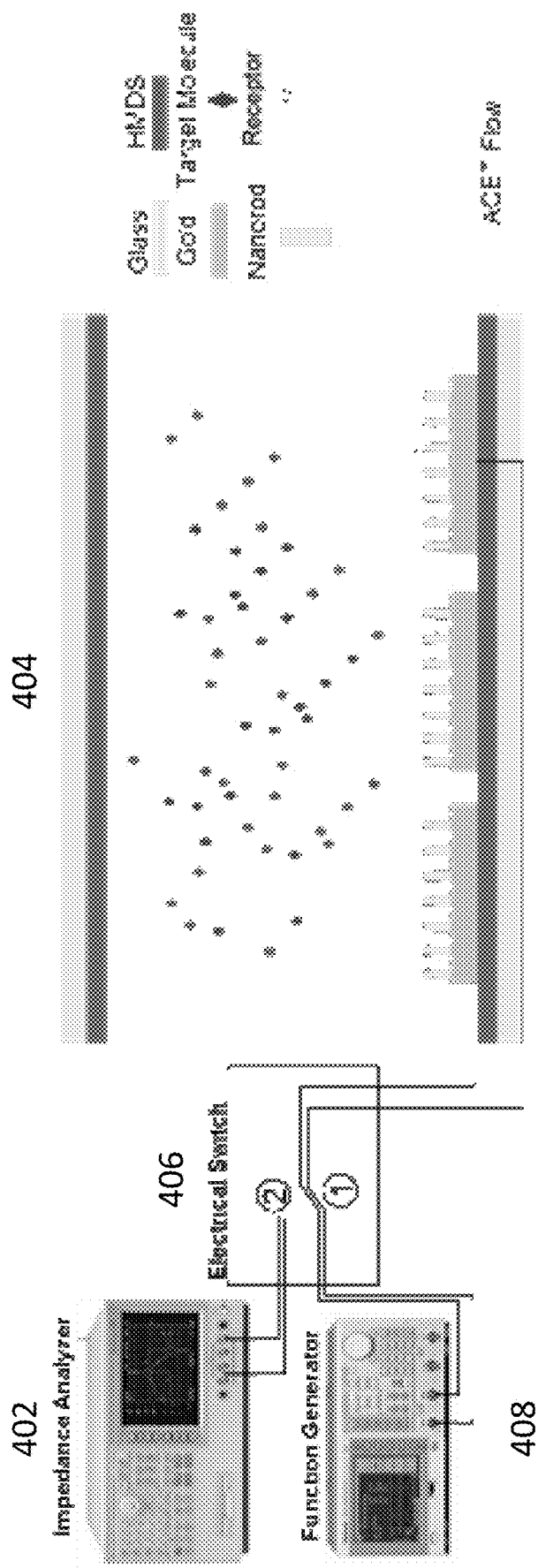
FIG. 4 is a schematic showing the configuration of the experimental setup in accordance with one embodiment of the present invention.

FIG. 4 is a schematic showing the configuration of the experimental setup. A high precision impedance analyzer (4194A, Agilent) 402 was used to measure the impedance spectrum of the microfluidic device 404 when it was filled both PBS and target molecules enriched PBS solution. The terminals of the side electrodes were connected to the low and high terminals of the impedance analyzer using a test fixture (HP 16047A) 406 in a four terminal configuration and the measurements were carried out at 401 discrete frequency points from 1 kHz to 10 MHz at 20 mV. The Faradic effects were neglected considering the operation conditions of impedance spectroscopy and electrode materials. The pumping action of the electrodes was controlled using a function generator 408 connected to the test fixture 406.

Figure 3D:
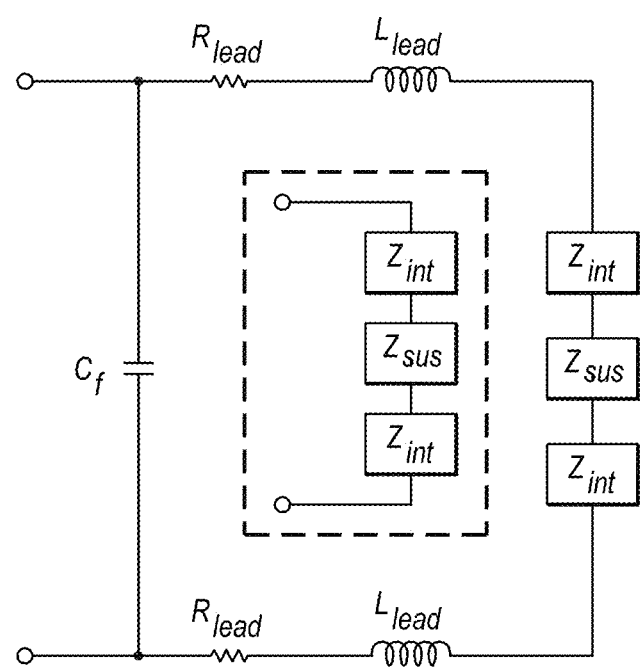
FIG. 3D is a diagram of the equivalent circuit model of microfluidic device in accordance with one embodiment of the present invention.

An equivalent circuit analysis was used to model the microfluidic device in terms of electrical components. The electrical components of a microfluidic section consist of interfacial impedance ($Z_{int}$) and target molecules enriched PBS suspension ($Z_{sus}$), respectively. These elements are in series with electrode lead resistance ($R_{lead}$) and inductance ($L_{lead}$). Finally, a parallel capacitance is added to account for stray (parasitic) ($C_f$) effects. The extraction of the resistances $R_{lead}$ (~3Ω), $L_{lead}$ (~$10^{-10}$ H), and $C_f$ using equivalent circuit analysis was explained in a previous article. After eliminating the aforementioned electrical components, the equivalent circuit modeled can be reduced to a simple form given in the FIG. 3D.

Theory and Numerical Simulations

A full understanding of the process requires an extensive model, which couples the physics of the electrostatics, the heat transfer, incompressible flow, and the adsorption kinetics. Under the assumption of quasi-electrostatic field (i.e., negligible magnetic field effect), the governing equations for electrode/electrolyte system are presented by Gauss' law and the charge conservation equation in the absence of convection current, $$\rho_q = \nabla \cdot (\varepsilon E) \tag{1a}$$

$$\frac{\partial \rho_q}{\partial t} + \nabla \cdot (\sigma E) = 0 \tag{1b}$$

$$\nabla \times E = 0 \tag{1c}$$

where $\rho_q$ is the space charge density, $\varepsilon$ is the permittivity of the fluid, E is the electric filed, $\sigma$ is the electrical conductivity of the medium. The generation of electric field causes temperature gradients, which lead to local variations in liquid permittivity and conductivity. The temperature distribution is determined by the energy equation excluding the convective term;

$$\rho_f c_{pf}\left(\frac{\partial T}{\partial t} + (u \cdot \nabla)T\right) = \nabla \cdot (k_f \nabla T) + \sigma|E|^2 \tag{2a}$$

$$\rho_s c_{ps}\left(\frac{\partial T}{\partial t}\right) = \nabla \cdot (k_s \nabla T) \tag{2b}$$

where $\rho_f$ is the fluid density, $c_{pf}$ is the fluid heat capacitance, $k_f$ is the fluid heat conductivity, $\rho_s$ is the solid density, $c_{ps}$ is the solid heat capacitance, $k_s$ is the solid heat conductivity, T is the temperature, u is the fluid velocity which is zero in the solid domain, and $\sigma|E|^2$ is the Joule heating term. Eq. 2a and 2b are solved for water and glass domains, respectively.

The fluid velocity field is governed by the Stokes equation for low Reynolds number flows.

$$\rho_m \frac{\partial u}{\partial t} = -\nabla P + \mu \nabla^2 u + F \tag{3a}$$

$$\nabla \cdot u = 0 \tag{3b}$$

where P is the pressure and F is the sum of the electrothermal force ($F_e$) and the buoyancy force ($F_b=\mu_m(T-T_0)\beta g$), where $T_0$ is the reference temperature, $\beta$ is the coefficient of thermal expansion, and g is gravity). The time averaged AC electrothermal force acting on an incompressible fluid media is given by, $$\langle F_E \rangle = \frac{1}{2}\varepsilon\left[(c_\varepsilon - c_\sigma)\frac{(\nabla T \cdot E)}{1 + (\omega \tau)^2}E - \frac{1}{2}c_\varepsilon \nabla T|E|^2\right] \tag{4}$$

Constants $c_\varepsilon$ and $c_\sigma$ are linear approximations of the temperature dependence of the electrical permittivity and conductivity, respectively, with $$c_\varepsilon = \frac{1}{\varepsilon}\frac{\partial \varepsilon}{\partial T} \approx -0.004° \text{ C.}^{-1} \text{ and } c_\sigma = \frac{1}{\sigma}\frac{\partial \sigma}{\partial T} \approx 0.02° \text{ C.}^{-1}.$$

The molecules moved toward the sensor reacts with the binding molecule ligand that is immobilized on the reaction surface. The binding reaction gives rise to a complex AB $$[A] + [B] \underset{k_{off}}{\overset{k_{on}}{\rightleftharpoons}} [AB] \quad (5)$$

where [A] is the target molecule concentration on the surface, [B] is the binding molecules concentration, and [AB] is the complex concentration. The association and dissociation rate constants are denoted by $k_{on}$ and $k_{off}$, respectively. It was assumed that the antibody B and the complex AB are immobilized on the surface. The binding reaction between the immobilized binding molecules and the target molecule is assumed to follow the first-order Langmuir adsorption model. The reaction rate is then described by the following chemical kinetics equation:

$$\frac{\partial [AB]}{\partial t} = k_{on}[A]([B_0] - [AB]) - k_{off}[AB] \quad (6)$$

where $[B_0]$ is the concentration of free binding molecules. The association and dissociation constants, that is, $k_{on}$ and $k_{off}$ for binding interactions are $10^7$ $M^{-1}s^{-1}$ and $2.6 \times 10^{-2} s^{-1}$, respectively. To obtain the analyte concentration [A] on the sensitive surface, the convection-diffusion analyte equation was resolved. A fraction of this analyte is convected toward the electrode. The transport equation of the analyte reads $$\frac{\partial [A]}{\partial t} + u \cdot \nabla [A] = D\nabla^2 [A] + R_i \quad (7)$$

where D ($D=6.5\times10^{-11} m^2/s$) is the IgG diffusion coefficient and $R_i$ denotes the reaction rate. Here, $R_i$ equals to zero because no reaction takes place in the fluid bulk.

The numerical model provides an insight of an ACET flow in a microchannel with a surface specific binding reaction on the electrodes. The geometrical parameters including the channel height and electrode dimensions were set the same as those used in the experimental setup. The length, width and depth of the microchannel are much larger than the electrodes' thickness and hence, the AC electrothermally-driven flow in a rectangular two-dimensional microchannel in the Cartesian coordinate system (x, y) was investigated. The numerical simulations were performed using COMSOL Multiphysics 5.4 that incorporates the electrical, thermal and Stokes flow. In the numerical model, a finer mesh is used near the electrodes to capture large gradients in electric, thermal and velocity fields. Sinusoidal wave form was applied to the side electrodes at a constant voltage with 180° phase difference. The middle electrode was kept as a floating electrode and the rest of the boundaries in domain 2 were set as an electrical insulating boundary condition. The temperature simulation domain includes the complete volume with constant temperature boundary conditions at the outer boundaries ($T_0=20°$ C.). For the velocity field, a no slip boundary condition is used on the solid boundaries. All the electrode surfaces were set as the binding region and the rest of the boundaries are considered as no-flux. All the constants used in numerical simulations are given in the Table below.

TABLE S-1

Constants used in numerical simulations.

| | |
|---|---|
| ε | $7.0832 \times 10^{-10}$ F/m |
| $c_\varepsilon$ | $-0.004°$ $C.^{-1}$ |
| $c_\sigma$ | $0.02°$ $C.^{-1}$ |
| $T_0$ | 293.15K |
| σ | 1.4 S/m |
| $k_f$ | 0.6 W/(mK) |
| $k_s$ | 1.05 W/(mK) |
| $c_{pf}$ | 4180 J/(kg · K) |
| $c_{ps}$ | 840 J/(kg · K) |
| $\rho_f$ | 1000 kg/m³ |
| $\rho_s$ | 2500 kg/m³ |

Detection Mechanism.

The detection mechanism is based on interrogating the impedance change at the interface between a sensor electrode and the sample solution due to binding reaction. FIG. 4 schematically shows the operation mechanism of this sensor in accordance with one embodiment of the present invention.

An AC voltage at a certain frequency was applied to the side electrodes using a function generator (Tektronix AFG3102) 408. ACET flow carries the target molecules to the immobilized binding molecules region and the impedance simultaneously increases due to the chemical binding. Then, impedance measurements were conducted by switching the input from function generator 408 to impedance analyzer 402 via an electrical switch 406 for every 7.5 seconds which gives 8 data points for every minute. First, the impedance analyzer 402 was operated at 401 discrete frequencies from 1 kHz to 10 MHz at 20 mV to determine the optimum frequency range for molecule detection. The impedance spectra of PBS solution was measured before and after binding molecules coating. When the optimum frequency was selected, impedance measurements were performed at a single frequency for the target molecule detection. Impedance of the system spontaneously increases until all the target molecules are trapped on the functionalized site of the electrodes. The binding of target molecules to the binding molecules can be obtained by calculating the normalized impedance change rate using the following equation, $$\Delta Z/Z_{reference} = (Z_{after\ binding} - Z_{before\ binding})/Z_{before\ binding} \quad (10)$$

The calculated $\Delta Z/Z_{reference}$ was used as an indication of target molecules binding to the antibody.

The Importance of Wettability of Impedance Measurements.

Figures 5A, 5B, 5C:
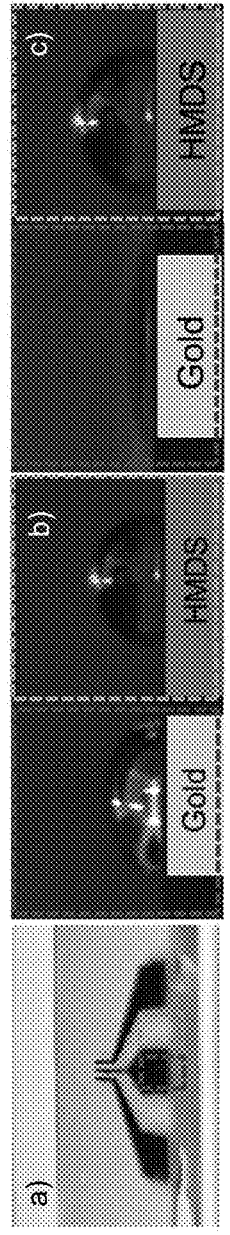
FIG. 5A is an image of interdigitated gold nanorod electrodes fabricated on HMDS coated glass substrate in accordance with one embodiment of the present invention.
FIGS. 5B-5C are images illustrating the wettability of hybrid surface (FIG. 5B) without and (FIG. 5C) with UV treatment in accordance with one embodiment of the present invention.

Wetting characteristics of the electrodes were investigated utilizing contact angle measurements. Static contact angle measurements were previously explained in reference to FIG. 2. The baseline glass surface shows a hydrophilic characteristic with a water contact angle of ~19±2.3°. After the surface of glass was treated for 24 h in HMDS solution, the surface became hydrophobic with a water contact angle of 99°±1.7. The change of the wettability characteristic is attributed to the chemistry of the HMDS. Bare glass is hydrophilic because of OH termination and water molecules can easily attach to the hydrogen of these silanol groups on the $SiO_2$ to form a thin water film but HMDS apparently screens water molecules. After coating the glass surface with HMDS for 24 h, gold interdigitated electrodes were fabricated using standard photolithography method described in the sensor fabrication part (FIG. 5A). The contact angle of a water droplet on the gold electrode was measured 77.87°±1.54° (FIG. 5B). After 10 minutes of selectively exposing a UV using mask aligner (MJB-3-Mask Aligner) at the power of 150 W, the water drop completely infiltrated into the electrode surface, indicating a marked surface transition from hydrophilicity to superhydrophilicity, resulting in a contact angle less than 10° for planar electrodes (FIG. 5C).

Vertically-oriented nanorods with the well-faceted (001) show superhydrophobic characteristics because of high surface roughness and low surface free energy, but the contact angle measurements could not be conducted due to the small actual electrode area (FIG. 1K). However, hydrophobic behavior of nanorod structured electrodes can be indirectly assessed by impedance measurements. The impedance measurements were performed with PBS for nanorod and planar electrodes. Each measurements was repeated at least three times, and the average impedance magnitude and phase angles were reported. The normalized standard deviation in all cases was obtained less than 1%. FIGS. 6A-6B show the Bode representation of the average impedance spectra of gold planar and nanorod structured electrodes.

At frequencies below 100 kHz, the impedance magnitude increased with decreasing frequency and the phase angle value shifted toward $-\pi/2$ radians. These changes are indicative of a transition toward capacitive charging processes at the electrode surface due to the EP effect. Since this phenomenon is mainly capacitive (C), it is proportional to the surface area of electrodes. As the effective surface area (A) of electrode increases with nanorod structures, the magnitude of the impedance should proportionally decrease ($Z\sim 1/C$) but the results were not consistent with the impedance behavior of a capacitor. Nanorod structured surfaces tended to be more hydrophobic, leading to poor reaction kinetics between the electrolyte and the electrode and weakening the ions transport. Bubble pockets can possibly shield the electrode surface which causes a high impedance value. After the nanorod electrode surface was exposed to UV, the impedance magnitude decreased drastically compared to that of measured with gold planar electrode and the usable frequency bandwidth expanded (FIGS. 6A-6B).

Selection of Sensor Operation Conditions

To ensure good electrical connections and proper impedance behaviors of the electrodes, prior to the ACET activation, the impedance spectra of the sensor filled with PBS were measured from 1 kHz to 10 MHz with an excitation voltage of 20 mV in the absence of target molecules. In the low frequency range, EP overshadowed the impedance spectra and this behavior was diminished about 5 MHz for gold planar electrodes and the impedance magnitude converges a frequency independent resistive plateau (FIGS. 6A-6B). Therefore, 5 MHz was selected as a critical frequency for the impedance based sensitivity measurements.

The ACET force expression can be expressed in terms of a directional parameter $$M\left(\left(\frac{T}{\sigma}\frac{\partial \sigma}{\partial T} - \frac{T}{\varepsilon}\frac{\partial \varepsilon}{\partial T}\right)\Big/\left(1+(\omega\tau)^2\right)\right) + 0.5 - \frac{T}{\varepsilon}\frac{\partial \varepsilon}{\partial T},$$

which is a function of frequency for a fixed type of liquid and temperature. The amplitude of ACET force can be predicted with M factor which remains constant until 10 MHz for 1.4 S/m PBS solution (FIG. 7) and therefore, the side electrodes were also excited at 5 MHz using the function generator. Moreover, most of the AC potential would be applied over the resistive fluid bulk which poses the highest AC electrothermal flow velocities.

According to the FIG. 7, at sufficiently high liquid conductivities the cross over frequency of ACET flow does not exist and the magnitude of the in the frequency and the magnitude of the factor becomes constant in the frequency range used here. For physiological conductivities (~1 S/m), the ACEF velocities are constant and effective at a high frequency range (~1 MHz), which can minimize electrolysis of the fluid.

The amplitude of applied potential cannot be increased arbitrarily, because higher voltages may lead to detachment of functionalized layer over electrode surface and lead to malfunction of the sensor due to the Joule heating effect. At high conductivities, temperatures beyond a few degrees (T>10° C.) are likely to occur under an applied AC potential of even a few volts. Therefore, the ACET-induced temperature must be measured prior to any electric field excitation to avoid unwanted effects and ensure that ACET is applicable and biologically safe for the required applications. The temperature rise at the electrodes induced by Joule heating is characterized using the TMX Scientific T Imager® thermal-reflectance (TR) imaging system. The TR technique measures the temperature rise of a reflective medium by detecting the temperature-induced surface reflectivity changes.

Briefly, calibration is first conducted to characterize the actual thermoreflectance behavior of the surface material. A known temperature change ($\Delta T_{cal.}$) is applied as the sample device is placed on a thermally controlled stage that can set the temperature to within 0.1 K. The device temperature in calibration is varied between two set temperatures (20° C. and 40° C.) and the reflectance change $\Delta R/R$ is collected using the camera. The coefficient of thermoreflectance is then calculated at each pixel (i, j) using $C_{TR}$ definition presented below:

$$C_{TR}(i, j) = \frac{1}{\Delta T_{Cal.}}\left(\frac{\Delta R}{R}(i, j)\right)_{Cal.}$$

During the activation runs, the reflectance change due to the Joule heating of the active device is measured. The unit change of reflectance ($\Delta R/R$) caused by the Joule-heating temperature rise is then extracted by averaging the two sets of unit intensity change maps ($\Delta I/I$) at each pixel in the ROI. The activation run is repeated, and the reflectance change maps are acquired at several voltage levels and frequencies to observe the Joule heating dependency on the different activation parameters.

To infer the actual temperature rise ($\Delta T_{Act.}$) distribution from the activation runs, the calibration field is combined with the activation reflectance maps at each pixel (i, j) according to the previous equation.

$$\Delta T_{Act.}(i, j) = \frac{1}{C_{TR}(i, j)}\left(\frac{\Delta R}{R}(i, j)\right)_{Act.}$$

Figure 8:
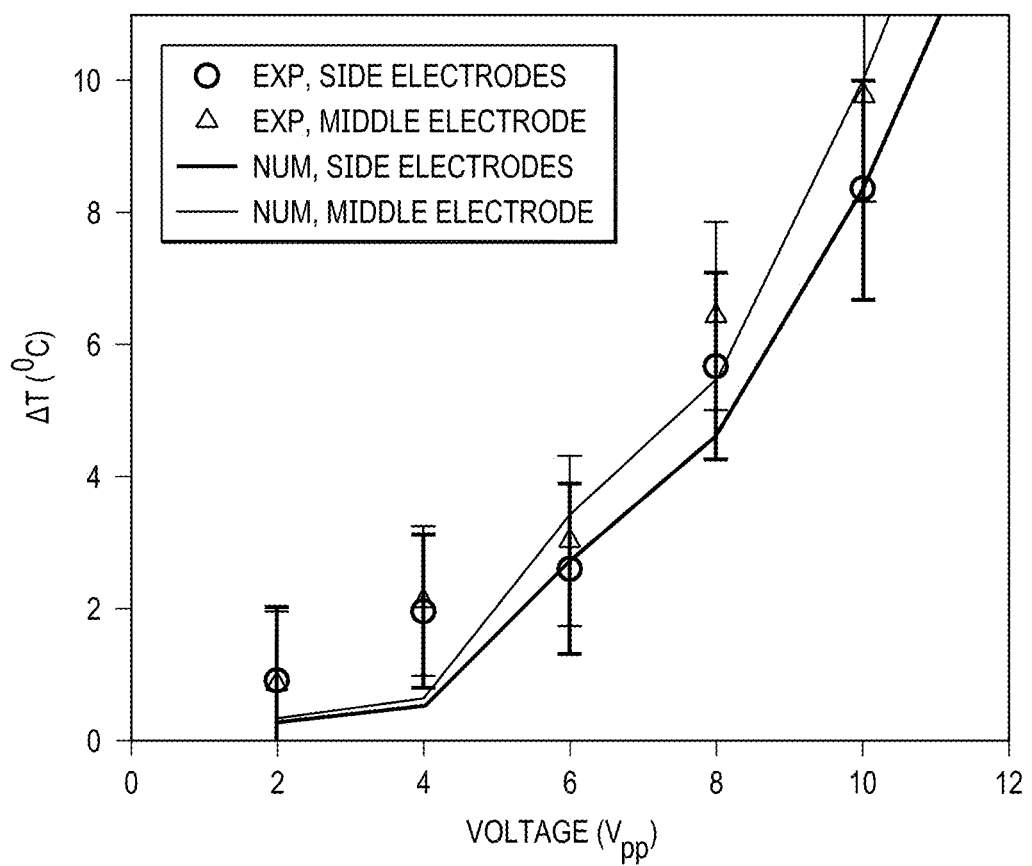
FIG. 8 is a plot of experimentally and numerically obtained average temperature rise on the side and middle electrodes as a function of the applied peak to peak voltage in accordance with one embodiment of the present invention.

FIG. 8 summarizes the average temperature rise on the side and middle electrodes as a function of applied voltage at 5 MHz. The standard deviation is for the set of 50 different measurements for an applied voltage. It is important to state that good agreement between the numerical model and experiments are due to the chosen applied frequency where EDL and stray capacitance effects are negligible, and hence, nearly the entire applied electrical field contributes to Joule heating. As expected from the Joule heating term, temperature increases with increasing activation voltage and hence, temperature rise was measured at different excitation voltages at 5 MHz. The results are given in FIG. 8 in supporting information. The temperature rise was obtained less than 10° C. up to 10 $V_{pp}$ and it considered safe for biomicrofluidic applications.

The Importance of Wettability for Surface Functionalization

The fast binding reactions was considered between the binding molecules and electrodes due to the hydrophilicity of UV exposed electrode surface. After the surface of electrodes was treated with the binding molecules inside an incubator, it was gently rinsed with PBS and 400 μm channel microfluidic channel was placed by centering the electrodes at the middle. Then, impedance measurements were conducted by pipetting PBS buffer in microfluidic channel.

Figure 9A:
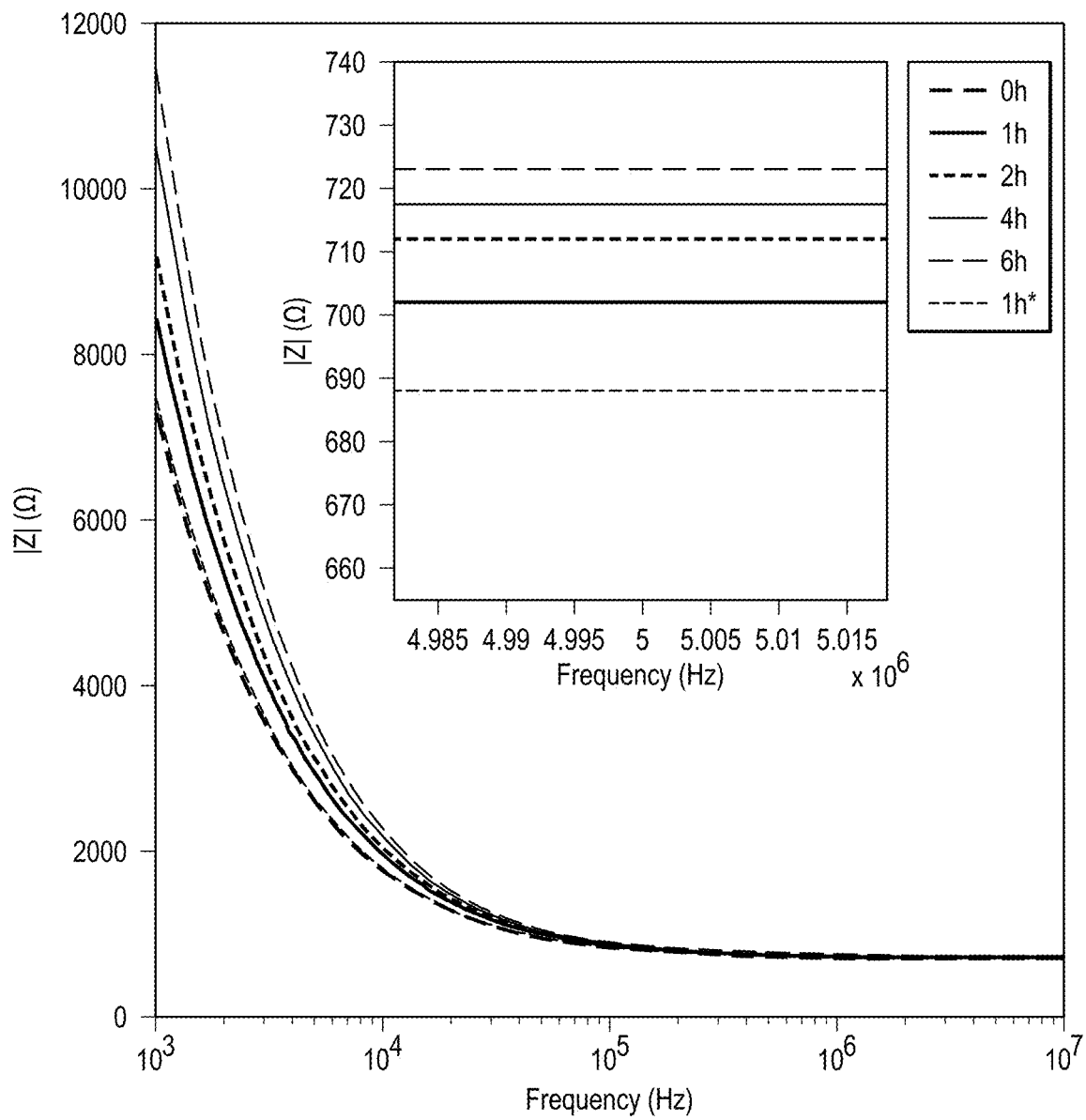

After 6 hours incubation process, impedance values have increased from 688.2Ω (0 hour) to 723.4Ω (6 hour) at 5 MHz for UV treated planar gold electrodes indicated adequate molecular immobilization on the electrode surface. The importance of hybrid surface to increase the concentration of binding molecules on the electrode surfaces was evaluated by comparing the impedance spectra measured with the gold planar electrode fabricated on hydrophilic glass surface. The impedance behavior of PBS measured with an hour incubated gold planar electrode fabricated on glass surface (1 h*) was obtained similar to that of measured with gold electrodes fabricated on HMDS at 0 hour incubation. Since the binding molecule's solution spread outs on glass surface, the concentration of binding molecules immobilized on electrode is obtained very low to induce a distinction on the impedance spectra. The impedance spectra is shown in FIGS. 9A and 9B. Then, the same measurements were repeated for UV treated gold nanorod structured electrodes fabricated on HMDS coated glass slides. The impedance spectra is shown in FIGS. 9C and 9D. First, the impedance magnitude increased from 605.6Ω to 945.1Ω at 5 MHz after an hour incubation with the binding molecules. The reason of this huge difference can be attributed the area of the active binding regions which is increased in the presence of nanorods. The second important point is the saturation of the attached binding molecules after an hour incubation since the impedance magnitude remained almost same for the case of 6 hour incubation.

Target Molecule Detection

The applied voltages range was determined using thermoreflectance method, but the effect of applied voltage on sensitivity must be investigated by sweeping the voltage from 1 to 10 Vpp.

The side electrodes were excited with 180° phase difference for 60 seconds and the results are depicted in FIG. 10 for UV treated planar and nanorod electrodes. In the absence of ACET flow, the microfluidic devices could not sense the target molecules in 60 seconds because of the diffusion based transport of molecules. On the other hand, they were transmitted onto the sensor region via the circulatory flow and trapped on the binding molecules. The normalized impedance change increased until the critical applied voltage (4 $V_{pp}$), then it drops to a certain value. The most possible reasons are low resident time of target molecules on binding molecules or the degradation of binding molecules due to temperature rise. Although, high applied voltages ($F_{ET} \sim V^4$) can induce fast convection flow, which facilitates the transport of the target molecules to the binding region, they could not find enough time to attach the immobilized binding molecules. Moreover temperature rise can potentially cause to damage the binding molecules which decrease the number of captured target molecules on the sensor. The specific binding reactions were conducted with Bovine IgG whole molecules by applying a 5 MHz AC voltage at $4V_{pp}$ for ACET flow, which increases the temperature 2° C. on the electrode surface (FIG. 8). 5 MHz AC signal at 20 mV was employed as the measuring signal. Six hours binding molecules incubated electrodes were used for these measurements. The normalized impedance change rates were plotted as a function of time in FIG. 11A for planar electrodes and FIG. 11B for nanorod structured electrodes using the three different concentration of solution.

As shown in FIGS. 11A-11B, the impedance of the solution without ACET flow remains constant around zero during the test, while that of ACET flow, impedance increases monotonically with time due to binding reaction. AC biasing led to a significant enhancement of the binding rate compared with that under unbiased conditions. For 100 ng/ml of target solution, the impedance change rate reached almost 15%/min and 25%/min using the planar and nanorod structured electrodes, respectively. The next set of experiments whether ACET driven impedance sensing is capable of quantitative measurement, in which target molecules was diluted with PBS and the concentration of solution was decreased to 1 ng/ml. The impedance change rates for various dilutions of target molecules are also demonstrated in FIGS. 11A-11B. As expected, when the sample became more diluted, the impedance change rate decreased at 1:100 dilution to 8%/min and 20%/min for planar and nanorod electrodes. The results in FIGS. 11A-11B demonstrate that ACET facilitated impedance method is a quantitative method within a range of low concentrations of target molecules.

The binding process was simulated using COMSOL Multiphysics for same size of device and concentration of molecules to better visualize the binding reaction. Unless analyte solution is moved towards the sensor surface using an external force, an analyte depletion zone of a few microns thickness can form next to the sensor surface in the solution which in turn can cause poor limit-of-detection and low sensitivity in biosensing (FIG. 12A). After the side electrodes are excited at $4V_{pp}$, the thickness of the depletion zone was significantly increased, which indicated that the depletion of the target molecules near the sensor surface was suppressed as a result of the continuous supply of the target molecules from the bulk electrolyte. In particular, the degree of suppression of the depletion zone was at a maximum exactly above the electrodes region. To clearly understand this phenomenon, the flow velocity field at $4V_{pp}$ AC bias was plotted in FIG. 12B. Owing to the micro-stirring effect of the induced vortex, the target molecules were continuously transported to the electrode region. These results indicate that interdigitated electrode array has an extremely suitable the selected geometry to take advantage of ACEF.

The electrodes described herein were planar and nanorod structured, conducting, interdigitated gold electrodes that are fabricated by standard photolithography and template assisted electrochemical deposition method. The binding process was aided by AC electrothermal effect that accelerates the transport of target molecules to the electrodes, where the surface was functionalized with binding molecules, and enhance the detection of target molecules by impedance sensing with simultaneous AC electrokinetic enrichment. These results demonstrate that the developed chip system allows the directed immobilization of proteins onto microelectrodes by dielectrophoresis without the need for any chemical modification and that protein function is preserved. FIG. 13 is an image of a device in accordance with one embodiment of the present invention.

Figure 14:
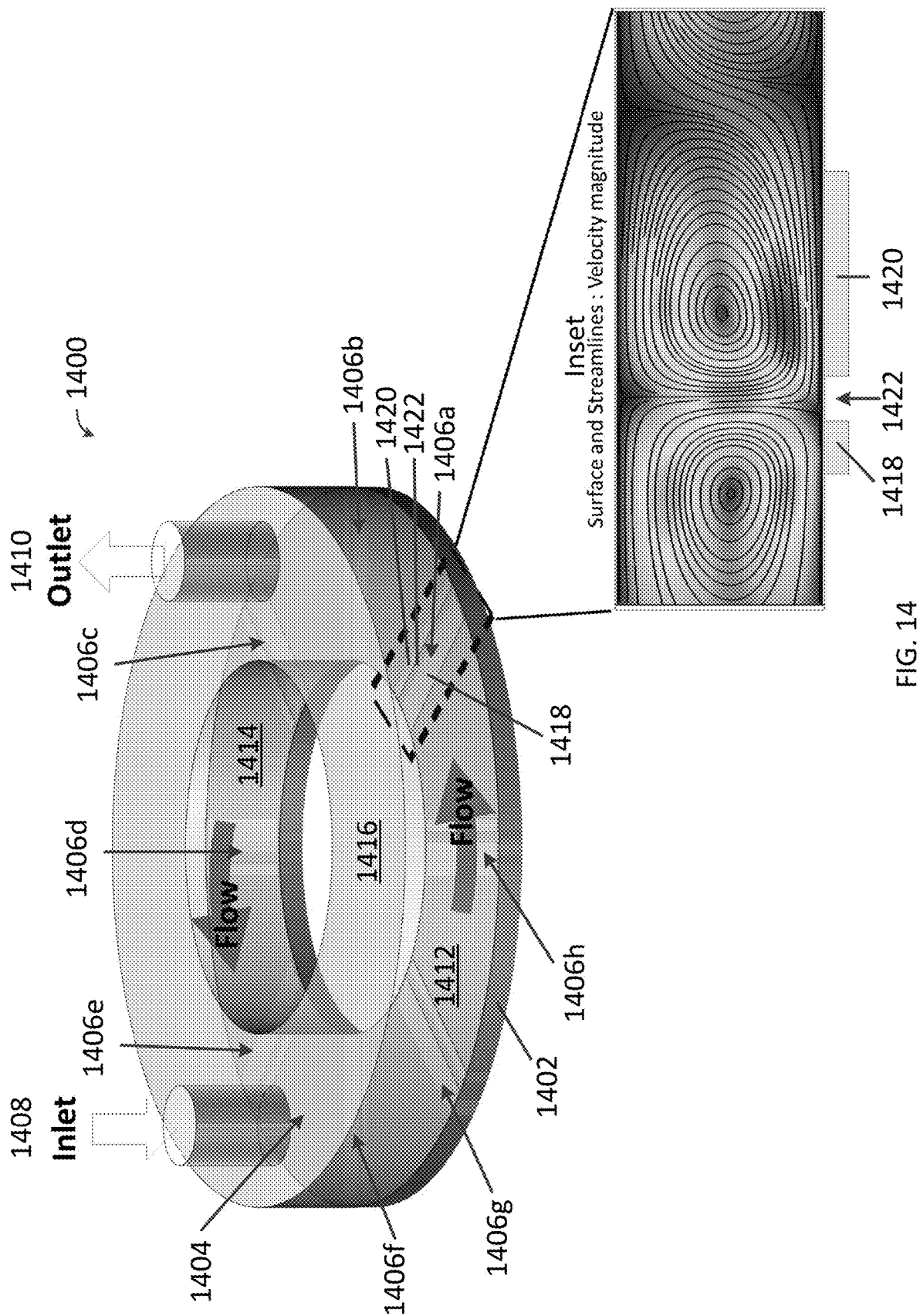
FIG. 14 illustrates a device for detecting one or more target molecules in accordance with another embodiment of the present invention.

FIG. 14 illustrates a device 1400 for detecting one or more target molecules in accordance with another embodiment of the present invention. The device 1400 has a hydrophobic substrate 1402, a fluidic chamber 1404, eight sensors 1406a-1406h, an inlet port 1408 and an outlet port 1410. Note that the fluidic chamber 1404 can be any desired shape (e.g., oval, elliptical, straight, etc.) and is not limited to the microchannel loop depicted. The walls 1412, 1414 and the cover 1416 are preferably hydrophobic. The inlet port 1408 and outlet port 1410 can simply be holes in the cover 1416 or passages of any desired shape. Moreover, the inlet port 1408 and outlet port 1410 can be or include connectors or interfaces to other devices, and may include covers, seals or valves. Each sensor 1406a-1406h includes two or more electrodes 1418, 1420 disposed on the hydrophobic substrate 1402 and separated from one another by a gap 1422. The device 1400 can include more or less than the eight sensors 1406a-1406h shown. The two or more electrodes 1418 and 1420 for each sensor 1406a-1406h can have different widths as shown or have similar widths depending on the design and performance specifications for the device 1400. As previously described, a plurality of nanostructures are formed on or within an upper surface of each electrode 1418, 1420, and a plurality of binding molecules are attached to the plurality of nanostructures. The plurality of binding molecules are configured to bind with the one or more target molecules. The upper surface of each electrode 1418, 1420 and the plurality of nanostructures are hydrophilic. The Inset illustrates the surface and streamlines showing the velocity magnitude when the electrodes 1418, 1420 are operating in the pumping mode. As previously discussed, each of the sensors 1406a-1406h can be operated in the pumping mode during one time period and the detection mode in a different time period. For example, sensors 1406a, 1406c, 1406e and 1406g can be operated in the pumping mode at the same time sensors 1406b, 1406d, 1406f and 1406h are operating in the sensor mode. Moreover, each sensor 1406a-1406h or groups of sensors 1406a-1406h can be configured to detect different target molecules.

Figure 15:
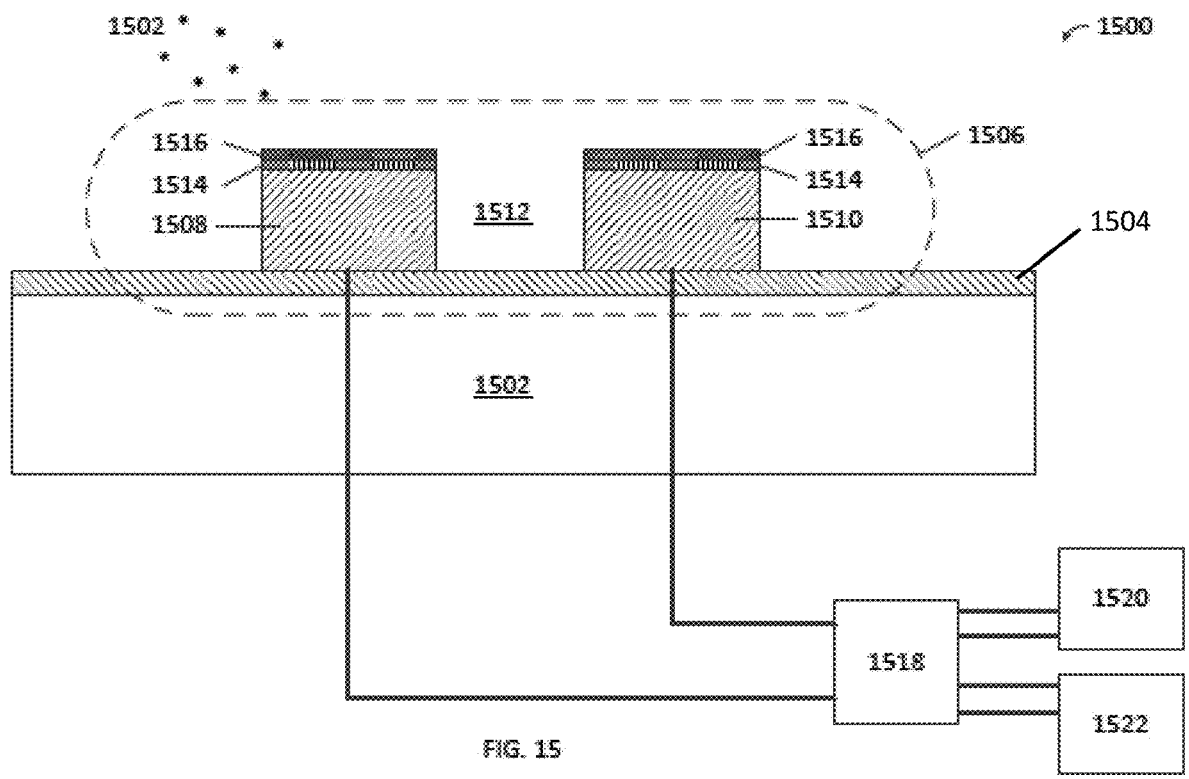
FIG. 15 is a block diagram of a device for detecting one or more target molecules in accordance with another embodiment of the present invention.

FIG. 15 is a block diagram of an apparatus 1500 for detecting one or more target molecules 1502 in accordance with another embodiment of the present invention. Note that the elements shown in the figure are not to scale. The apparatus 1500 includes a hydrophobic substrate 1504 and a sensor 1506. The sensor 1506 includes two or more electrodes 1508, 1510 disposed on the hydrophobic substrate 1504 and separated from one another by a gap 1512, a plurality of nanostructures 1514 formed on or within an upper surface of each electrode 1508, 1510, a plurality of binding molecules 1516 attached to the plurality of nanostructures 1514, wherein the plurality of binding molecules 1516 are configured to bind with the one or more target molecules 1502, and wherein the upper surface of each electrode 1508, 1510 and the plurality of nanostructures 1514 are hydrophilic. The electrical switch 1518 is connected to an impedance analyzer 1520 and a function generator 1522.

In one aspect, the hydrophobic substrate includes a glass, $SiO_2$, semiconductor or plastic material treated with a silylation reagent, each electrode is made of or coated with one or more metals or conductive organic polymers, and each nanostructure is made of or coated with the one or more metals or conductive organic polymers treated with ultraviolet light. In another aspect, the silylation reagent includes tridecafluorooctyltriethoxysilane, heptadecafluorodecyl trimethoxysilane, actadecyltrichlorosilane, n-octadecanethiol, self-assemble of alkanoic acid through a solution-immersion process, or hexamethyldisilazane (HMDS). In another aspect, the two or more electrodes comprise three interdigitated electrodes (see e.g., FIGS. 1L, 4). In another aspect, a multiplexor is coupled to the two or more electrodes that selectively switches the two or more electrodes between inducing an alternating current electrothermal (ACET) flow and detecting the one or more target molecules. In another aspect, an alternating current power source and impedance analyzer are coupled to the multiplexor. In another aspect, a fluidic chamber is formed by one or more walls and a hydrophobic cover encloses at least a portion of the two or more electrodes, one or more fluidic ports are disposed within the hydrophobic cover and connected to the fluidic chamber, and wherein the two or more electrodes or a set of electrical conductors are connected to the two or more electrodes extend outside the fluidic chamber. In another aspect, the fluidic chamber is a microchannel loop. In another aspect, the sensor includes two or more sensors, wherein each sensor is selectively addressable. In another aspect, the two or more sensors include at least a first set of sensors and a second set of sensors. In another aspect, the plurality of binding molecules of the first set of sensors include a plurality of first binding molecules configured to bind with one or more first target molecules, and the plurality of binding molecules of the second set of sensors include a plurality of second binding molecules configured to bind with one or more second target molecules. In another aspect, the first set of sensors detect the one or more target molecules while the second set of sensors simultaneously induce an alternating current electrothermal (ACET) flow, and the second set of sensors detect the one or more target molecules while the first set of sensors simultaneously induce the alternating current electrothermal (ACET) flow. In another aspect, an impedance measurement interface is connected to the sensor. In another aspect, a portable electronic device or a desktop device is coupled to the impedance measurement interface. In another aspect, the impedance measurement interface is integrated into the portable electronic device or the desktop device. In another aspect, the apparatus is packaged into a cartridge configured to interface with an electronic device. In another aspect, the target molecules are detected within a few seconds with a 1 ng/ml sensitivity.

Figure 16:
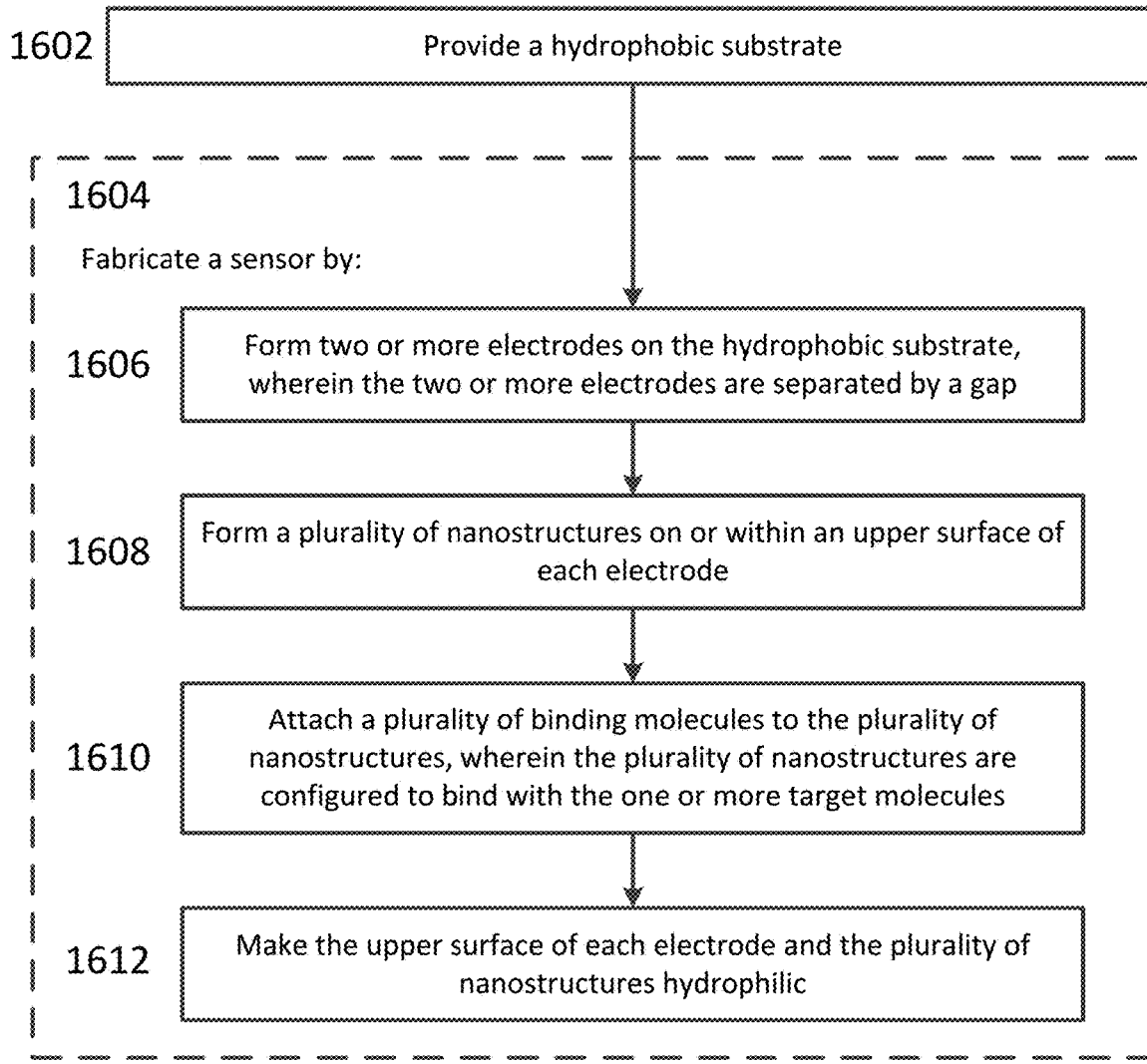
FIG. 16 is a flowchart of a method for fabricating an apparatus for detecting one or more target molecules in accordance with another embodiment of the present invention.

FIG. 16 is a flowchart of a method 1600 for fabricating an apparatus for detecting one or more target molecules in accordance with another embodiment of the present invention. The method 1600 includes providing a hydrophobic substrate in block 1602, and fabricating a sensor in block 1604 by: forming two or more electrodes on the hydrophobic substrate in block 1606, wherein the two or more electrodes are separated by a gap, forming a plurality of nanostructures on or within an upper surface of each electrode in block 1608, attaching a plurality of binding molecules to the plurality of nanostructures in block 1610, wherein the plurality of binding molecules are configured to bind with the one or more target molecules, and making the upper surface of each electrode and the plurality of nanostructures hydrophilic in block 1612.

In one aspect, providing the hydrophobic substrate includes providing a substrate comprising a glass, $SiO_2$, semiconductor or plastic material, and treating the substrate with a silylation reagent. In another aspect, the silylation reagent comprises tridecafluorooctyltriethoxysilane, heptadecafluorodecyl trimethoxysilane, actadecyltrichlorosilane, n-octadecanethiol, self-assemble of alkanoic acid through a solution-immersion process, or hexamethyldisilazane (HMDS). In another aspect, each electrode is made of or coated with one or more metals or conductive organic polymers, and each nanostructure is made of or coated with the one or more metals or conductive organic polymers treated with ultraviolet light. In another aspect, the two or more electrodes are three interdigitated electrodes. In another aspect, the method further includes coupling a multiplexor to the two or more electrodes that selectively switches the two or more electrodes between inducing an alternating current electrothermal (ACET) flow and detecting the one or more target molecules. In another aspect, the method further includes coupling an alternating current power source and impedance analyzer to the multiplexor. In another aspect, the method further includes forming a fluidic chamber with one or more walls and a hydrophobic cover enclosing at least a portion of the two or more electrodes, creating one or more fluidic ports within the hydrophobic cover and connected to the fluidic chamber, and wherein the two or more electrodes or a set of electrical conductors connected to the two or more electrodes extend outside the fluidic chamber. In another aspect, the fluidic chamber is a microchannel loop. In another aspect, the sensor includes two or more sensors, wherein each sensor is selectively addressable. In another aspect, the two or more sensors are at least a first set of sensors and a second set of sensors. In another aspect, the plurality of binding molecules of the first set of sensors includes a plurality of first binding molecules configured to bind with one or more first target molecules, and the plurality of binding molecules of the second set of sensors include a plurality of second binding molecules configured to bind with one or more second target molecules. In another aspect, the first set of sensors detect the one or more target molecules while the second set of sensors simultaneously induce an alternating current electrothermal (ACET) flow, and the second set of sensors detect the one or more target molecules while the first set of sensors simultaneously induce the alternating current electrothermal (ACET) flow. In another aspect, the method further includes connecting an impedance measurement interface to the sensor. In another aspect, the method further includes coupling a portable electronic device or a desktop device to the impedance measurement interface. In another aspect, the impedance measurement interface is integrated into the portable electronic device or the desktop device. In another aspect, the method further includes packaging the apparatus into a cartridge configured to interface with an electronic device. In another aspect, the target molecules are detected within a few seconds with a 1 ng/ml sensitivity.

Figure 17:
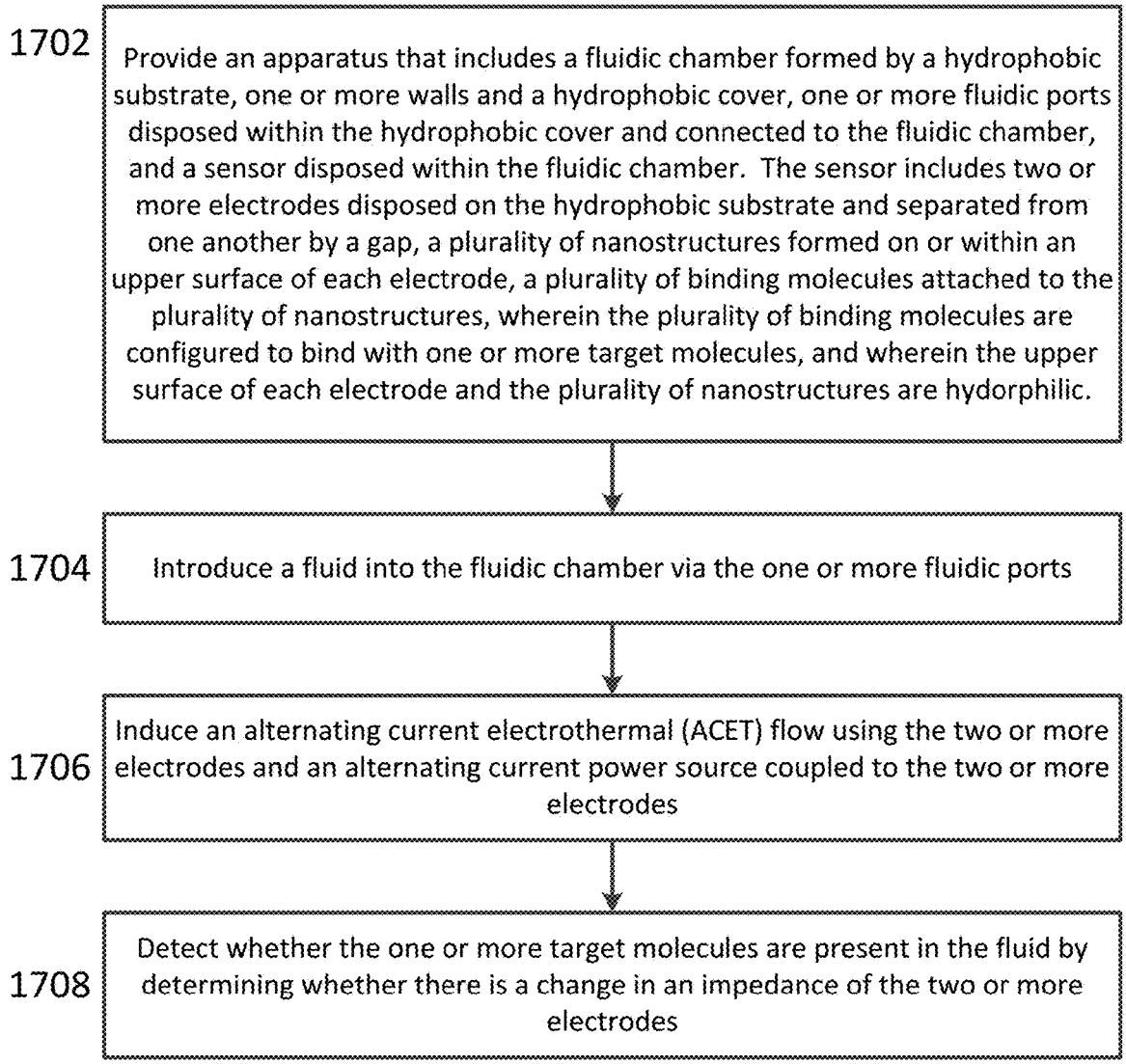
FIG. 17 is a flowchart of a method for detecting one or more target molecules in accordance with another embodiment of the present invention.

FIG. 17 is a flowchart of a method 1700 for detecting one or more target molecules in accordance with another embodiment of the present invention. The method 1700 includes providing an apparatus in block 1702 that includes a fluidic chamber formed by a hydrophobic substrate, one or more walls and a hydrophobic cover, one or more fluidic ports disposed within the hydrophobic cover and connected to the fluidic chamber, and a sensor disposed within the fluidic chamber. The sensor includes two or more electrodes disposed on the hydrophobic substrate and separated from one another by a gap, a plurality of nanostructures formed on or within an upper surface of each electrode, a plurality of binding molecules attached to the plurality of nanostructures, wherein the plurality of binding molecules are configured to bind with the one or more target molecules, and wherein the upper surface of each electrode and the plurality of nanostructures are hydrophilic. The method also includes introducing a fluid into the fluidic chamber via the one or more fluidic ports in block 1704, inducing an alternating current electrothermal (ACET) flow using the two or more electrodes and an alternating current power source coupled to the two or more electrodes in block 1706, and detecting whether the one or more target molecules are present in the fluid by determining whether there is a change in an impedance of the two or more electrodes in block 1708.

In one aspect, the change in the impedance of the sensor is caused by the one or more target molecules bonding with the plurality of binding molecules. In another aspect, the two or more electrodes or a set of electrical conductors are connected to the two or more electrodes extend outside the fluidic chamber. In another aspect, the hydrophobic substrate includes a glass, $SiO_2$, semiconductor or plastic material treated with a silylation reagent, each electrode is made of or coated with one or more metals or conductive organic polymers, and each nanostructure is made of or coated with the one or more metals or conductive organic polymers treated with ultraviolet light. In another aspect, the silylation reagent comprises tridecafluorooctyltriethoxysilane, heptadecafluorodecyl trimethoxysilane, actadecyltrichlorosilane, n-octadecanethiol, self-assemble of alkanoic acid through a solution-immersion process, or hexamethyldisilazane (HMDS). In another aspect, the two or more electrodes include three interdigitated electrodes. In another aspect, the method further includes multiplexor coupled to the two or more electrodes that selectively switches the two or more electrodes between inducing an alternating current electrothermal (ACET) flow and detecting the one or more target molecules. In another aspect, the method further includes an impedance analyzer coupled to the multiplexor. In another aspect, the fluidic chamber includes a microchannel loop. In another aspect, the sensor includes two or more sensors, wherein each sensor is selectively addressable. In another aspect, the two or more sensors includes at least a first set of sensors and a second set of sensors. In another aspect, the plurality of binding molecules of the first set of sensors include a plurality of first binding molecules configured to bind with one or more first target molecules, and the plurality of binding molecules of the second set of sensors include a plurality of second binding molecules configured to bind with one or more second target molecules. In another aspect, the first set of sensors detect the one or more target molecules while the second set of sensors simultaneously induce an alternating current electrothermal (ACET) flow, and the second set of sensors detect the one or more target molecules while the first set of sensors simultaneously induce the alternating current electrothermal (ACET) flow. In another aspect, the method further comprises an impedance measurement interface connected to the sensor. In another aspect, the method further includes coupling a portable electronic device or a desktop device to the impedance measurement interface. In another aspect, the impedance measurement interface is integrated into the portable electronic device or the desktop device. In another aspect, the apparatus is packaged into a cartridge configured to interface with an electronic device. In another aspect, the target molecules are detected within a few seconds with a 1 ng/ml sensitivity.

Example 2. Development of Multimodal and Multiplexing Point of Care Devices for Detection of Immune Response to COVID-19

Figure 18:
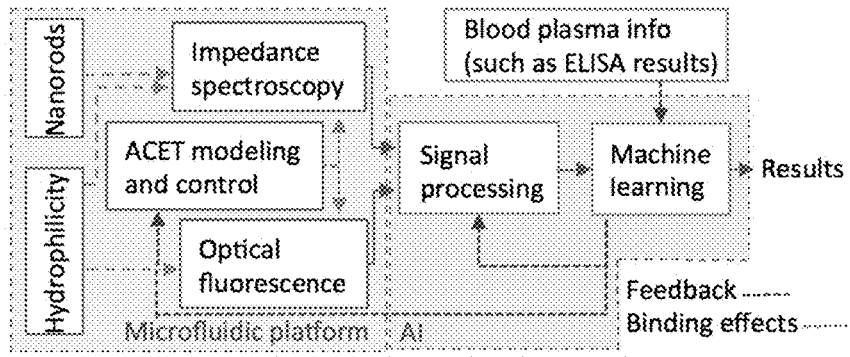
FIG. 18 System architecture for the dual-modality microfluidic multiplexed antibody sensor enhanced with deep neural network machine learning algorithms.

The goal in this example was to develop and integrate electrical impedance based and optical quantum-dot based sensing in a microfluidic platform, enhanced by alternative current electrothermal (ACET) flows, nanorods modified electrodes, and localized hydrophilic surfaces. Machine learning can be integrated to form an adaptive system to increase the sensing accuracy and reliability with capabilities to enhance ACET modeling and flow control parameters. The system can be applied for any immunoassay uses to detect viruses, bacteria or parasites, and biomarker detection for cardiac or cancer diseases. Using the present invention its now possible to detect, e.g., the COVID-19 human IgG, IgM, IgA immunoglobulins antibodies in a point-of-care system named Multiplexed Assay for the Immune Response to COVID-19 (MAIRC) to combat the current and upcoming pandemic crisis. FIG. 18 shows the overall system concept.

The present inventors developed the multiplexed microfluidic impedance spectrometry assays utilizing alternative current electrothermal (ACET) flow. They also integrated of fluorescent-based sensors in the multiplexed ACET microfluidic assays. They also developed a real-time, continuous machine learning signal processing to enhance accuracy and reliability. Finally, they integrated electrical and optical sensing modalities with algorithms to detect key COVID-19 human immunoglobin antibodies.

The integration of electrical impedance and fluorescent quantum-dot dual-modal sensing in a single multiplexed microfluidic platform is a platform for a new generation of immunoassays to detect biomarkers. In addition to the dual modalities in sensing, nanorods and selective hydrophilicity surface modification and ACET flow controls increase the sensitivity and specificity. The device architecture features quick, simple, reconfigurable, accurate point-of-care diagnosis capabilities, mass-manufacturability and analytical functions that are versatile, sensitive and specific for contagious pathogen detection including viruses, bacteria or parasites. The present invention includes: (1) microfluidic flow controls and modeling; (2) nano-scale surface modification; (3) selective functionalization on biomolecule-binding surfaces; (4) integration of electrodes and fluorescent quantum-dot in microfluidic channels; (5) sensitivity and specificity for detecting immunoglobins with primary and secondary antibodies; and (6) machine learning signal processing to validate signals for decision making. The invention directly advances technologies, including: (a) integrating sensing and control electronics and optics onto a single microfluidic platform; (b) signal processing and decision making from multi-sensor data sets; and (c) establishing a new type of instruments for multi-modal antibody detection. This integrative device and methods enable healthcare institutes to implement fast responses and win battles over novel viruses such as coronaviruses, and other contagious diseases.

The COVID-19 pandemic is ravaging communities and crippling the world economy. Many nations and states imposed "stay-at-home" orders for the general public. Health officials are uncertain about when to lift these orders and how soon daily life can return to normal. An important aspect of this decision depends on determining the spread of COVID-19 infection, which requires extensive and accurate testing of the population. People who were exposed to COVID-19 and built immunity to it can perhaps return to their jobs/schools. Although the immunity period for people who built antibodies to COVID-19 are not yet concluded, this proposition is logical based on experiences gained from previous infection cases. For the COVID-19 specific human antibodies, detections of IgG, IgM and IgA are preferred [1], [2].

The same scenarios also apply for other viral epidemics such as SARS (Severe acute respiratory syndrome, 2002-04 outbreak), MERS (Middle East respiratory syndrome, since 2012) and H1N1 (Influenza A virus subtype H1N1, since 2009) [3]-[9] which can potentially create another pandemic. Seasonal viral transmission between people such as Influenza and Enterovirus are also threats [10]-[14]. Contagious diseases caused by bacteria such as Tuberculosis (TB) and by parasites such as Malaria are also life threatening and can quickly spread among global travelers. A person infected by TB may not have any symptoms until it becomes too late. Although TB is treatable, patients can develop drug-resistant TB if the treatment is not administered early. According to CDC records, up to 13 million Americans are living with latent TB infection. Malaria with about 228 million cases worldwide impacts more to children under 5 years old liable for more than 272,000 deaths. Although medicines for diagnosis and treatments have advanced greatly, these diseases have not been eradicated because of their spreading means and multiple species.

For a viral pandemic, testing large portions of the population requires the development of quantifiable, accurate, fast, and inexpensive diagnostic methods based on detection of human IgG, IgM and IgA antibodies, which do not currently exist except by laboratory equipment. The gold standard for antibody detection is the enzyme-linked immuno-sorbent assay (ELISA) [16]-[20], which has high costs and is hard to scale. Its detection mechanism relies on antigen-antibody interaction, which takes place in the wells of microtiter plate and requires a colorimetric reader to interpret the result. Therefore, the detection mechanism is quite slow and more blood plasma samples with specific reagents for testing are required. The optical detection designed for automatic processes in the instrument requires costly electronics and sample calibration, while different antibodies cannot be tested in the same well simultaneously. High-resolution electrophoresis equipment, which are commercially available, provides accurate reading but requires costly machines [21], [22]. Developed for rapid responses to the pandemic, unfortunately, the lateral flow assays [23], exhibit low sensitivity and specificity due to the passive flow mechanism [25]. [26]. They cannot test multiple antibodies using the same sample either. Several studies have shown that they cannot be reliably used for determining the spread of COVID-19 infection, which still requires the more reliable RT-PCR (reverse transcription polymerase chain reaction) tests to validate mRNA [27]-[30].

Figures 19A, 19B, 19C:
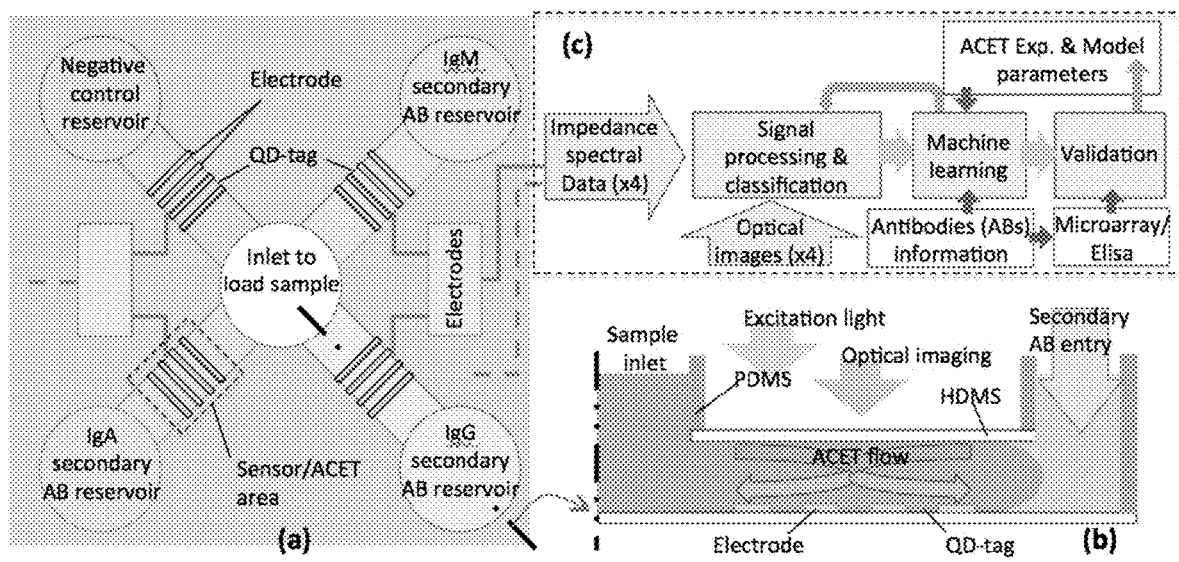
FIGS. 19A-19C show.

To overcome the aforementioned shortcomings in the existing methods, the inventors developed a multiplexed assay that integrates optical and electrical detection methods in one single microfluidic platform to take advantages from both. The platform produces multimodal signals that require machine learning mechanisms for analysis. The multiplexed assay can be used for virus antibody detection and bacteria/parasite antibody detection with specific functionalization on the electrodes. To demonstrate its capability, the inventors were able to address the most recent pandemic crisis: a Multiplexed Assay for the Immune Response to COVID-19 (MAIRC). The MAIRC schematic diagram of the various components of the present invention are shown in FIGS. 19A-19C.

The device enables the detection and quantification of COVID-19 based human IgG. IgM, IgA antibodies, which require using specific secondary antibodies to determine the type of captured immunoglobulins on each channel [31]-[33]. In this example, each chip has 4 radially extended microchannels (although more and less are possible, such as 2, 3, 4, 5, 6, 7, 8, 9, 10, 11, 12, 13, 14, 15 and more), which allows detection of 3 different antibodies in parallel, while still providing a control. Each channel includes functionalized electrodes for electrical impedance responses and functionalized florescent dots for optical detection through the transparent channel walls. The electrical and optical detections, owing to their large difference in frequencies, do not interfere with each other and can therefore be conducted in situ simultaneously with the one plasma sample.

There is a need to sense multiple biomarkers simultaneously in blood or other bodily fluids for disease diagnosis. Particularly, these biomarkers' profiles at different time points may indicate the status of the disease. In this patent disclosure, the inventors target multiple antibodies, IgG. IgM, and IgA, for infectious disease such as COVID-19 virus infection, which they can do using multiple modalities, using the same device, simultaneously.

In the microfluidic channel, two and more detection modalities can co-exist in the same locations. The modalities can include electrical (impedance, capacitance, resistance) at different operating frequencies; optical fluorescence (amplitude) at different wavelengths; optical resonance (amplitude, phase) at different wavelengths; magnetic detection (magnitude and induced impedance); and/or sur-face acoustic waves (impedance, magnitude, phase) at different operating frequencies. Two or more modalities can be detected simultaneously without interferences if their electromagnetic frequencies/wavelengths are far apart in the spectrum. In this example, the optical spectrum (hundreds of terahertz, THz) for the optical detection/imaging is far from the electrical impedance-sensing spectrum (Megahertz, MHz). Thus, the signals can be simultaneously detected. When the receptors attach the antibodies, the optical frequency (or wavelength) changes. As such, the colors change and can be detected by an imaging camera or photodetector. At the same time, the electrode impedance varies due to the antibodies attachment on the receptors coated on the surface of the electrode. Both signal transductions can co-exist in the same microfluidic device and in the close proximity of areas.

Further, In the same device, spatially configured microfluidic channels can in-parallel detect different antibodies in respective channels. The respective antibody or antigen receptors to bind with antibodies or pathogens are coated in the sensing areas. The "star" spatial arrangement allows the blood sample to flow into different channels thus there is no need to prepare multiple samples for different tests. Similar to the features disclosed in the previous patent application, the ACET alternative-current electrothermal flow control can direct the biomolecules onto the receptor-binding area, in addition to the nanorods increasing active sensing surface and the selective hydrophilic activation on the sensing area increasing reception binding efficiency. Therefore, as soon as the blood sample enters the inlet in the center the fluids with targeted molecules get drawn to the sensing areas in the microchannels.

Several major advantages are featured by the design. The channel configuration enables multiplexed sensing toward individual immunoglobulins antibodies. Each antibody is detected by both electrical and optical sensing for better accuracy. The micro-fluidic design requires a small amount of plasma sample, in which the blood can be extracted by finger prick and filtered by passive plasma filtration [34], and reagent. The antigen/antibody can be readily deposited with commercially available microarray inkjet printers [35]-[38] which can be configured for mass production [39]. These features make the device more cost-effective, easier-to-handle, relevant to larger-population point-of-care applications.

Specifically, for antibody detection, multiplexed capability provides a complete picture of immune responses in the body. There are five classes of immunoglobulin IgA, IgD, IgE, IgG, and IgM antibodies. IgG, IgA and IgM play critical roles in immune responses when viruses infect the body. Primary antibody responses occur with IgM, found mainly in blood and lymph fluid, appears first, followed by IgA mostly on mucosal surfaces and IgG in the serum. The IgG is the major antibody for the response against viral and bacterial infections, and remains stable for a half-life of 7 to 23 days. When the same or similar virus enters the body, a rapid secondary antibody response occurs. The relative distributions among the immunoglobulins for specific diseases and their temporal changes provide more information about how the immune system fights against the viruses [40]. A preliminary result obtained by ELISA of COVID-19 patients' plasma highlights the IgM/IgA/IgM distributions from day 0 to 21 [41]. For patients infected, IgM, IgA and IgG profiles show distinct chronological shapes and provide better accuracy for positive cases, even compared to the PCR tests alone. The profiles also help diagnosis for people in close contact with each other. The authors concluded a tool that can provide the multiplexed ability to detect immunoglobulins is much needed to stop the spread and ensure safety in the public [41]. [42]. It should be noted that these researchers used conventional ELISA tools to assay the blood plasma so the data are discrete with intervals of 4+ days [41]. Some sampling times are random due to test equipment constraints. Thus the three different immunoglobulin antibodies are not measured continuously for individual patients. The results emphasize the statistical meaning for the roles of immunoglobulins but cannot tell caregivers how to model the profiles in order to judge and predict the patient's recovery. Gaining the insight to individual's antibody profiles is direly important to prevent deaths because often they are caused by cytokine storm syndrome [43]. Multiplexed detection can also include sensing electrodes for pro- and anti-inflammatory cytokines such as interleukin (such as IL-Ira), monocyte chemotactic proteins (such as MCP-3) and interferon gamma induced protein (IP-10) that are shown elevated with COVID-19 disease severity [42]. Furthermore, an in-situ multiplexed assay will allow researchers to model and predict human immune responses with more accuracy.

The present invention meets all the identified needs for a quantifiable, accurate, fast, and potentially inexpensive diagnostic method based on detection of human IgG, IgM, and IgA antibodies simultaneously, which does not currently exist.

Multiplexed dual-modal sensing in microfluidic assay; Microfluidic assays and fluorescent-tag based sensing.

Microfluidic and lab-on-a-chip devices provide great advantages of versatility and flexibility for various bio- and chemical molecules, small sample and reagent consumption, shorter response time, and reduce overall costs [44], [45]. Sensing mechanisms have involved optical, magnetic, and electrical effects from micro and nano-scale interactions with the target molecules. Some principles have been commercialized as laboratory equipment and point-of-care devices such as bioanalzyer instruments, pregnancy test strips and urine analyzers. Almost all of them are based on a single modality of sensing. For large-population screening, lateral flow assays provide advantages of convenience, affordable costs and quick responses, compared to conventional ELISA (enzyme-linked immunosorbent assay) techniques [46]. Particularly, fluorescent signal based immunochromatographic sensing is often used for its simplicity, rapidness and portability [47]. However, the lateral flow cannot enhance responses, limited sensitivity due to restriction on the total sample volume, inaccuracy due to sample volume imprecision, viscosity dependency, and low tolerance to antibody quality [48]. Some of the issues can be resolved by using microfluidic techniques with active and precise flow control and sample processing. However, integrated or external micropumps with mechanical or non-mechanical mechanisms are often needed [49]-[52]. Furthermore, in addressing the sensitivity challenges while trying to keep the sample volume small and the binding efficacy high within the microfluidic devices, sample flows in the microchannels require sophisticated hydrodynamic controls, which are inherently more difficult to use and, thus, more costly.

Advantages of ACET (alternative current electrothermal) flows. An effective method for simultaneously increasing sensitivity and decreasing response time is to generate directional microflows that transport the target molecules toward functionalized sites. Among various transport mechanisms AC electroosmosis (ACEO) and AC electrothermal (ACET) [54]-[56] flows can be used to induce directional biomolecular movement. The ACEO phenomenon typically occurs at low ionic strength fluids such as DI water, and at higher conductivities ACEO flow velocity decreases significantly due to the reduced electrical double layer thickness and it eventually becomes negligible at above 0.1 S/m, making it unsuitable for most bioassays [57], [58]. As shown above, the inventors show that for a biologically relevant high-conductivity media such as phosphate buffer saline (PBS, $\sigma \sim 1.4$ S/m), ACET flow becomes the dominant phenomenon inducing directional and long-range convective vortices that can potentially drag the molecules to the middle of the electrodes' gap, conveying them tangentially to the electrode surface of the interdigitated electrode pattern [59], [60].

Impedance based sensing. Conventional ELISA immunoassays are limited by portability and high-cost operation. The background optical noises and bleaches inherently limit the limit of detection. With narrow bandwidth filtering and spatial isolation to enhance the signal-to-noise ratios, the instrument becomes bulky so it is often unsuitable for portable applications. Current methods mostly use detection of optical signals from the florescent tags and require precision optics to collect the weak emission powers generated by binding affinity. Thus, the signal recognition is solely based on accumulative optical powers within each specific band of colors.

Recently, microfluidic integrated impedance spectroscopy immunosensors have become a common technique since it provides a label-free, low cost, portable, and sensitive detection for point of care applications [61]-[64]. In this technique, a small AC voltage is applied to electrodes and, corresponding current and impedance are measured in a wide range of frequencies. For immunosensor applications, receptors/target molecule binding at the electrode surface induces alterations in the impedance, providing a direct means of detection on the sensor. However, these techniques rely on receptors/target molecules reactions, which take place through diffusion-dominated transport kinetics. Unfortunately, this mechanism is quite slow, resulting in long reaction time of several hours and low sensitivity. In extreme cases these reactions may not even occur. Thus, it is essential to develop a highly sensitive detection method for rapid screening and field-use applications. In the device of the present invention, ACET flow, local hydrophilicity on binding sites, and nanorods surface functionalization are combined in the microfluidic device to address the issues with increasing sensitivity and binding affinity.

Multiplexed sensing. Current methods for multiplex sensing typically divide samples into multiple vials or microplate wells after dilution, the so-called multiplexed sensing is not conducted in situ and concurrently with the same sample. Integrated multiplexed sensing methods have been proposed including optical ones based on fluorescence and luminescence [65], [66], surface-enhanced Raman scattering with multiple functionalization patterns and bar-code concept based microarrays [68], taking advantages of broad bandwidths of optical signals for multiplexing with a variety of functionalization techniques [70]. Since similar nano-scale materials can be used for optical and electrical detections [71], some have suggested multiple functionalized electrode methods based on impedances [72], [73]. Potentials of different modalities have been discussed in [74], [75], however, multiplexing of electrical and optical sensing has not been investigated thoroughly. For immunosensors, impedance sensing principles are implemented alone [76]-[78] but not integrated with other modality. Multiplexing concepts have only been applied for microfluidic impedance cytometry [79], that is used to sort micro-scale cells; and for single micro-size cell analysis [81].

Integrating electrical and optical sensing modalities in a single microfluidic platform provides complementary information about the samples in situ with no interference on signal transduction. In the scenarios of detecting viruses such as COVID-19, the microfluidic ACET mechanism and local hydrophilicity enhances the antigen-antibody binding for both optical power and electrical impedance detections. With spectral shapes of impedance at different frequencies, electrical signals provide more spectroscopic information for sensitivity while multiple fluoresce signatures give cross validation for specificity.

Machine learning and signal processing for the multiplexed microfluidic sensors.

The multi-modality signals, owing to different signal properties, can be coordinated to express different features for the target molecules. Such sensor signals obtained from the microchannels can be separately processed because the characteristic frequencies are far different. However, as they are acquired simultaneously in the same location, such signals can be synchronized and coordinated to obtain more information about the molecules. Particularly, the lack of markers for novel viruses and bacteria, such multi-modality detection can accelerate the analysis of pathogens. Current machining learning techniques also enable the analysis of huge amounts of complex data. The signals from the microfluidic device can be cross examined by the multi-modality feature. For example, if one pathogen has been identified with an existing antibody-conjugated quantum-dot instrument under optical detection. The electrical impedance sensing signals can be checked with the optical detection by the same quantum dots in the multiplexed device, or vice versa. The detection features then can be validated. Furthermore, ACET modeling can be carried out at the same time during experiments to provide feedback information to control the electrical biasing and impedance measurements. The outcomes can also be validated by the multimodality features. Thus the platform is readily to be integrated by current and future machine learning methods, adoptable to future uses for unknown pathogens.

ACET microfluidic device. Alternative current electrodynamics has been used to manipulate analytes to the detection region. Dielectrophoresis (DEP), AC electroosmosis (ACEO) and AC electrothermal (ACET) can be used to induce directional biomolecular movement. While DEP force proportional to the size of target particles, Brownian motion effects increasingly interfere with dielectrophoretic action of nano-size particles resulting in weak forces. DEP, directly applied over particles, exists typically within a distance of tens of μm from electrodes. ACEO typically occurs at lower ionic strength and its flow velocity decreases significantly with electrical conductivity in fluid. Studies on AC electrokinetics [59], [82] conclude that for a biologically relevant high conductivity media, such as phosphate buffer saline (PBS, σ~1.4 S/m), the ACET flow becomes predominant inducing directional and longer-range convective vortices that can potentially direct the molecules to the middle of the electrodes' gap, then conveys them tangentially to the electrode surface of the interdigitated electrode pattern or the target surface with the fluorescent tags.

Figure 20:
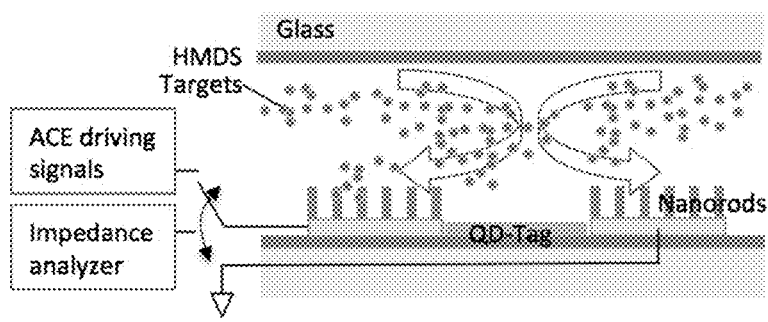
FIG. 20 shows an alternative current electrothermal flow operation and the dual modality sensing.

FIG. 20 schematically shows the ACET operation mechanism in the sensor. An AC voltage at 5-MHz frequency is applied to the side electrodes using a function generator. ACET flow carries the target molecules to the immobilized receptors region and the impedance increases due to the chemical binding. ACET flow is obtained by applying 4Vpp at 5 MHz, while impedance measurements are performed at 0.02 Vpp at 5 MHz. The impedance measurement frequencies can be varied to obtain spectral responses. Impedance of the electrodes and fluorescent optical power spontaneously increase until all target molecules are bond on the functionalized electrodes and tags. In cases where it is difficult to visualize the flow, the results are validated with the impedance measurements and modeling.

ACET mechanism by definition inherently increases the local temperatures in the fluid owing to Joule heating. The design of the present invention avoids large temperature increases that may denature the ligands on the sensor surfaces. Therefore, operation conditions are selected coordinately. The specific binding reactions were conducted using Bovine IgG whole molecules by applying a 5 MHz AC voltage at 4Vpp for ACET flow, which increases the local temperature by 2° C. on the electrode surface [60]. FIG. 21 summarizes the investigation on average temperature rise on the side and middle electrodes as a function of applied voltage at 5 MHz. The experimental data are obtained by using a thermoreflectance method with the standard deviations obtained from 50 different measurements for any applied voltage. The numerical model (solid lines) and experimental results are in good match because the operating frequency is relatively low to ignore parasitic capacitances so the majority of the applied electrical fields contribute to Joule heating. It should be noted that the temperature increases are larger compared to theory in the low voltages while they match closely at higher voltages. This is due to the measurement limitation since it is more difficult to detect small changes of temperature in liquid.

Impedance sensing. The impedance detection mechanism detects impedance changes at the interface between the interdigitated electrode and the sample solution due to binding reactions. The ACET flow carries the target molecules to the immobilized receptors region and the impedance increases due to the chemical binding. Impedance measurements are driven by a function generator at 0.02 Vpp @ 5 MHz and measured by an impedance analyzer. An electrical switch is implemented to multiplex the sensors and flow control. Binding of target molecules to the receptors are obtained by calculating the normalized impedance change using the formula:

$$\frac{\Delta Z}{Z_{ref}} = \frac{Z_{after\ binding} - Z_{before\ binding}}{Z_{before\ binding}}$$

which is used as an indication for target molecules binding to the antibody.

As mentioned above, specific binding reactions are conducted using Bovine IgG on the test device shown in FIG. 13. The normalized impedance changes are plotted as a function of time in FIGS. 22A and 22B for (FIG. 22A) planar and (FIG. 22B) nanorods-structured electrodes using three different concentrations of solution (1:10:100 dilutions). The nanorods deposited on the electrode increase reaction surface areas without increasing electrode footprint. The impedance change without ACET flow remains constant around zero, while it increases monotonically with time under ACET flow due to the directed binding reactions. For the 100 ng/ml target solution, the impedance change reached ~15% and 25% within a minute by the planar and nanorods-structured electrodes, respectively, while the impedance changes of 8% and 20% were recorded at 1:100 dilution. These results show that ACET leads to enhance detection sensitivity.

FIG. 23A shows an SEM of the gold nanorod functionalized surfaces [60]. The patterning of the nanostructures is carried out using the template-assisted electro-deposition method based on nanoporous anodic aluminum oxide (AAO) layer [83]. The templates are used for electrodeposition to grow nanorods of nickel/gold (300 nm long) or IrOx (1 μm long) shown in FIG. 23B shows the results show clear increase of sensitivity for IgG detection by the impedance sensor in FIG. 22B and for electrochemical biomarkers[84], [85].

Figure 24:
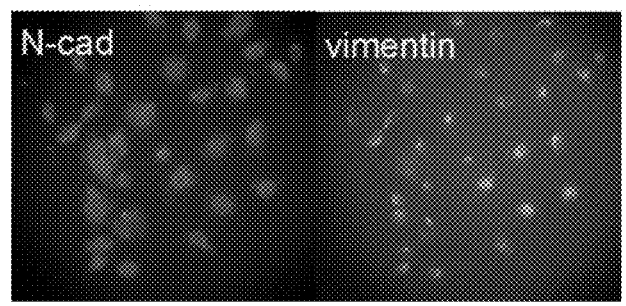
FIG. 24 shows fluorescent images for two biomarkers in a microfluidic channel.

Fluorescent tags for biomarker sensing. Fluorescent biosensing based on quantum dots [87]-[91], fluorescent dyes [92], and fluorescent protein [94]-[97] have been well developed for many different types of pathogens, proteins, cells, biomarkers and viruses. With a variety of different approach to conjugate antigens or receptors, commercial fluorescent readers are available to deliver high accuracy and sensitivity results through narrowband optical filters, high dynamic range detectors and multi-well plates. Both quantum-dot based and fluorescent tagged protein methods in examining prostate cancer cells for metastasis under chemo-attractant factors and mechano-stimuli within microfluidic devices have been conducted by the present inventors. One example for the examination of biomarkers can be explained with the fluorescent images captured on metastatic cells after treatment with antibodies [101]. It was seen in FIG. 24 that vimentin, considered as a marker for Mesenchymal cells [102], and N-cadherin, a hallmark of epithelial-to-mesenchymal transition [103], are expressed by the cells that migrate across microchannels in response to chemoattractant 2 ng/ml TGF-β. The identification of such biomolecules can be imaged through a fluorescent microscope since both HMDS and glass substrate are optically transparent, and the images can be analyzed automatically by signal processing, image recognition via machine learning mechanisms. For the final goal for a portable device, the optical power of fluorescent wavelengths can be simply measured by collecting the light with a lens attached on the glass substrate, a dielectric filter and a high dynamic range photodetector.

Develop the multiplexed microfluidic impedance spectrometry assays utilizing alternative current electrothermal (ACET) flow.

Using the present invention, it is possible to demonstrate electrical impedance variations on a multiplexed device to sense the specific binding events enhanced by convective mixing and pumping with the ACET flow. Furthermore, hydrophobic channel surfaces to increase detection sensitivity by reducing nonspecific binding on the channel surfaces, while hydrophilic sensor surfaces employ nanostructures to increase the binding surface area.

Optimize chip geometry and fabricate chips. As shown above, ACET flow pumping and impedance measurements use 0.1 ml reagent volume in a single channel for demonstration. For example, 1 ml of blood plasma divided equally into 4 channels. Channel shape optimization can be conducted using COMSOL Multi Physics to simulate the 3-D ACET flow and antibody-antigen binding reactions on the electrodes and computationally optimize the electrode and micro-channel dimensions. The device operation parameters such as ACET pumping and impedance spectroscopy frequencies can now be determined.

Increase local hydrophilicity. For the construction of microfluidic systems to meet mass production requirements, a hybrid approach was selected that uses a glass substrate where electrodes can be deposited with semiconductor processes and a polymer superstrate made by micro-molding.

Hydrophilicity of the sensor surface is a prerequisite to create a high affinity receptor binding. Typically, the surface on a hydrophilic substrate, where the sensors are located, is conjugated with receptors. This results in low binding cites on the sensor region because the receptors assay spreads out the surface due to the adhesive forces. Localization of the receptors on an electrode surface can improve binding to reach a high performance immunosensor by defining hybrid surfaces on which the electrode surface presents hydrophilic characteristics while the rest of the substrates remains hydrophobic. Low surface energy activation on microfluidic materials such as hexamethyldisilazane (HMDS) can be used to modify a hydrophilic surface. For a simple, inexpensive, and disposable device, the inventors chose HMDS for both the optical transparency and hydrophobic nature on surface. The inventors used plasma-activated HMDS on SiO2 glass where the electrodes are fabricated to form a self-assembled monolayer and transform the hydrophilic surface to hydrophobic. HMDS is proven to be biocompatible which makes it a good candidate for such biosensor applications.

Figures 25A, 25B:
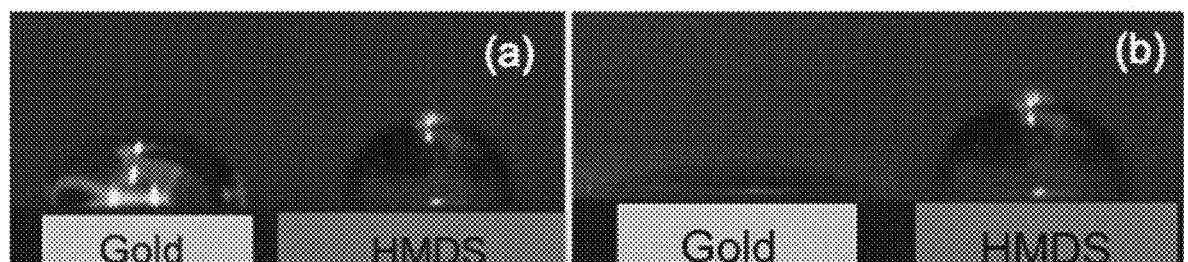
FIGS. 25A and 25B shows the wettability of a nanorod electrode on HMDS coated glass substrate (FIG. 25A) before and (FIG. 25B) after UV treatment on the electrode.

Ultraviolet (UV) treatment is a good method for increasing the surface hydrophilicity without influencing the electrode microstructure characteristics. Wetting characteristics of the electrodes were investigated utilizing contact angle measurements. Static contact angles at various locations were measured. The baseline glass is hydrophilic (19°±2.3°). After being treated for 24 h in HMDS solution, the surface became hydrophobic (99°±1.7). Then gold electrodes were fabricated (photolithography [60]), the contact angle on the electrode was 77.87°±1.54° (FIG. 25A). After exposing with UV light selectively using a photomask, FIG. 25B shows the water droplet completely infiltrated into the electrode surface, indicating a transition from hydrophilic to super hydrophilic with a contact angle less than 10°. Owing to the photomask, the contact angle for the HDMS was preserved.

Some advantages of using nanorod patterned electrode surfaces include reduced electrode polarization effects [82], which are dominant in high conductivity buffers like blood plasma; and increased sensing surface area leading to increased sensitivity as shown in FIGS. 22A and 22B. 85-nm diameter nanorods can be made with nickel/gold, expecting an aspect ratio (height/diameter) of 4.1 and 6 times surface area increase (but can also be 2, 3, 4, 5, 6, 7, 8, 9 or 10 times surface area increase). For example, 1-μm long IrOx nanorods are used, as they are more stiff to stand vertically, which increases the surface area up to about 10, 15, 20 or 25 times. The UV light treatment to create super hydrophilic surfaces and optimization of nanorod size and seeding can be investigated for the goal of reaching the highest device sensitivity. Furthermore, the nanorod modification on surface should be suitable for efficient functionalization for the receptors and allow effective convective diffusive transport of the primary and secondary antibodies.

Determine device sensitivity. The device of the present invention provides great sensitivity for different antibody concentrations in the reagent. Detection can be recorded beyond 20 minutes to determine the optimum time scales and device sensitivity at various concentrations and ACET parameters. Responses as a function of the concentration of the target immunoglobulins can be used to determine the detection limits and at the same time allow the generation of calibration curves. Data can then be fed into the machine learning algorithms, which determine the immunoglobulins' levels for patients in future clinical applications. Determination of device sensitivity can be conducted using IgG, IgM and IgA antibodies separately.

Determine device specificity. Nonspecific binding on the receptor surfaces can lead to false results. For reliable measurements, all functionalized channels (FIG. 18) should exhibit similar impedance responses due to the capture of all three types of COVID-19 human antibodies in the blood plasma during the nonspecific antibody capture stage, while the impedance of the 4th (unfunctionalized) channel should not vary. The specific secondary antibodies can be introduced and impedance variations can be recorded to identify the specific immunoglobulin. For example, plasma containing a known concentration of COVID-19 IgG antibodies can be introduced to the system and detection of IgG can be performed using secondary IgG, IgM and IgA antibodies in 3 functionalized channels. Impedance in the channels containing secondary IgM and IgA as well as that in the unfunctionalized 4th channel should remain constant, as to avoid false positive results. On the other hand, little or no impedance variations after releasing the secondary IgG antibodies is an indicator for false negative results. Device specificity can be tested and determined using control antibodies. Impedance changes in all channels as a function of the immunoglobin levels and time scales can be analyzed in the machine learning methods to ensure consistency and reliability.

Integration of fluorescent-based sensing in the multiplexed ACET microfluidic assays.

Design, fabricate and test a microfluidic platform with multiplexed channel configurations for deposition of quantum dot (QD) conjugated antibodies. QD conjugates are commercially available that can be excited at 540 ad 630-nm wavelength ranges. With narrow emission bandwidths, four optical filters can be used with a video microscope to image the device in a single shot. QDs offer rapid responses with significantly less photo-bleaching allow high resolution images and wide dynamic ranges. For feasibility demonstration, mouse anti-MAPs primary monoclonal antibody and rabbit anti-GFAP primary antiserum can be used with QD #1 anti-rabbit secondary antibody and goat Fab2 anti-rabbit IgG conjugate and QD #2 anti-mouse secondary antibody and goat Fab2 anti-mouse IgG conjugate. Immobilization can be implemented with UV-light cross-linked poly(ethylene glycol) (PEG) hydrogel after deposition with a high-precision syringe on the substrate. The mixture viscosity can be tested in order to achieve a well-confined binding area so the optical performance can be compared fairly. Two different antibodies can be detected using the two QD-conjugated secondary antibodies in bovine serum. The experiments can be conducted with the antibodies separated and mixed together in the microchannels. Different concentrations of antibodies in reagent buffers can be investigated for sensitivities and specificity, as well as optical bleaching and signal-to-noise ratios. The results from the integrated microfluidic device are compared to results in well plates by a fluorescent reader.

Develop the optical sensor with inkjet-printed fluorescent spots in the ACET microfluidic channels.

Integrating the optical sensors into the ACET requires precise deposition of the florescent-tag spots between the electrodes, while the antigens can be deposited on the electrodes, as the ACET flows direct the fluid toward the sensing areas. Non-contact Inkjet printing of fluorescently labeled antibody/antigen from buffer and an excipient such as Polyethylene Glycol (PEG) has been utilized to pattern immune-assay in the array form of multiple spots on paper or glass substrates [38], [113]. Commercial piezoelectric inkjet printers are available to deposit an antibody spot with a 100-300 pL volume with a 150-µm diameter. First, the targeted QD-conjugated antibodies can be tested for patterning with viscosity, concentrations, deposition speeds, drying times and uniformity. Once the spot size is determined, fluorescent images can be taken with different concentration of targeted antibodies diluted in buffer to examine the sensitivities and dynamic ranges to establish the limit of detection. Interference antibodies can be added with various concentrations to test the specificity and signal-to-noise ratios. The total and average optical powers can be calculated from the images for the specifications of optical designs in the future integrated system.

HDMS channel mold can be attached on the glass substrate and ACET flows can be applied in the micro-channels with control through electrodes. First, a voltage of 0-6Vpp at 5 MHz can be applied, as demonstrated before, and six different concentrations of antibodies in bovine serum and buffer can be tested to record the optical images as a function of time to determine the binding efficiency increases owing to the ACET feature. The results can be compared to the electrical impedance measurements. Then different interference antibodies can be added with various concentrations to determine specificity and signal-to-noise ratios. Since the microchannels and HMDS layers can behave as optical waveguides, particular attention is paid on the saturation and bleaching of optical signals. The studies can be repeated for several different inkjet-printed spot sizes. Accumulative digital optical images can be analyzed for optical characteristics such as bandwidths, powers, and spot sizes to compare with the results from well plates.

Design the integrated optical system for the fluorescent detection.

Time-lapse fluorescent images are taken with a microscope video camera to investigate optical performance. In the ultimate design of a complete portable system, the inventors can integrate the optical components with the microfluidic device. Excitation LED can be attached on the HMDS mold while an integrated photodetector centered at 540 or 630 nm wavelength can be mounted under the glass substrate. Both through-hole and surface mount devices can be tested to determine their optical conversion efficiency, compared to the results of calculated power powers from the recorded images. Integrated devices, for both ACET flow control and optical detection, can be developed to determine the overall performance of sensitivity, saturation, noises, and the detection limit with various concentrations of antibodies. Hardware and Software Integration The electrical and optical sensing mechanisms can be integrated in the same 4-channel microfluidic devices. Electrodes, nanorods and HDMS can be deposited and local hydrophilicity can be achieved by UV activation before the quantum-dot hydrogel spots are deposited. Then the devices can be tested after encapsulation by PDMS with fluidic leak, electrode conductivity, temperature changes and optical power detection. Measurements can be repeated except now both electrical and optical data can be collected from the single device in situ and concurrently. The combined multimodal and multi-task neural architecture search methods can be implemented for signal processing and data analysis. Results can be compared with their respective outcomes and the flow control parameters can be adjusted with feedback from the concluded data by machine learning.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

As used herein, the term "binding molecule" refers to a molecule that has a specific molecular interaction and binding to a "target molecule". The binding molecules for use with the present invention are often selected to specifically bind one or more specific target molecules. A common example of a binding molecule is an antibody, which is a polypeptide that include at lease one antigen binding region or domain. Other examples of binding molecules can include receptors, that have a cognate ligand. Many other interactions are possible, such as Protein A binding to antibodies, lipopolysaccharide binding proteins that bind lipopolysaccharides, receptor-ligand interactions such as epidermal growth factor and epidermal growth factor receptor, small molecule hormones (e.g., steroids) and their receptors, nucleic acid binding proteins and their cognate nucleic acid target and/or nucleic acid sequence, antibodies and Fc receptors, enzymes and substrates, or interactions that lead to a molecule change to the molecular structure of a target molecule, such as, phosphorylation, dephosphorylation, lipidation, glycosylation, etc.

As used herein, the term "target molecule" refers to a molecule that is to be detected, e.g., in a liquid sample that is suspected of having the target molecule. Target molecules can be as small as individual atoms, but more often includes small molecules, peptides, proteins, protein complexes, nucleic acids (RNA, DNA, etc.), carbohydrates, lipids, combinations of peptides and other macromolecules (e.g., glycoproteins, glycolipids, etc.). A target molecule, when bound by an antibody is referred to as an antigen.

As used herein, the term "antigen" refers to a molecule that is bound by an antibody or that is presented on Major Histocompatibility Complex molecules. Antigens include any type of biologic molecule, including, for example, simple intermediary metabolites, sugars, lipids and hormones as well as macromolecules such as complex carbohydrates, phospholipids, nucleic acids and proteins, and combinations thereof such as glycoproteins, glycolipids, histone-DNA molecules, etc. Common categories of antigens include, but are not limited to, viral antigens, bacterial antigens, fungal antigens, protozoan and other parasitic antigens, tumor antigens, antigens involved in autoimmune disease, allergy and graft rejection, and other miscellaneous antigens.

Target molecules can include a peptide or protein antigen that includes a primary, secondary or tertiary structure similar to an epitope located within any of a number of pathogen polypeptides encoded by the pathogen DNA or RNA. The level of similarity will generally be to such a degree that monoclonal or polyclonal antibodies directed against such polypeptides will also bind to, react with, or otherwise recognize, the peptide or protein antigen. Various immunoassay methods may be employed in conjunction with such antibodies, such as, for example, Western blotting, ELISA, RIA, and the like, all of which are known to those of skill in the art. The identification of pathogen epitopes, and/or their functional equivalents, suitable for use in vaccines is part of the present invention. Once isolated and identified, one may readily obtain functional equivalents. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Target molecules can include peptides from, e.g., pancreas, L-asparaginase, hyaluronidase, chymotrypsin, trypsin, tPA, streptokinase, urokinase, pancreatin, collagenase, trypsinogen, chymotrypsinogen, plasminogen, streptokinase, adenyl cyclase, superoxide dismutase (SOD), and the like.

Examples of target molecules can include cytokines or their receptors, including, without limitation, interleukins, transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Cytokines may be B/T-cell differentiation factors, B/T-cell growth factors, mitogenic cytokines, chemotactic cytokines, colony stimulating factors, angiogenesis factors, IFN-alpha, IFN-beta, IFN-gamma, IL1, IL2, IL3, IL4, IL5, IL6, IL7, IL8, IL9, IL10, IL11, IL12, IL13, IL14, IL15, IL16, IL17, IL18, etc., leptin, myostatin, macrophage stimulating protein, platelet-derived growth factor, TNF-alpha, TNF-beta, NGF, CD40L. CD137L/4-1BBL, human lymphotoxin-.beta., G-CSF, M-CSF, GM-CSF, PDGF, IL-1a, IL1-b, IP-10, PF4, GRO, 9E3, erythropoietin, endostatin, angiostatin, VEGF or any fragments or combinations thereof. Other cytokines include members of the transforming growth factor (TGF) supergene family include the beta transforming growth factors (for example TGF-B1, TGF-B2, TGFB3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); Inhibins (for example, Inhibin A, Inhibin B); growth differentiating factors (for example, GDF-1); and Activins (for example, Activin A, Activin B, Activin AB).

Other examples of target molecules can include viral particles, portions or components; bacteria, bacterial portions or components; fungi, fungal portions or components; or parasites, parasitic portions or components, or their binding targets on cells.

Examples of target molecules, such as viral antigens including, but are not limited to, e.g., retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; *Abies* viral antigens such as *Abies* glycoprotein. *Abies* nucleoprotein and other *Abies* viral antigen components. See Fundamental Virology, Second Edition, eds. Fields, B. N. and Knipe, D. M. (Raven Press, New York, 1991) for additional examples of viral antigens.

Viruses include picornavirus, coronavirus, togavirus, flavirvirus, rhabdovirus, paramyxovirus, orthomyxovirus, bunyavirus, arenavirus, reovirus, retrovirus, papilomavirus, parvovirus, herpesvirus, poxvirus, hepadnavirus, and spongiform virus. Other viral targets include influenza, herpes simplex virus 1 and 2, measles, dengue, smallpox, polio or HIV. Pathogens include trypanosomes, tapeworms, roundworms, helminthes, malaria. Tumor markers, such as fetal antigen or prostate specific antigen, may be targeted in this manner. Other examples include, HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. In some cases, vaccination of an individual may only be required infrequently, such as yearly or biennially, and provide long term immunologic protection against the infectious agent. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Examples of target molecules, such as bacterial antigens include bacterial antigens such as pertussis toxin, filamentous hemagglutinin, pertactin, FIM2, FIM3, adenylate cyclase and other pertussis bacterial antigen components; diptheria bacterial antigens such as diptheria toxin or toxoid and other diptheria bacterial antigen components; tetanus bacterial antigens such as tetanus toxin or toxoid and other tetanus bacterial antigen components; streptococcal bacterial antigens such as M proteins and other streptococcal bacterial antigen components; gram-negative bacilli bacterial antigens such as lipopolysaccharides and other gram-negative bacterial antigen components. *Mycobacterium tuberculosis* bacterial antigens such as mycolic acid, heat shock protein 65 (HSP65), the 30 kDa major secreted protein, antigen 85A and other mycobacterial antigen components; *Helicobacter pylori* bacterial antigen components; pneumococcal bacterial antigens such as pneumolysin, pneumococcal capsular polysaccharides and other pneumococcal bacterial antigen components; *haemophilus* influenza bacterial antigens such as capsular polysaccharides and other *haemophilus* influenza bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens. Partial or whole pathogens may also be: *haemophilus* influenza; *Plasmodium falciparum; Neisseria meningitidis; Streptococcus pneumoniae: Neisseria gonorrhoeae; salmonella* serotype *typhi; shigella; Vibrio cholerae*; Dengue Fever; Encephalitides: Japanese Encephalitis; lyme disease; *Yersinia pestis*; west nile virus; yellow fever; tularemia; hepatitis (viral; bacterial); RSV (respiratory syncytial virus); HPIV 1 and HPIV 3; adenovirus; and small pox.

Examples of target molecules, such as fungi, include *candida* fungal antigen components; *histoplasma* fungal antigens such as heat shock protein 60 (HSP60) and other *histoplasma* fungal antigen components: cryptococcal fungal antigens such as capsular polysaccharides and other cryptococcal fungal antigen components; coccidiodes fungal antigens such as spherule antigens and other coccidiodes fungal antigen components; and tinea fungal antigens such as trichophytin and other coccidiodes fungal antigen components.

Examples of target molecules, such as protozoans, include protozoal and other parasitic antigens include, but are not limited to, e.g., *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components.

Examples of target molecules, such as cell surface markers can include MHC class I, MHC Class II, B7-2, CD18, CD29, CD31, CD43, CD44, CD45, CD54, CD58, CD83, CD86, CMRF-44, CMRF-56, DCIR and/or ASPGR and the like; while in some cases also having the absence of CD2, CD3, CD4, CD8, CD14, CD15, CD16, CD 19. CD20, CD56, and/or CD57. Examples of cell surface markers for antigen presenting cells include, but are not limited to, MHC class I, MHC Class II, CD40, CD45, B7-1, B7-2, IFN-gamma receptor and IL-2 receptor, ICAM-1 and/or Fc-gamma receptor. Examples of cell surface markers for T cells include, but are not limited to, CD3, CD4, CD8, CD 14, CD20, CD11b, CD16, CD45 and HLA-DR, and any cluster of differentiation (CD #) antigens, such as any one of CD1 to CD371, as determined by the Human Leukocyte Differentiation Antigen Workshops.

Examples of target molecules, such as tumor antigens typically will be derived from the cell surface, cytoplasm, nucleus, organelles and the like of cells of tumor tissue. Examples of tumor targets for the antibody portion of the present invention include, without limitation, hematological cancers such as leukemias and lymphomas, neurological tumors such as astrocytomas or glioblastomas, melanoma, breast cancer, lung cancer, head and neck cancer, gastrointestinal tumors such as gastric or colon cancer, liver cancer, pancreatic cancer, genitourinary tumors such cervix, uterus, ovarian cancer, vaginal cancer, testicular cancer, prostate cancer or penile cancer, bone tumors, vascular tumors, or cancers of the lip, nasopharynx, pharynx and oral cavity, esophagus, rectum, gall bladder, biliary tree, larynx, lung and bronchus, bladder, kidney, brain and other parts of the nervous system, thyroid, Hodgkin's disease, non-Hodgkin's lymphoma, multiple myeloma and leukemia. Specific non-limiting examples of tumor antigens include: CEA, prostate specific antigen (PSA), HER-2/neu, BAGE, GAGE, MAGE 1-4, 6 and 12, MUC (Mucin) (e.g., MUC-1, MUC-2, etc.), GM2 and GD2 gangliosides, ras, myc, tyrosinase, MART (melanoma antigen), Pmel 17(gp100), GnT-V intron V sequence (N-acetylglucoaminyltransferase V intron V sequence), Prostate Ca psm, PRAME (melanoma antigen), .beta.-catenin, MUM-1-B (melanoma ubiquitous mutated gene product), GAGE (melanoma antigen) 1, BAGE (melanoma antigen) 2-10, c-ERB2 (Her2/neu), EBNA (Epstein-Barr Virus nuclear antigen) 1-6, gp75, human papilloma virus (HPV) E6 and E7, p53, lung resistance protein (LRP), Bcl-2, and Ki-67. In addition, the immunogenic molecule can be an autoantigen involved in the initiation and/or propagation of an autoimmune disease, the pathology of which is largely due to the activity of antibodies specific for a molecule expressed by the relevant target organ, tissue, or cells, e.g., SLE or MG.

Examples of target molecules, such as antigens involved in autoimmune diseases, allergy, and graft rejection can be used in the compositions and methods of the invention. For example, an antigen involved in any one or more of the following autoimmune diseases or disorders can be used in the present invention: diabetes, diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis. Examples of antigens involved in autoimmune disease include glutamic acid decarboxylase 65 (GAD 65), native DNA, myelin basic protein, myelin proteolipid protein, acetylcholine receptor components, thyroglobulin, and the thyroid stimulating hormone (TSH) receptor. Examples of antigens involved in allergy include pollen antigens such as Japanese cedar pollen antigens, ragweed pollen antigens, rye grass pollen antigens, animal derived antigens such as dust mite antigens and feline antigens, histocompatibility antigens, and penicillin and other therapeutic drugs. Examples of antigens involved in graft rejection include antigenic components of the graft to be transplanted into the graft recipient such as heart, lung, liver, pancreas, kidney, and neural graft components. The antigen may be an altered peptide ligand useful in treating an autoimmune disease.

As used herein, the term "signal" refers to a nucleic acid segment to which a detectable agent (e.g., a fluorophore, metal, magnet, bar code) or an activity (e.g., enzymatic, chemiluminescent, resonance transfer, radiation). There are many types of detectable labels, including fluorescent labels, which are easily handled, inexpensive and nontoxic. Often, the signal will be amplified, as is common with enzymatic and chemiluminescent enzymes.

As used herein, the terms "markers," "detectable markers" and "detectable labels" are used interchangeably to refer to compounds and/or elements that can be detected due to their specific functional properties and/or chemical characteristics, the use of which allows the agent to which they are attached to be detected, and/or further quantified if desired, such as, e.g., an enzyme, radioisotope, electron dense particles, magnetic particles or chromophore. There are many types of detectable labels, including redox and fluorescent labels, which are easily handled, inexpensive and nontoxic.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"). "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112. U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

[1] S. M. Chamow and A. Ashkenazi, "Immunoadhesins: principles and applications. Trends in biotechnology," vol. 14, no. 2, pp. 52-60, 1996.

[2] Z. Z. Rashid, S. N. Othman, M. N. A. Samat, U. K. Ali, and K. K. Wong, "Diagnostic performance of COVID-19 serology assays.," Malays. J. Pathol., vol. 42, no. 1, pp. 13-21, 2020.

[3] W. N. Liang and others, "Severe acute respiratory syndrome-retrospect and lessons of 2004 outbreak in China," Biomed Env. Sci., vol. 19, no. 6, pp. 445-451, 2006.

[4] T. Abraham, "The Story of SARS Twenty-first Century Plague. Retrieved 22 Jan. 2020.," archive.org, 2004.

[5] A. Assiri et al., "Epidemiological, demographic, and clinical characteristics of 47 cases of Middle East respiratory syndrome coronavirus disease from Saudi Arabia: a descriptive study," Lancet, vol. 13, p. 9.

[6] Y. M. Baez-Santos, S. E. St. John, and A. D. Mesecar, "The SARS-coronavirus papain-like protease: Structure, function and inhibition by designed antiviral compounds," Antiviral Res., vol. 115, pp. 21-38, 2015, doi: 10.1016/j.antiviral.2014.12.015.

[7] P. S. Zumla A Hui D S, "Middle East respiratory syndrome," Lancet., vol. 386, no. 9997, pp. 995-1007, September 2015.

[8] P. Spreeuwenberg and others, "Reassessing the Global Mortality Burden of the 1918 Influenza Pandemic," Am. J. Epidemiol., vol. 187, no. 12, pp. 2561-2567, December 2018.

[9] CIDRAP, "'Pandemic H1N1 2009 Influenza'. CIDRAP. Center for Infectious Disease Research & Policy, University of Minnesota.," 2011.

[10] CDC, "Key Facts About Influenza (Flu)," Centers for Disease Control and Prevention (CDC), 2014.

[11] G. M. Brankston G., Gitterman L., Hirji Z., Lemieux C., "Transmission of influenza A in human beings," Lancet Infect Dis, vol. 7, no. 4, pp. 257-265, April 2007.

[12] WHO, "Up to 650 000 people die of respiratory diseases linked to seasonal flu each year," World Health Organization (WHO) (Press release), Dec. 14, 2017.

[13] J. C. Schultz, A. A. Hilliard, L. T. Cooper, and C. S. Rihal, "Diagnosis and treatment of viral myocarditis," Mayo Clin. Proc., vol. 84, no. 11, pp. 1001-1009, November 2009, doi: 10.4065/84.11.1001.

[14] Merck, "Overview of Enterovirus Infections," Merck & Co, February 2018.

[15] WHO, "Key facts about Malaria," World Health Organization, Jan. 14, 2020.

[16] H. Ma and K. J. Shieh, "ELISA Technique.," Nat Sci, vol. 4, no. 2, pp. 36-37, 2006.

[17] L. Ching. S. P. Chang, and V. R. Nerurkar, "COVID-19 Special Column: Principles Behind the Technology for Detecting SARS-COV-2, the Cause of COVID-19.," Hawai'i J. Heal. Soc. Welf., vol. 79, p. 136, 2020.

[18] P. I. Kontou, G. G. Braliou, N. L. Dimou, G. Nikolopoulos, and P. G. Bagos, "Antibody tests in detecting SARS-COV-2 infection: a meta-analysis. Diagnostics," vol. 10, no. 5, p. 319, 2020.

[19] L. Zhong et al., "Detection of serum IgM and IgG for COVID-19 diagnosis.," Sci. China Life Sci., vol. 63, pp. 777-780, 2020.

[20] S. K. Vashist, "In vitro diagnostic assays for COVID-19 recent advances and emerging trends," Diagnostics, vol. 10, no. 4, p. 202, 2020.

[21] D. F. Hochstrasser, M. G. Harrington, A. C. Hochstrasser, M. J. Miller, and C. R. Merril, "Methods for increasing the resolution of two-dimensional protein electrophoresis," Anal. Biochem., vol. 173, no. 2, pp. 424-435, 1988.

[22] C. Zhang et al., "Clinical and pharmaceutical applications of affinity ligands in capillary electrophoresis: A review," J. Pharm. Biomed. Anal., vol. 177, p. p.112882, 2020.

[23] H. L. Smits et al., "Lateral-flow assay for rapid scrodiagnosis of human leptospirosis.," Clin. Diagn. Lab. Immunol., vol. 8, no. 1, pp. 166-169, 2001.

[24] M. Sajid, A. N. Kawde, and M. Daud, "Designs, formats and applications of lateral flow assay: A literature review," J. Saudi Chem. Soc., vol. 19, no. 6, pp. 689-705, 2015.

[25] E. Bendavid et al., COVID-19 Antibody Seroprevalence in Santa Clara County, California. MedRxiv, 2020.

[26] I. Cassaniti et al., "Performance of VivaDiag COVID-19 IgM/IgG Rapid Test is inadequate for diagnosis of COVID-19 in acute patients referring to emergency room department," J. Med. Virol., vol. 19, 2020.

[27] A. Tahamtan and A. Ardebili, "Real-time RT-PCR in COVID-19 detection: issues affecting the results.," Expert Rev Mol Diagn., vol. 20, no. 5, pp. 453-454, 2020.

[28] Y. W. Tang, J. E. Schmitz, D. H. Persing, and C. W. Stratton, "The laboratory diagnosis of COVID-19 infection: current issues and challenges.," J. Clin. Microbiol., 2020.

[29] J. Abbasi, "The promise and peril of antibody testing for COVID-19," JAMA, vol. 323, no. 19, pp. 1881-1883, 2020.

[30] N. M. Okba et al., "Severe Acute Respiratory Syndrome Coronavirus 2-Specific Antibody Responses in Coronavirus Disease 2019 Patients.," Emerg. Infect. Dis., vol. 26, p. 7, 2020.

[31] A. Sa-Ngasang et al., "Specific IgM and IgG responses in primary and secondary dengue virus infections determined by enzyme-linked immunosorbent assay.," Epidemiol. Infect., vol. 134, no. 4, pp. 820-825, 2006.

[32] M. E. Koivunen and R. L. Krogsrud, "Principles of immunochemical techniques used in clinical laboratories," Lab. Med., vol. 37, no. 8, pp. 490-497, 2006.

[33] A. Kabiraj, J. Gupta, T. Khaitan, and P. T. Bhattacharya, "Principle and techniques of immunohistochemistry—a review.," Int J Biol Med Res, vol. 6, no. 3, pp. 5204-5210, 2015.

[34] J. Hauser, G. Lenk, J. Hansson, O. Beck, G. Stemme, and N. Roxhed, "High-yield passive plasma filtration from human finger prick blood.," Anal. Chem., vol. 90, no. 22, pp. 13393-13399, 2018.

[35] E. A. Roth, T. Xu, M. Das, C. Gregory, J. J. Hickman, and T. Boland, "Inkjet printing for high-throughput cell patterning.," Biomaterials, vol. 25, no. 17, pp. 3707-3715, 2004.

[36] K. Abe, K. Kotera, K. Suzuki, and D. Citterio, "Inkjet-printed paper-fluidic immuno-chemical sensing device," Anal Bioanal Chem, vol. 398, no. 2, pp. 885-893, 2010.

[37] I. McWilliam, M. C. Kwan, and D. Hall, Inkjet printing for the production of protein microarrays, Protein Microarrays. Humana Press, 2011.

[38] D. Y. Joh et al., "Inkjet-printed point-of-care immunoassay on a nanoscale polymer brush enables subpicomolar detection of analytes in blood," Proc. Natl. Acad. Sci., vol. 114, no. 34, pp. 7054-E7062, 2017.

[39] B. Feyssa, C. Liedert, L. Kivimaki, L. S. Johansson, H. Jantunen, and L. Hakalahti, "Patterned immobilization of antibodies within roll-to-roll hot embossed polymeric microfluidic channels," PLOS One, vol. 8, p. 7, 2013.

[40] C. A. Janeway, P. Travers, M. Walport, and M. J. Shlomchik, The distribution and functions of immunoglobulin isotypes. In Immunobiology: The Immune System in Health and Disease. 5th edition. 2001.

[41] L. Guo et al., "Profiling carly humoral response to diagnose novel coronavirus disease (COVID-19)," Clin. Infect. Dis., vol. 2020.

[42] G. Siracusano, C. Pastori, and L. Lopalco, "Humoral immunity in COVID-19 patients: a window on the state of the art.," Front. Immunol., vol. 11, p. 1049, 2020.

[43] S. H. Nile, A. Nile, J. Qiu, L. Li, X. Jia, and G. Kai, "COVID-19: Pathogenesis, cytokine storm and therapeutic potential of interferons," Cytokine Growth Factor Rev., vol. S1359-6101, no. 20, 2020.

[44] A. M. Streets and Y. Huang, "Chip in a lab: Microfluidics for next generation life science research.," Biomicrofluidics, vol. 7, no. 1, p. p.011302, 2013.

[45] S. Halldorsson, E. Lucumi, R. Gomez-Sj"oberg, and R. M. Fleming, "Advantages and challenges of microfluidic cell culture in polydimethylsiloxane devices.," Biosens. Bioelectron., vol. 63, pp. 218-231, 2015.

[46] H.-A. Joung, Y. K. Oh, and M.-G. Kim, "An automatic enzyme immunoassay based on a chemiluminescent lateral flow immunosensor," Biosens. Bioelectron., vol. 53, pp. 330-335, 2014.

[47] X. Gong et al., "A review of fluorescent signal-based lateral flow immunochromatographic strips.," J. Mater. Chem. B, vol. 5, no. 26, pp. 5079-5091, 2017.

[48] K. M. Koczula and A. Gallotta, "Lateral flow assays," Essays Biochem., vol. 60, no. 1, pp. 111-120, 2016.

[49] J. Wu, M. Lian, and K. Yang, "Micropumping of biofluids by alternating current electrothermal effects.," Appl. Phys. Lett., vol. 90, no. 23, p. p.234103, 2007.

[50] Z. Qin, W. C. Chan, D. R. Boulware, T. Akkin, E. K. Butler, and J. C. Bischof, "Significantly improved analytical sensitivity of lateral flow immunoassays by using thermal contrast.," Angew. Chemie Int. Ed., vol. 51, no. 18, pp. 4358-4361, 2012.

[51] L. Rivas, A. Medina-Sánchez M.de la Escosura-Muniz, and A. Merkoçi, "Improving sensitivity of gold nanoparticle-based lateral flow assays by using wax-printed pillars as delay barriers of microfluidics," Lab Chip, vol. 14, no. 22, pp. 4406-4414, 2014.

[52] J. Li and J. Macdonald, "Multiplexed lateral flow biosensors: Technological advances for radically improving point-of-care diagnoses.," Biosens. Bioelectron., vol. 83, pp. 177-192, 2016.

[53] D. Burch and M. Z. Bazant, "Design principle for improved three-dimensional ac electro-osmotic pumps," Phys. Rev. E, vol. 77, p. p.055303, 2008.

[54] M. Lian, N. Islam, and J. Wu, "AC electrothermal manipulation of conductive fluids and particles for lab-chip applications.," IET Nanobiotechnology, vol. 1, no. 3, pp. 36-43, 2007.

[55] W. Y. Ng, S. Goh, Y. C. Lam, C. Yang, and I. Rodriguez, "DC-biased AC-electroosmotic and AC-electrothermal flow mixing in microchannels.," Lab Chip, vol. 9, no. 6, pp. 802-809, 2009.

[56] E. Du and S. Manoochehri, "Microfluidic pumping optimization in microgrooved channels with ac electrothermal actuations.," Appl. Phys. Lett., vol. 96, no. 3, p. p.034102, 2010.

[57] M. Z. Bazant et al., "Electrolyte dependence of AC electro-osmosis," Micro Total Anal. Syst., vol. 1, pp. 285-287, 2007.

[58] F. J. Hong, J. Cao, and P. Cheng, "A parametric study of AC electrothermal flow in microchannels with asymmetrical interdigitated electrodes.," Int. Commun. heat mass Transf., vol. 38, no. 3, pp. 275-279, 2011.

[59] S. Park, M. Koklu, and A. BeskoK, "Particle trapping in high-conductivity media with electrothermally enhanced negative dielectrophoresis.," Anal. Chem., vol. 81, no. 6, pp. 2303-2310, 2009.

[60] A. Koklu, J. Giuliani, C. Monton, and A. Beskok, Rapid and Sensitive Detection of Nanomolecules by AC Electrothermal Flow Facilitated Impedance Immunosensor. Analytical Chemistry, 2020.

[61] A. Sargent and O. A. Sadik, "Monitoring antibody—antigen reactions at conducting polymer-based immunosensors using impedance spectroscopy.," Electrochim. Acta, vol. 44, no. 26, pp. 4667-4675, 1999.

[62] E. Katz and I. Willner, "Probing biomolecular interactions at conductive and semiconductive surfaces by impedance spectroscopy: routes to impedimetric immunosensors, DNA-sensors, and enzyme biosensors," Electroanal. An Int. J. Devoted to Fundam. Pract. Asp. Electroanal., vol. 15, no. 11, pp. 913-947, 2003.

[63] M. I. Prodromidis, "Impedimetric immunosensors—A review.," Electrochim. Acta, vol. 55, no. 14, pp. 4227-4233, 2010.

[64] S. R. Shin et al., "Aptamer-based microfluidic electrochemical biosensor for monitoring cell-secreted trace cardiac biomarkers.," Anal. Chem., vol. 88, no. 20, pp. 10019-10027, 2016.

[65] S. A. Pfeiffer and S. Nagl, "Microfluidic platforms employing integrated fluorescent or luminescent chemical sensors: a review of methods, scope and applications," Methods Appl. Fluoresc., vol. 3, no. 3, p. 034003, 2015.

[66] Z. Liao et al., "Microfluidic chip coupled with optical biosensors for simultaneous detection of multiple analytes: A review.," Biosens. Bioelectron., vol. 126, pp. 697-706, 2019.

[67] L. Rodriguez-Lorenzo, L. Fabris, and R. A. Alvarez-Puebla, "Multiplex optical sensing with surface-enhanced Raman scattering: a critical review.," Anal. Chim. Acta, vol. 745, pp. 10-23, 2012.

[68] Y. Zhao, H. C. Shum, H. Chen, L. L. Adams, Z. Gu, and D. A. Weitz, "Microfluidic generation of multifunctional quantum dot barcode particles.," J. Am. Chem. Soc., vol. 133, no. 23, pp. 8790-8793, 2011.

[69] T. F. Didar, A. M. Foudeh, and M. Tabrizian, "Patterning multiplex protein microarrays in a single microfluidic channel.," Anal. Chem., vol. 84, no. 2, pp. 1012-1018, 2012.

[70] S. M. Yoo and S. Y. Lee, "Optical biosensors for the detection of pathogenic microorganisms.," Trends Biotechnol., vol. 34, no. 1, pp. 7-25, 2016.

[71] M. Hasanzadeh and N. Shadjou, "Advanced nanomaterials for use in electrochemical and optical immunoassays of carcinoembryonic antigen. A review.," Microchim. Acta, vol. 184, no. 2, pp. 389-414, 2017.

[72] K. V. Kaler and R. Prakash, "Droplet microfluidics for chip-based diagnostics.," Sensors, vol. 14, no. 12, pp. 23283-23306, 2014.

[73] Z. Liao et al., "Recent advances in microfluidic chip integrated electronic biosensors for multiplexed detection.," Biosens. Bioelectron., vol. 121, pp. 272-280, 2018.

[74] K. N. Han, C. A. Li, and G. H. Seong, "Microfluidic chips for immunoassays.," Annu. Rev. Anal. Chem., vol. 6, pp. 119-141, 2013.

[75] H. Bridle, B. Miller, and M. P. Desmulliez, "Application of microfluidics in waterbome pathogen monitoring: A review. water research," vol. 55, pp. 256-271, 2014.

[76] F. Tan et al., "A PDMS microfluidic impedance immunosensor for *E. coli* O157: H7 and *Staphylococcus aureus* detection via antibody-immobilized nanoporous membrane.," Sensors Actuators B Chem., vol. 159, no. 1, pp. 328-335, 2011.

[77] N. Ruecha, K. Shin, O. Chailapakul, and N. Rodthongkum, "Label-free paper-based electrochemical impedance immunosensor for human interferon gamma detection," Sensors Actuators, B Chem., vol. 279, pp. 298-304, January 2019.

[78] J. Leva-Bueno, S. A. Peyman, and P. A. Millner, A review on impedimetric immunosensors for pathogen and biomarker detection. Medical Microbiology and Immunology. 2020.

[79] D. Barat, D. Spencer, G. Benazzi, M. C. Mowlem, and H. Morgan, "Simultaneous high speed optical and impedance analysis of single particles with a microfluidic cytometer," Lab on a Chip, vol. 12, no. 1, pp. 118-126, 2012.

[80] J. Chen, C. Xue, Y. Zhao, D. Chen, M. H. Wu, and J. Wang, "Microfluidic impedance flow cytometry enabling high-throughput single-cell electrical property characterization," Int. J. Mol. Sci., vol. 16, no. 5, pp. 9804-9830, 2015.

[81] M. Frankowski, P. Simon, N. Bock, A. El-Hasni, U. Schnakenberg, and J. Neukammer, "Simultaneous optical and impedance analysis of single cells: A comparison of two microfluidic sensors with sheath flow focusing," Eng. Life Sci., vol. 15, no. 3, pp. 286-296, 2015.

[82] A. Koklu, A. Mansoorifar, J. Giuliani, C. Monton, and A. Beskok, "Self-Similar Interfacial Impedance of Electrodes in High Conductivity Media: II. Disk Electrodes," Anal. Chem., vol. 91, no. 3, pp. 2455-2463, 2019.

[83] D. Bera, S. C. Kuiry, and S. Seal, "Synthesis of nanostructured materials using template-assisted electrodeposition," Jom, vol. 56, no. 1, pp. 49-53, 2004.

[84] C. M. Nguyen, S. Rao, J. C. Chiao, H. Cao, A. Li, and Y. B. Peng, "Miniature neurotransmitter sensors featured with iridium oxide nanorods," in IEEE SENSORS, 2014, vol. 2014, pp. 1869-1872.

[85] C. M. Nguyen, S. Rao, Y. S. Seo, K. Schadt, Y. Hao, and J. C. Chiao, "Micro pH Sensors Based on Iridium Oxide Nanotubes," IEEE Trans. Nanotechnol., vol. 13, no. 5, pp. 945-953, September 2014, doi: 10.1109/TNANO.2014.2332871.

[86] L. Hu and G. Xu, "Applications and trends in electrochemiluminescence.," Chem. Soc. Rev., vol. 39, no. 8, pp. 3275-3304, 2010.

[87] W. C. Chan and S. Nie, "Quantum dot bioconjugates for ultrasensitive nonisotopic detection," Science (80-.)., vol. 281, no. 5385, pp. 2016-2018, 1998.

[88] W. C. Chan, D. J. Maxwell, X. Gao, R. E. Bailey, M. Han, and S. Nie, "Luminescent quantum dots for multiplexed biological detection and imaging," Curr. Opin. Biotechnol., vol. 13, no. 1, pp. 40-46, 2002.

[89] A. M. Smith, X. Gao, and S. Nie, "Quantum Dot Nanocrystals for In Vivo Molecular and Cellular Imaging.," Photochem. Photobiol., vol. 80, no. 3, pp. 377-385, 2004.

[90] J. Wang, G. Liu, H. Wu, and Y. Lin, "Quantum-Dot-based electrochemical immunoassay for high-throughput screening of the prostate-specific antigen.," Small, vol. 4, no. 1, pp. 82-86, 2008.

[91] Z. Zou et al., "Quantum dot-based immunochromatographie fluorescent biosensor for biomonitoring trichloropyridinol, a biomarker of exposure to chlorpyrifos," Anal. Chem., vol. 82. no. 12, pp. 5125-5133, 2010.

[92] Y. M. Kim, S. W. Oh, S. Y. Jeong, D. J. Pyo, and E. Y. Choi, "Development of an ultrarapid one-step fluorescence immunochromatographic assay system for the quantification of microcystins.," Environ. Sci. Technol., vol. 37, no. 9, pp. 1899-1904, 2003.

[93] S. Choi, E. Y. Choi, H. S. Kim, and S. W. Oh, "On-site quantification of human urinary albumin by a fluorescence immunoassay," Clin. Chem., vol. 50, no. 6, pp. 1052-1055, 2004.

[94] H. H. Gerdes and C. Kaether, "Green fluorescent protein: applications in cell biology," FEBS Lett., vol. 389, no. 1, pp. 44-47, 1996.

[95] R. Y. Tsien, The green fluorescent protein. 1998.

[96] A. F. Fradkov et al., "Far-red fluorescent tag for protein labelling," Biochem. J., vol. 368, no. 1, pp. 17-21, 2002.

[97] T. Kobayashi, N. Morone, T. Kashiyama, H. Oyamada, N. Kurebayashi, and T. Murayama, "Engineering a novel multifunctional green fluorescent protein tag for a wide variety of protein research," PLOS One, vol. 3, p. 12, 2008.

[98] V. K. Lin, S. Y. Wang, L. Wu, S. M. Rao, J. C. Chiao, and C. G. Rochrborn, "Molecular Characterization of Epithelial to Mesenchymal Transition in Human Prostatic Epithelial Cells.," J. Nanotechnol. Eng. Med., vol. 1, p. 2, 2010.

[99] U. Tata et al., "Study of lung-metastasized prostate cancer cell line chemotaxis to epidermal growth factor with a BIOMEMS device.," Adv. Nat. Sci. Nanosci. Nanotechnol., vol. 3, no. 3, p. p.035007, 2012.

[100] S. Rao, U. Tata, V. K. Lin, and J. C. Chiao, "The migration of cancer cells in gradually varying chemical gradients and mechanical constraints.," Micromachines, vol. 5, no. 1, pp. 13-26, 2014.

[101] M.-N. Rao and A. M. S., Platform To Study Cell Migration. Dissertation, 2009.

[102] Y. Zhao, Q. Yan, X. Long, X. Chen, and Y. Wang, "Vimentin affects the mobility and invasiveness of prostate cancer cells," Cell Biochem. Funct. Cell. Biochem. its Modul. by Act. agents or Dis., vol. 26, no. 5, pp. 571-577, 2008.

[103] K. M. Mrozik, O. W. Blaschuk, C. M. Cheong, A. C. W. Zannettino, and K. Vandyke, "N-cadherin in cancer metastasis, its emerging role in haematological malignancies and potential as a therapeutic target in cancer," BMC Cancer, vol. 18, no. 1, p. 939, 2018.

[112] K. M. Gattas-Asfura et al., "Immobilization of quantum dots in the photo-cross-linked poly (ethylene glycol)-based hydrogel.," J. Phys. Chem. B, vol. 107, no. 38, pp. 10464-10469, 2003.

[113] X. Guo, Y. Chen, L. Zhang, and W. Liu, "An inkjet printing paper-based immunodevice for fluorescence determination of immunoglobulin G.," Anal. Methods, vol. 11, no. 27, pp. 3452-3459, 2019.

What is claimed is:

1. A method for detecting one or more target molecules comprising:
   providing an apparatus comprising:
   a fluidic chamber formed by a hydrophobic substrate, one or more walls and a hydrophobic cover,
   one or more fluidic ports disposed within the hydrophobic cover and connected to the fluidic chamber, and
   a sensor disposed within the fluidic chamber, the sensor comprising:

two or more electrodes disposed on the hydrophobic substrate and separated from one another by a gap;

a plurality of nanostructures formed on or within an upper surface of each electrode;

a plurality of binding molecules attached to the plurality of nanostructures, wherein the plurality of binding molecules are configured to bind with the one or more target molecules;

a multiplexor coupled to the two or more electrodes configured to selectively switch the two or more electrodes between inducing an alternating current electrothermal (ACET) flow and detecting the one or more target molecules; and an alternating current power source and impedance analyzer coupled to the multiplexor;

wherein the upper surface of each electrode and the plurality of nanostructures are hydrophilic;

introducing a fluid into the fluidic chamber via the one or more fluidic ports;

inducing an alternating current electrothermal (ACET) flow using the two or more electrodes and an alternating current power source coupled to the two or more electrodes; and detecting whether the one or more target molecules are present in the fluid by determining whether there is a change in an impedance of the two or more electrodes.

2. The method of claim 1, wherein the change in the impedance of the sensor is caused by the one or more target molecules bonding with the plurality of binding molecules.

3. The method of claim 1, wherein the two or more electrodes or a set of electrical conductors connected to the two or more electrodes extend outside the fluidic chamber.

4. The method of claim 1, wherein:

the hydrophobic substrate comprises a glass, SiO2, semiconductor or plastic material treated with a silylation reagent;

each electrode is made of or coated with chromium and each electrode is made of or coated with one or more metals or conductive organic polymers; and each nanostructure is made of or coated with the one or more metals or conductive organic polymers treated with ultraviolet light, or wherein the silylation reagent comprises tridecafluorooctyltriethoxysilane, heptadecafluorodecyl trimethoxysilane, actadecyltrichlorosilane, n-octadecanethiol, self-assemble of alkanoic acid through a solution-immersion process, or hexamethyl-disilazane (HMDS).

5. The method of claim 1, wherein the two or more electrodes comprise three interdigitated electrodes.

6. The method of claim 1, wherein a fluidic chamber is formed by one or more walls and a hydrophobic cover enclosing at least a portion of the two or more electrodes or wherein the fluidic chamber comprises a microchannel loop, one or more fluidic ports disposed within the hydrophobic cover and connected to the fluidic chamber, and wherein the two or more electrodes or a set of electrical conductors connected to the two or more electrodes extend outside the fluidic chamber, or wherein the sensor comprises two or more sensors, wherein each sensor is selectively addressable, or wherein the two or more sensors comprise at least a first set of sensors and a second set of sensors;

wherein the plurality of binding molecules of the first set of sensors comprise a plurality of first binding molecules configured to bind with one or more first target molecules, and the plurality of binding molecules of the second set of sensors comprise a plurality of second binding molecules configured to bind with one or more second target molecules;

wherein the first set of sensors detect the one or more target molecules while the second set of sensors simultaneously induce an alternating current electrothermal (ACET) flow, and the second set of sensors detect the one or more target molecules while the first set of sensors simultaneously induce the alternating current electrothermal (ACET) flow;

wherein at least one of: an impedance measurement interface connected to the sensor; a portable electronic device or a desktop device coupled to the impedance measurement interface, wherein the impedance measurement interface is integrated into the portable electronic device or the desktop device; or wherein the apparatus is packaged into a cartridge configured to interface with an electronic device; or wherein the apparatus is defined as further comprising 3, 4, 5, 6, 7, 8, 9, 10, 11, 12, 13, 14, 15, 16, 17, 18, 19, 20, or more fluid channels that extend from a central reservoir, wherein each channel comprises one or more sensors.

7. The method of claim 1, wherein the apparatus is defined as further comprising two or more sensors that detect two or more different modalities, wherein the modalities are selected from at least one of: electrical (impedance, capacitance, resistance) at different operating frequencies; optical fluorescence (amplitude) at different wavelengths; optical resonance (amplitude, phase) at different wavelengths; magnetic detection (magnitude and induced impedance); and/or sur-face acoustic waves (impedance, magnitude, phase) at different operating frequencies.

8. The method of claim 1, wherein the two or more modalities can be detected simultaneously without interferences by selecting electromagnetic frequencies/wavelengths at different spectrums, optically detect dyes or chromophores, electrically detecting contact with the sensors, opening or closing of ionic pores, current flow, impedance, resistivity, acoustic waves, resonance, a magnetic field or changes to the magnetic field.

9. The method of claim 1, wherein the target molecules are detected within a few seconds with a 1 ng/ml sensitivity.

* * * * *